US006903186B1

(12) United States Patent
Dong

(10) Patent No.: US 6,903,186 B1
(45) Date of Patent: Jun. 7, 2005

(54) ANALOGUES OF GLP-1

(75) Inventor: Zheng Xin Dong, Holliston, MA (US)

(73) Assignee: Societe de Conseils de Recherches et d'Applications Scientifiques, S.A.S, Paris (FR)

(*) Notice: Subject to any disclaimer, the term of this patent is extended or adjusted under 35 U.S.C. 154(b) by 0 days.

(21) Appl. No.: 09/857,636

(22) PCT Filed: Dec. 7, 1999

(86) PCT No.: PCT/EP99/09660
§ 371 (c)(1),
(2), (4) Date: Nov. 2, 2001

(87) PCT Pub. No.: WO00/34331
PCT Pub. Date: Jun. 15, 2000

Related U.S. Application Data

(63) Continuation-in-part of application No. 09/206,601, filed on Dec. 7, 1998, now abandoned.
(60) Provisional application No. 60/111,255, filed on Dec. 7, 1998.

(51) Int. Cl.$^7$ ............................................. C07K 14/605
(52) U.S. Cl. ........................... 530/324; 530/399; 514/12
(58) Field of Search ................................. 530/324, 399; 514/12

(56) References Cited

U.S. PATENT DOCUMENTS

| 5,545,618 | A | 8/1996 | Buckley et al. ................ 514/12 |
| 5,705,483 | A | 1/1998 | Galloway et al. ............. 514/12 |
| 6,458,924 | B2 * | 10/2002 | Knudsen et al. ............ 530/324 |
| 6,620,910 | B1 * | 9/2003 | Calas et al. .................. 530/324 |
| 6,720,407 | B1 * | 4/2004 | Hughes et al. .............. 530/324 |

FOREIGN PATENT DOCUMENTS

| EP | 0 658 568 A1 | 6/1995 |
| EP | 0 699 686 A2 A3 | 3/1996 |
| EP | 0 708 179 A2 A3 | 4/1996 |
| EP | 0 733 644 A1 | 9/1996 |
| EP | 0 869 135 A1 | 10/1998 |
| WO | WO 87/06941 | 11/1987 |
| WO | WO 91/11457 | 8/1991 |
| WO | WO 97/29180 | 8/1997 |
| WO | WO 98/03547 | 1/1998 |
| WO | WO 98/08871 | 3/1998 |
| WO | WO 98/19698 | 5/1998 |

OTHER PUBLICATIONS

English Abstract of Hungarian patent P9501508 (1997).*
B. Thorens et al., "*Perspectives in Diabetes, Glucagon–Like Peptide–l and the control of Insulin Secretion in the Normal State and in NIDDM*", Diabetes, vol. 42, Sep. 1993, pp. 1219–1225.

Ahren, Bo, et al.; "Effects of Glucagon–Like Peptide–1 on Islet Function and Insulin Sensitivity in Noninsulin–Dependent Diabetes Mellitus"; 1997; Journal of Clinical Endocrinology and Metabolism; vol. 82:2; pp. 473–478.

Deacon, C.F., et al.; "Dipeptidyl peptidase IV resistant analogues of glucagon–like peptide–1 which have extended metabolic stability and improved biological activity"; 1998; Diabetologia; vol. 41; pp. 271–278.

Deacon, C.F., et al.; "Dipeptidyl Peptidase IV Inhibition Potentiates the Insulinotropic Effect of Glucagon–Like Peptide 1 in the Anesthetized Pig"; 1998; Diabetes; vol. 47; pp. 764–769.

Gutniak, Mark, et al.; "Antidiabetogenic Effect of Glucagon–Like Peptide–1 (7–36) Amide in Normal Subjects and Patients with Diabetes Mellitus"; 1992; The New England Journal of Medicine; vol. 326 No. 20; pp. 1316–1322.

Mentlein, R., et al; "Dipeptidyl–peptidase IV hydrolyses gastric inhibitory polypeptide, Glucagon–like peptide–1 (7–36) amide, peptide histidine methionine and is responsible for their degradation in human serum"; 1993; Biochem; vol. 214; pp. 829–835.

Nauck, M.A., et al.; "Effects of subcutaneous glucagon–like peptide 1 (GLP–1 [7–36 amide]) in patients with NIDDM"; 1996; Diabetologia; vol. 82:2; pp. 1546–1553.

Parker, J.C., et al.; "Structure–function analysis of a series of glucagon–like peptide–1 analogs"; 1998; Peptide Res; vol. 52:5; pp. 398–409; XP–000788444.

Rachman, J., et al.; "Near–normalisation of diurnal glucose concentrations by continuous administration of glucagonlike peptide–1 (GLP–1) in subjects with NIDDM"; 1997; Diabetologia; vol. 40; pp. 205–211.

Suzuki, S., et al.; "Comparison of the Effects of Various C–Terminal and N–Terminal Fragment Peptides of Glucagon–Like Peptide–1 on Insulin and Glucagon Release from the Isolated Perfused Rat Pancreas"; 1989; Endocrinology; vol. 125:6; pp. 3109–3114.

Thorens, Bernard, et al.; "Structure and Function of the Glucagon–Like Peptide–1 Receptor"; 1996; Handbook of Experimental Pharmacology; vol. 123; pp. 255–273.

Todd, J.F., et al.; "Glucagon–like peptide–1 (GLP–1): a trial of treatment in non–insulin–dependent diabetes mellitus"; 1997; European Journal of Clinical Investigation; vol. 27; pp. 533–536.

* cited by examiner

Primary Examiner—Jon Weber
Assistant Examiner—David Lukton
(74) Attorney, Agent, or Firm—Fish & Richardson; Brian R. Morrill; Alan F. Feeney

(57) ABSTRACT

The present invention is directed to peptide analogues of glucagon-like peptide-1, the pharmaceutically-acceptable salts thereof, to methods of using such analogues to treat mammals and to pharmaceutical compositions useful therefor comprising said analogues.

2 Claims, No Drawings

ANALOGUES OF GLP-1

CROSS-REFERENCE TO RELATED APPLICATIONS

This application is a national phase application filed under 35 U.S.C. 371 of International Application No. PCT/EP99/09660, filed Dec. 7, 1999, and is a continuance-in-part of Ser. No. 09/206,601 filed Dec. 7, 1998 now ABN which claims the benefit of U.S. application No. 60/111,255, filed Dec. 7, 1998, the contents of which are incorporated herein by reference.

BACKGROUND OF THE INVENTION

The present invention is directed to peptide analogues of glucagon-like peptide-1, the pharmaceutically-acceptable salts thereof, to methods of using such analogues to treat mammals and to pharmaceutical compositions useful therefor comprising said analogues.

Glucagon-like peptide-1 (7-36) amide (GLP-1) (SEQ ID NO:1) is synthesized in the car intestinal L-cells by tissue-specific post-translational processing of the glucagon precursor z C preproglucagon (Varndell, J. M., et al., J. Histochem Cytochem, 1985:33:1080–6) and is released into the circulation in response to a meal. The plasma concentration of GLP-1 rises from a fasting level of approximately 15 pmol/L to a peak postprandial level of 40 pmol/L. It has been a demonstrated that, for a given rise in plasma glucose concentration, the increase in plasma insulin is approximately threefold greater when glucose is administered orally compared with intravenously (Kreymann, B., et al., Lancet 1987:2, 1300–4). This alimentary enhancement of insulin release, known as the incretin effect, is primarily humoral and GLP-1 is now thought to be the most potent physiological incretin in humans. In addition to the insulinotropic effect, GLP-1 suppresses glucagon secretion, delays gastric emptying (Wettergren A., et al., Dig Dis Sci 1993:38:665–73) and may enhance peripheral glucose disposal (D'Alessio, D. A. et al., J. Clin Invest 1994:93:2293–6).

In 1994, the therapeutic potential of GLP-1 was suggested following the observation that a single subcutaneous (s/c) dose of GLP-1 could completely normalize postprandial glucose levels in patients with non-insulin-dependent diabetes mellitus (NIDDM) (Gutniak, M. K. et al. Diabetes Care 1994:17:1039–44). This effect was thought to be mediated both by increased insulin release and by a reduction in glucagon secretion. Furthermore, an intravenous infusion of GLP-1 has been shown to delay postprandial gastric emptying in patients with NIDDM (Williams, B., et al., J. Clin Endo Metab 1996:81:327–32). Unlike sulphonylureas, the insulinotropic action of GLP-1 is dependent on plasma glucose concentration (Holz, G. G. 4$^{th}$, et al., Nature 1993:361:362–5). Thus, the loss of GLP-1-mediated insulin release at low plasma glucose concentration protects against severe hypoglycemia. This combination of actions gives GLP-1 unique potential therapeutic advantages over other agents currently used to treat NIDDM.

Numerous studies have shown that when given to healthy subjects, GLP-1 potently influences glycemic levels as well as insulin and glucagon concentrations (Orskov, C, Diabetologia 35:701–711, 1992; Hoist, J. J., et a)., *Potential of GLP-1 in diabetes management* in Glucagon III, Handbook of Experimental Pharmacology, Lefevbre PJ, Ed. Berlin, Springer Verlag, 1996, p. 311–326), effects which are glucose dependent (Kreymann, B., et al., Lancet ii: 1300–1304, 1987; Weir, G. C., et al., Diabetes 38:338–342, 1989).

Moreover, it is also effective in patients with diabetes (Gutniak, M., N. Engl J Med 226:1316–1322, 1992; Nathan, D. M., et al., Diabetes Care 15:270–276, 1992), normalizing blood glucose levels in type 2 diabetic subjects (Nauck, M. A., et al., Diagbetologia 36:741–744, 1993), and improving glycemic control in type I patients (Creutzfeldt, W. O., et al., Diabetes Care 19:580–586, 1996), raising the possibility of its use as a therapeutic agent.

GLP-1 is, however, metabolically unstable, having a plasma half-life ($t_{1/2}$) of only 1–2 min in vivo. Exogenously administered GLP-1 is also rapidly degraded (Deacon, C. F., et al., Diabetes 44:1126–1131, 1995). This metabolic instability limits the therapeutic potential of native GLP-1. Hence, there is a need for GLP-1 analogues that are more active or are more metabolically stable than native GLP-1.

SUMMARY OF THE INVENTION

In one aspect, the present invention is directed to a compound of formula (I),

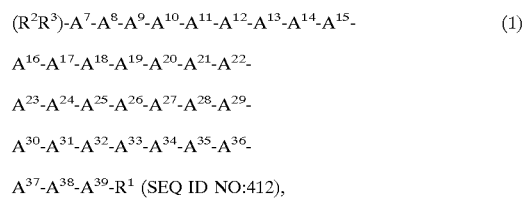

wherein
$A^7$ is L-His, Ura, Paa, Pta, Amp, Tma-His, des-amino-His, or deleted;
$A^8$ is Ala, D-Ala, Aib, Ace, N-Me-Ala, N-Me-D-Ala or N-Me-Gly;
$A^9$ is Glu, N-Me-Glu, N-Me-Asp or Asp;
$A^{10}$ is Gly, Ace, β-Ala or Aib;
$A^{11}$ is Thr or Ser;
$A^{12}$ is Phe, Acc, Aic, Aib, 3-Pal, 4-Pal, β-Nal, Cha, Trp or $X^1$-Phe;
$A^{13}$ is Thr or Ser;
$A^{14}$ is Ser or Aib;
$A^{15}$ is Asp or Glu;
$A^{16}$ is Val, Acc, Aib, Leu, Ile, Tle, Nle, Abu, Ala or Cha;
$A^{17}$ is Ser or Thr;
$A^{18}$ is Ser or Thr;
$A^{19}$ is Tyr, Cha, Phe, 3-Pal, 4-Pal, Acc, β-Nal or $X^1$-Phe;
$A^{20}$ is Leu, Acc, Aib, Nle, Ile, Cha, Tle, Val, Phe or $X^1$-Phe;
$A^{21}$ is Glu or Asp;
$A^{22}$ is Gly, Acc, β-Ala, Glu or Aib;
$A^{23}$ is Gin, Asp, Asn or Glu;
$A^{24}$ is Ala, Aib, Val, Abu, Tie or Acc;
$A^{25}$ is Ala, Aib, Val, Abu, Tle, Acc, Lys, Arg, hArg, Orn, HN—CH$((CH_2)_n$—N$(R^{10}$–$R^{11}))$—C(O) or NH—CH$((CH_2)$—$X^3)$—C(O);
$A^{26}$ is Lys, Arg, hArg, Orn, HN—CH$((CH_2)_n$—N$(R^{10}$–$R^{11}))$-C(O) or NH—CH$((CH_2)_e X^3)$—C(O);
$A^{27}$ is Glu Asp, Leu, Aib or Lys;
$A^{28}$ is Phe, Pal, β-Nal, $X^1$-Phe, Aic, Acc, Aib, Cha or Trp;
$A^{29}$ is Ile, Acc, Aib, Leu, Nle, Cha, Tie, Val, Abu, Ala or Phe;
$A^{30}$ is Ala, Aib or Acc;
$A^{31}$ is Trp, β-Nal, 3-Pal, 4-Pal, Phe, Acc, Aib or Cha;
$A^{32}$ is Leu, Acc, Aib, Nle, Ile, Cha, Tie, Phe, $X^1$-Phe or Ala;
$A^{33}$ is Val, Acc, Aib, Leu, Ile, Tle, Nle, Cha, Ala, Phe, Abu, Lys or $X^1$-Phe;
$A^{34}$ is Lys, Arg, hArg, Orn, HN—CH$((CH_2)_n$—N$(R^{10}$–$R^{11}))$—C(O) or NH—CH$((CH_2)_e$—$X^3)$—C(O);
$A^{35}$ is Gly, β-Ala, D-Ala, Gaba, Ava, NH—$(CH_2)_m$—C(O), Aib, Acc or a D-amino acid, $A^{36}$ is L- or D-Arg, D- or L-Lys, D- or L-hArg, D- or L-Orn, HN—CH(($CH_2$)$_n$—N($R^{10}$–$R^{11}$))—C(O), NH—CH(($CH_2$)$_e$-$X^3$)—C(O) or deleted;

$A^{37}$ is Gly, β-Ala, Gaba, Ava, Aib, Acc, Ado, Arg, Asp, Aun, Aec, NH—($CH_2$)$_m$—C(O), HN—CH(($CH_2$)$_n$—N($R^{10}$–$R^{11}$))-C(O), a D-amino acid, or deleted;

$A^{38}$ is D- or L-Lys, D- or L-Arg, D- or L-hArg, D- or L-Orn, HN—CH(($CH_2$)$_n$—N($R^{10}$–$R^{11}$))-C(O), NH—CH(($CH_2$)$_e$–$X^3$)—C(O), Ava, Ado, Aec or deleted;

$A^{39}$ is D- or L-Lys, D- or L-Arg, HN—CH(($CH_2$)$_n$—N($R^{10}$–$R^{11}$))-C(O), Ava, Ado, or Aec;

$X^1$ for each occurrence is independently selected from the group consisting of ($C_1$–$C_6$)alkyl, OH and halo;

$R^1$ is OH, $NH_2$, ($C_1$–$C_{30}$) alkoxy, or NH—$X^2$—$CH_2$—$Z^0$, wherein $X^2$ is a ($C_1$–$C_{12}$) hydrocarbon moiety, and $Z^0$ is H, OH, $CO_2H$ or $CONH_2$;

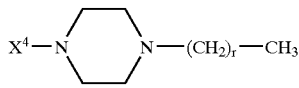

$X^3$ is

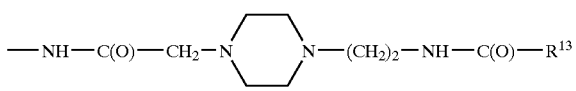

or —C(O)—$NHR^{12}$, wherein $X^4$ is, independently for each occurrence, —C(O)—, —NH—C(O)— or —$CH_2$—and wherein f is, independently for each occurrence, an integer from 1 to 29 inclusive, each of $R^2$ and $R^3$ is independently selected from the group consisting of H, ($C_1$–$C_{30}$)alkyl, ($C_2$–$C_{30}$)alkenyl, phenyl($C_1$–$C_{30}$)alkyl, naphthyl($C_1$–$C_{30}$)alkyl, hydroxy($C_1$–$C_{30}$)alkyl, hydroxy($C_2$–$C_{30}$)alkenyl, hydroxyphenyl($C_1$–$C_{30}$)alkyl, and hydroxynaphthyl($C_1$–$C_{30}$)alkyl; or one of $R^2$ and

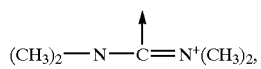

($C_1$–$C_{30}$)acyl, ($C_1$–$C_{30}$)alkylsulfonyl, C(O)$X^5$,

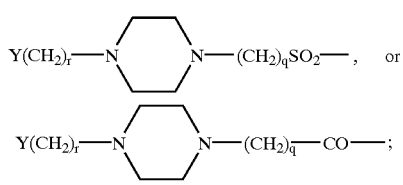

wherein Y is H, OH or $NH_2$; r is 0 to 4; q is 0 to 4; and $X^5$ is ($C_1$–$C_{30}$)alkyl, ($C_2$–$C_{30}$)alkenyl, phenyl($C_1$–$C_{30}$)alkyl, naphthyl($C_1$–$C_{30}$)alkyl, hydroxy($C_1$–$C_{30}$)alkyl, hydroxy ($C_2$–$C_{30}$)alkenyl, hydroxyphenyl($C_1$–$C_{30}$)alkyl or hydroxynaphthyl($C_1$–$C_{30}$)alkyl;

e is, independently for each occurrence, an integer from 1 to 4 inclusive;

m is, independently for each occurrence, an integer from 5 to 24 inclusive;

n is, independently for each occurrence, an integer from 1 to 5, inclusive;

each of $R^{10}$ and $R^{11}$ is, independently for each occurrence, H, ($C_1$–$C_{30}$)alkyl, ($C_1$–$C_{30}$)acyl, ($C_1$–$C_{30}$)alkylsulfonyl, —C((NH)($NH_2$)) or

and $R^{12}$ and $R^{13}$ each is, independently for each occurrence, ($C_1$–$C_{30}$)alkyl;

provided that:

when $A^7$ is Ura, Paa or Pta, then $R^2$ and $R^3$ are deleted;

when $R^{10}$ is ($C_1$–$C_{30}$)acyl, ($C_1$–$C_{30}$)alkylsulfonyl, —C((NH)($NH_2$)) or

then $R^{11}$ is H or ($C_1$–$C_{30}$)alkyl;

(i) at least one amino acid of a compound of formula (I) is not the same as the native sequence of hGLP-1(7-36, -37 or -38)$NH_2$ or hGLP-1(7-36, -37 or -38)OH;

(ii) a compound of formula (I) is not an analogue of hGLP-1 (7-36, -37 or -38)$NH_2$ or hGLP-1(7-36, -37 or -38)OH wherein a single position has been substituted by Ala;

(iii) a compound of formula (I) is not (Arg$^{26,34}$, Lys$^{38}$) hGLP-1(7-38)-E, (Lys$^{26}$(N$_\epsilon$-alkanoyl))hGLP-(7-36, -37 or -38)-E, (Lys$^{34}$(N$_\epsilon$-alkanoyl))hGLP-1(7-36, -37 or -38)-E, (Lys$^{26,34}$-bis(N$_\epsilon$-alkanoyl))hGLP-1(7-36, -37 or -38)-E, (Arg$^{26}$, Lys$^{34}$(N$_\epsilon$-alkanoyl))hGLP-1 (8-36, -37 or -38)-E, (Arg$^{26,34}$, Lys$^{36}$(N$_\epsilon$-alkanoyl))hGLP-1(7-36, -37 or -38)-E or (Arg$^{26,34}$, Lys$^{38}$(N$_\epsilon$-alkanoyl))hGLP-1(7-38)-E, wherein E is —OH or —$NH_2$;

(iv) a compound of formula (I) is not $Z^1$-hGLP-1(7-36, -37 or -38)—OH, $Z^1$-hGLP-1(7-36, -37 or -38)—$NH_2$, wherein $Z^1$ is selected from the group consisting of:
(a) (Arg$^{26}$), (Arg$^{34}$), (Arg$^{26,34}$), (Lys$^{36}$), (Arg$^{26}$, Lys$^{36}$), (Arg$^{34}$, Lys$^{36}$), (D-Lys$^{36}$), (Arg$^{36}$), (D-Arg$^{36}$), (Arg$^{26,34}$, Lys$^{36}$) or (Arg$^{26,36}$, Lys$^{34}$);
(b) (Asp$^{21}$);
(c) at least one of (Aib$^8$), (D-Ala$^8$) and (Asp$^9$); and
(d) (Tyr$^7$), (N-acyl-His$^7$), (N-alkyl-His$^7$), (N-acyl-D-His$^7$) or (N-alkyl-D-His$^7$);

(v) a compound of formula (I) is not a combination of any two of the substitutions listed in groups (a) to (d); and (vi) a compound of formula (I) is not (N-Me-Ala$^8$)hGLP-1(8-36 or -37), (Glu$^{15}$)hGLP-1(7-36 or -37), (Asp$^{21}$)hGLP-1(7-36 or -37) or (Phe$^{31}$)hGLP-1(7-36 or -37) or a pharmaceutically acceptable salt thereof.

A preferred group of compounds of the immediately foregoing compound is where $A^{11}$ is Thr; $A^{13}$ is Thr; $A^{15}$ is Asp; $A^{17}$ is Ser; $A^{18}$ is Ser or Lys; $A^{21}$ is Glu; $A^{23}$ is Gln or Glu; $A^{27}$ is Glu, Leu, Aib or Lys; and $A^{31}$ is Trp, Phe or β-Nal; or a pharmaceutically acceptable salt thereof.

A preferred group of compounds of the immediately foregoing group of compounds is where $A^9$ is Glu, N-Me-Glu or N-Met-Asp; $A^{12}$ is Phe, Acc, β-Nal or Aic; $A^{16}$ is Val, Acc or Aib; $A^{19}$ is Tyr or β-Nal; $A^{20}$ is Leu, Acc or Cha; $A^{24}$ is Ala, Aib or Acc; $A^{25}$ is Ala, Aib, Acc, Lys, Arg, hArg, Orn, HN—CH(($CH_2$)$_n$—N($R^{10}R^{11}$))-C(O) or HN—CH(($CH_2$)$_e$—$X^3$)—C(O); $A^{28}$ is Phe or β-Nal; $A^{29}$ is Ile or Acc; $A^{30}$ is Ala or Aib; $A^{32}$ is Leu, Acc or Cha; and $A^{33}$ is Val, Lys or Acc; or a pharmaceutically acceptable salt thereof.

A preferred group of compounds of the immediately foregoing group of compounds is where $A^8$ is Ala, D-Ala, Aib, A6c, A5c, N-Me-Ala, N-Me-D-Ala or N-Me-Gly; $A^{10}$ is Gly; $A^{12}$ is Phe, β-Nal, A6c or A5c; $A^{26}$ is Val, A6c or A5° c.; $A^{20}$ is Leu, A6c, A5c or Cha; $A^{22}$ is Gly, β-Ala, Glu or Aib; $A^{24}$ is Ala or Aib; $A^{29}$ is Ile, A6c or A5c; $A^{32}$ is Leu, A6c, A5c or Cha; $A^{33}$ is Val, Lys, A6c or A5c; $A^{35}$ is Aib, β-Ala, Ado, A6c, A5c, D-Arg or Gly; and $A^{37}$ is Gly, Aib, β-Ala, Ado, D-Ala, Ava, Asp, Aun, D-Asp, D-Arg, Aec, HN—CH(($CH_2$)$_n$—N($R^{10}R^{11}$))-C(O) or deleted; or a pharmaceutically acceptable salt thereof.

A preferred group of compounds of the immediately foregoing group of compounds is where $X^4$ for each occurrence is —C(O)—; and $R^1$ is OH or $NH_2$; or a pharmaceutically acceptable salt thereof.

A preferred group of compounds of the immediately foregoing group of compounds or a pharmaceutically acceptable salt thereof is where $R^2$ is H and $R^3$ is ($C_1$–$C_{30}$)alkyl, ($C_2$–$C_{30}$)alkenyl, ($C_1$–$C_{30}$)acyl, ($C_1$–$C_{30}$)alkylsulfonyl,

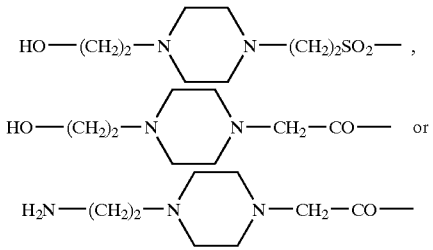

A preferred compound of the formula (I) is where $A^8$ is Ala, D-Ala, Aib, A6c, A5c, N-Me-Ala, N-Me-D-Ala or N-Me-Gly; $A^{10}$ is Gly; $A^{12}$ is Phe, β-Nal, A6c or A5c; $A^{16}$ is Val, A6c or A5c; $A^{20}$ is Leu, A6c, A5c or Cha; $A^{22}$ is Gly, β-Ala, Glu or Aib; $A^{24}$ is Ala or Aib; $A^{29}$ is Ile, A6c or A5c; $A^{32}$ is Leu, A6c, A5c or Cha; $A^{33}$ is Val, Lys, A6c or A5c; $A^{35}$ is Aib, β-Ala, Ado, A6c, A5c, D-Arg or Gly; and $A^{37}$ is Gly, Aib, β-Ala, Ado, D-Ala, Ava, Asp, Aun, D-Asp. D-Arg, Aec, HN—CH(($CH_2$)$_n$—N($R^{10}R^{11}$))-C(O) or deleted; $X^4$ for each occurrence is —C(O)—; e for each occurrence is independently 1 or 2; $R^1$ is OH or $NH_2$; $R^{10}$ is ($C_1$–$C_{30}$)acyl, ($C_1$–$C_{30}$)alkylsulfonyl or

and $R^{11}$ is H; or a pharmaceutically acceptable salt thereof.

More preferred of the immediately foregoing compounds is where $R^{10}$ is ($C_4$–$C_{20}$)acyl, ($C_4$–$C_{20}$)alkylsulfonyl or

or a pharmaceutically acceptable salt thereof.

A more preferred compound of formula (I) is where said compound is of the formula:
(Aib$^{8,35}$)hGLP-1(7-36)$NH_2$ (SEQ ID NO:2),
((N$_\alpha$-HEPES-His)$^7$, Aib$^{8,35}$)hGLP-1(7-36)$NH_2$ (SEQ ID NO:3),
((N$_\alpha$-HEPA-His)$^7$, Aib$^{8,35}$)hGLP-1(7-36)$NH_2$ (SEQ ID NO:4),
(Aib$^8$, β-Ala$^{35}$)hGLP-1(7-36)$NH_2$ (SEQ ID NO:5),
(Aib$^{8,35}$, Arg$^{26,34}$, Lys$^{36}$(Ne-tetradecanoyl))hGLP-1(7-36)$NH_2$ (SEQ ID NO:6),
(Aib$^{8,35}$, Arg$^{26,34}$, Lys$^{34}$ (N-tetradecanoyl))hGLP-1(7-36)$NH_2$ (SEQ ID NO:7),
(Aib$^{8,35,37}$, Arg$^{26,34}$, Lys$^{36}$(N-tetradecanoyl))hGLP-1 (7-38)$NH_2$ (SEQ ID NO:8),
(Aib$^{8,35}$, Arg$^{26,34}$, Lys$^{36}$(N$_\epsilon$-decanoyl))hGLP-1 (7-36)$NH_2$ (SEQ ID NO:9),
(Aib$^{8,35}$, Arg$^{26,34}$, Lys$^{36}$(N$_\epsilon$-dodecanesulfonyl))hGLP-1(7-36)$NH_2$ (SEQ ID NO:10).
(Aib$^{8,35}$, Arg$^{26,34}$, Lys$^{36}$(N$_\epsilon$-(2-(4-tetradecyl-1-piperazine)-acetyl)))hGLP-1 (7-36)$NH_2$ (SEQ ID NO:11),
(Aib$^{8,35}$, Arg$^{26,34}$, Asp$^{36}$(1-(4-tetradecyl-piperazine)))hGLP-1(7-36)$NH_2$ (SEQ ID NO:12),
(Aib$^{8,35}$, Arg$^{26,34}$, Asp$^{36}$(1-tetradecylamino))hGLP-1(7-36)$NH_2$ (SEQ ID NO:13),
(Aib$^{8,35}$, Arg$^{26,34}$, Lys $^{36}$(N$_\epsilon$-tetradecanoyl), β-Ala$^{37}$)hGLP-1(7-37)—OH (SEQ ID NO: 14) or
(Aib$^{8,35}$, Arg$^{26,34}$, Lys$^{36}$(N$_\epsilon$-tetradecanoyl))hGLP-1(7-36)—OH (SEQ ID NO: 15), or a pharmaceutically acceptable salt thereof.

More preferred of the immediately foregoing group of compounds is a compound of the formula:
(Aib$^{8,35}$)hGLP-1 (7-36)$NH_2$ (SEQ ID NO:2),
(Aib$^8$, β-Ala$^{35}$)hGLP-1(7-36)$NH_2$ (SEQ ID NO:5),
(Aib$^{8,35}$, Arg$^{26}$, Lys$^{34}$ (N$_\epsilon$-tetradecanoyl))hGLP-1(7-36)$NH_2$ (SEQ ID NO:7),
(Aib$^{8,35,37}$, Arg$^{26,34}$, Lys$^{38}$(N$_\epsilon$-tetradecanoyl))hGLP-1(7-38)$NH_2$ (SEQ ID NO:8),
(Aib$^{8,35}$, Arg$^{26,34}$, Lys$^{36}$(N$_\epsilon$-decanoyl))hGLP-1(7-36)$NH_2$ (SEQ ID NO:9), or
(Aib$^{8,35}$, Arg$^{26,34}$ Lys$^{36}$(N$_\epsilon$-tetradecanoyl), β-Ala$^{37}$)hGLP-1 (7-37)—OH (SEQ ID NO:14), or a pharmaceutically acceptable salt thereof.

Another more preferred compound of formula (I) is where said compound is of the formula:
(Aib$^{8,35}$, A6c$^{32}$)hGLP-1(7-36)$NH_2$ (SEQ ID NO:16);
(Aib$^{3,35}$, Glu$^{23}$)hGLP-1(7-36)$NH_2$ (SEQ ID NO:17);
(Aib $^{8,24,35}$)hGLP-1 (7-36)$NH_2$ (SEQ ID NO:18);
(Aib$^{8,35}$, Glu$^{23}$, A6c$^{32}$)hGLP-1(7-36)$NH_2$ (SEQ ID NO: 19);
(Aib$^8$, Glu$^{23}$, β-Ala$^{35}$)hGLP-1(7-36)$NH_2$ (SEQ ID NO:20);
(Aib$^{8,35}$, Arg$^{26,34}$)hGLP-1(7-36)$NH_2$ (SEQ ID NO:21);
(Aib$^{8,35}$, Arg$^{26,34}$, Lys$^{36}$(N$^\epsilon$-octanoyl))hGLP-1(7-36)$NH_2$ (SEQ ID NO:22);
(Aib$^{8,35}$, Arg$^{26,34}$, Lys$^{36}$(N$^\epsilon$-decanoyl))hGLP-1 (7-36)OH (SEQ ID NO:23);
(Aib$^{8,35}$, Lys$^{25}$, Arg$^{26,34}$ Lys$^{36}$(N$^\epsilon$-decanoyl))hGLP-1(7-36)OH (SEQ ID NO:24);
(Aib$^8$, Arg$^{26,34}$, β-Ala$^{35}$, Lys$^{36}$(N$^\epsilon$-Aec decanoyl))hGLP-1 (7-36)$NH_2$ (SEQ ID NO:25);
(Aib$^{8,35}$, Arg$^{26,34}$, Ava$^{37}$, Ado$^{39}$)hGLP-1(7-38)$NH_2$ (SEQ ID NO:26);
(Aib$^{8,35}$, Arg$^{26,34}$, Asp$^{37}$, Ava$^{38}$, Ado$^{39}$)hGLP-1(7-39)$NH_2$ (SEQ ID NO:27);
(Aib$^{8,35}$, Arg$^{26,34}$, Aun$^{37}$)hGLP-1(7-37)$NH_2$ (SEQ ID NO:28);
(Aib$^{8,17,35}$)hGLP-1(7-36)$NH_2$ (SEQ ID NO:29);
(Aib$^8$ Arg$^{26,34}$, β-Ala$^{35}$, D-Asp$^{37}$ Ava$^{38}$ Aun$^{39}$)hGLP-1(7-39)$NH_2$(SEQ ID NO:30);
(Gly$^8$, β-Ala$^{35}$)hGLP-1(7-36)$NH_2$ (SEQ ID NO:31);
(Ser$^8$, β-Ala$^{35}$)hGLP-1(7-36)$NH_2$ (SEQ ID NO:32);
(Aib$^8$, Glu$^{22,23}$, β-Ala$^{35}$)hGLP-1(7-36)$NH_2$ (SEQ ID NO:33);
(Gly$^8$, Aib$^{35}$)hGLP-1(7-36)$NH_2$ (SEQ ID NO:34);
(Aib$^8$, Lys$^{18}$, β-Ala$^{35}$)hGLP-1(7-36)$NH_2$ (SEQ ID NO: 35);
(Aib$^8$, Leu$^{27}$, β-Ala$^{35}$)hGLP-1(7-36)$NH_2$ (SEQ ID NO:36);
(Aib$^8$, Lys$^{33}$, β-Ala$^{35}$)hGLP-1(7-36)$NH_2$ (SEQ ID NO:37);
(Aib$^8$, Lys$^{18}$, Leu$^{27}$, β-Ala$^{35}$)hGLP-1(7-36)$NH_2$ (SEQ ID NO:38);

(Aib⁸, D-Arg³⁶)hGLP-1(7-36)NH₂ (SEQ ID NO:39);
(Aib⁸, β-Ala³⁵, D-Arg³⁷)hGLP-1(7-37)NH₂ (SEQ ID NO:40);
(Aib⁸,²⁷, β-Ala³⁵)hGLP-1(7-36)NH₂ (SEQ ID NO:41);
(Aib⁸,²⁷, β-Ala³⁵,³⁷, Arg³⁹)hGLP-1(7-38)NH₂ (SEQ ID NO:42);
(Aib⁸,²⁷, β-Ala³⁵,³⁷, Arg³⁸,³⁹)hGLP-1(7-39)NH₂(SEQ ID NO:43);
(Aib⁸, Lys¹⁸,²⁷, β-Ala³⁵)hGLP-1(7-36)NH₂ (SEQ ID NO:44);
(Aib⁸, Lys²⁷, β-Ala³⁵)hGLP-1 (7-36)NH₂ (SEQ ID NO:45);
(Aib⁸, β-Ala³⁵, Arg³⁸)hGLP-1(7-38)NH₂ (SEQ ID NO:46);
(Aib⁸, Arg²⁶,³⁴ Ala³⁵)hGLP-1(7-36)NH₂ (SEQ ID NO:47);
(Aib⁸, D-Arg³⁵)hGLP-1(7-36)NH₂ (SEQ ID NO:48);
(Aib⁸, β-Ala³⁵, Arg³⁷)hGLP-1(7-37)NH₂ (SEQ ID NO:49);
(Aib⁸, Phe³¹, β-Ala³⁵)hGLP-1(7-36)NH₂ (SEQ ID NO:50);
(Aib⁸,³⁵, Phe³¹)hGLP-1(7-36)NH₂ (SEQ ID NO:51);
(Aib⁸,³⁵, Nal³¹)hGLP-1(7-36)NH₂ (SEQ ID NO:52);
(Aib⁸,³⁵, Nal²⁸,³¹)hGLP-1 (7-36)NH₂ (SEQ ID NO:53);
(Aib⁸,³⁵, Arg²⁶,³⁴, Nal³¹)hGLP-1(7-36)NH₂ (SEQ ID NO:54);
(Aib⁸,³⁵ Arg²⁶,³⁴ Phe³¹)hGLP-1(7-36)NH₂(SEQ ID NO:55);
(Aib⁸,³⁵, Nal¹⁹,³¹)hGLP-1 (7-36)NH₂ (SEQ ID NO:56);
(Aib⁸,³⁵, Nal¹²,³¹)hGLP-1 (7-36)NH₂ (SEQ ID NO:57);
(Aib⁸,³⁵, Lys³⁶(Nᵝ-decanoyl))hGLP-1 (7-36)NH₂ (SEQ ID NO:58);
(Aib⁸,³⁵, Arg³⁴, Lys²⁶(Nᵋ-decanoyl))hGLP-1(7-36)NH₂ (SEQ ID NO:59);
(Aib⁸,³⁵, Arg²⁶,³⁴, Lys³⁶(Nᵋ-dodecanoyl))hGLP-1(7-36) NH₂ (SEQ ID NO:60);
(Aib⁸, β-Ala³⁵, Ser³⁷(O-decanoyl))hGLP-1(7-37)—NH₂ (SEQ ID NO:61);
(Aib⁸,²⁷, β-Ala³⁵,³⁷, Arg³⁸, Lys³⁹(Nᵋ-octanoyl))hGLP-1(7-39)NH₂ (SEQ ID NO:62);
(Aib⁸, Arg²⁶,³⁴, β-Ala³⁵, Lys³⁷(Nᵋ-octanoyl))hGLP-1(7-37) NH₂ (SEQ ID NO:63);
(Aib⁸, Arg²⁶,³⁴, β-Ala³⁵ Lys³⁷(Nᵋ-decanoyl))hGLP-1 (7-37) NH₂ (SEQ ID NO:64); or
(Aib⁸, Arg²⁶,³⁴, β-Ala³⁵, Lys³⁷(Nᵋ-tetradecanoyl))hGLP-1 (7-37)NH₂ (SEQ ID NO:65);
or a pharmaceutically acceptable salt thereof.

Another more preferred compound of formula (I) is each of the compounds that are specifically enumerated hereinbelow in the Examples section of the present disclosure, or a pharmaceutically acceptable salt thereof.

In another aspect, the present invention provides a pharmaceutical composition comprising an effective amount of a compound of formula (I) as defined hereinabove or a pharmaceutically acceptable salt thereof and a pharmaceutically acceptable carrier of diluent.

In yet another aspect, the present invention provides a method of eliciting an agonist effect from a GLP-1 receptor in a subject in need thereof which comprises administering to said subject an effective amount of a compound of formula (I) as defined hereinabove or a pharmaceutically acceptable salt thereof.

In a further aspect, the present invention provides a method of treating a disease selected from the group consisting of Type I diabetes, Type II diabetes, obesity, glucagonomas, secretory disorders of the airway, metabolic disorder, arthritis, osteoporosis, central nervous system disease, restenosis, neurodegenerative disease, renal failure, congestive heart failure, nephrotic syndrome, cirrhosis, pulmonary edema, hypertension, and disorders wherein the reduction of food intake is desired, in a subject in need thereof which comprises administering to said subject an effective amount of a compound of formula (I) as defined hereinabove or a pharmaceutically acceptable salt thereof. A preferred method of the immediately foregoing method is where the disease being treated is Type I diabetes or Type II diabetes.

With the exception of the N-terminal amino acid, all abbreviations (e.g. Ala) of amino acids in this disclosure stand for the structure of —NH—CH(R)—CO—, wherein R is the side chain of an amino acid (e.g., CH₃ for Ala). For the N-terminal amino acid, the abbreviation stands for the structure of (R²R³)—N—CH(R)—CO—, wherein R is a side chain of an amino acid and R² and R³ are as defined above, except when A⁷ is Ura, Paa or Pta, in which case R² and R³ are not present since Ura, Paa and Pta are considered here as des-amino amino acids. Amp, β-Nal, Nle, Cha. 3-Pal, 4-Pal and Aib are the abbreviations of the following α-amino acids: 4-amino-phenylalanine, β-(2-naphthyl)alanine, norleucine, cyclohexylalanine, β-(3-pyridinyl)alanine, β-(4-pyridinyl)alanine and α-aminoisobutyric acid, respectively. Other amino acid definitions are: Ura is urocanic acid; Pta is (4-pyridylthio) acetic acid; Paa is trans-3-(3-pyridyl) acrylic acid; Tma-His is N,N-tetramethylamidino-histidine; N-Me-Ala is N-methylalanine; N-Me-Gly is N-methyl-glycine; N-Me-Glu is N-methyl-glutamic acid; Tle is tert-butylglycine; Abu is α-aminobutyric acid; Tba is tert-butylalanine; Orn is ornithine; Aib is α-aminoisobutyric acid. β-Ala is P-alanine; Gaba is γ-aminobutyric acid; Ava is 5-aminovaleric acid; Ado is 12-aminododecanoic acid; Aic is 2-aminoindane-2-carboxylic acid; Aun is 11-aminoundecnoic acid; and Aec is 4-(2-aminoethyl)-1-carboxymethyl-piperazine, represented by the structure:

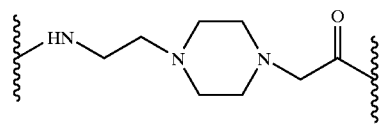

What is meant by Acc is an amino acid selected from the group of 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexanecarboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c). In the above formula, hydroxyalkyl, hydroxyphenylalkyl, and hydroxynaphthylalkyl may contain 1-4 hydroxy substituents. COX⁵ stands for —C=OX⁵. Examples of —C=OX⁵ include, but are not limited to, acetyl and phenylpropionyl.

What is meant by Lys(Nε-alkanoyl) is represented by the following structure:

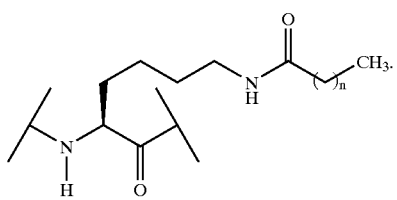

What is meant by Lys(Nε-alkylsulfonyl) is represented by the following structure

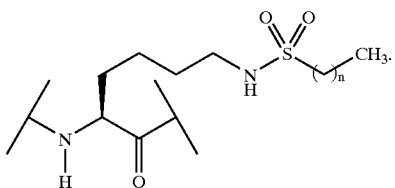

What is meant by Lys(N$_\epsilon$-(2-(4-alkyl-1-piperazine)-acetyl)) is represented by the following structure:

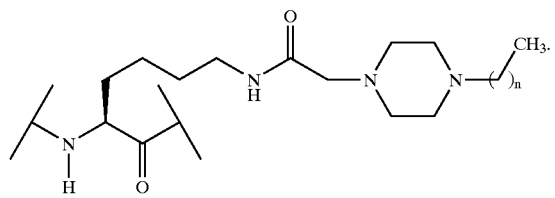

What is meant by Asp(1-(4-alkyl-piperazine)) is represented by the following structure:

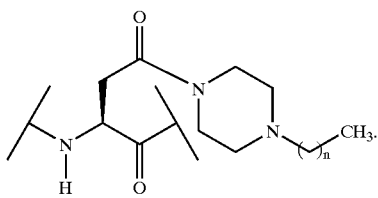

What is meant by Asp(1-alkylamino) is represented by the following structure:

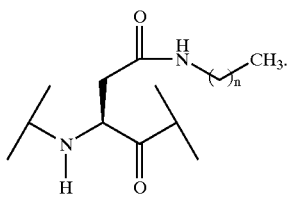

What is meant by Lys(N$_\epsilon$-Aec-alkanoyl) is represented by the structure:

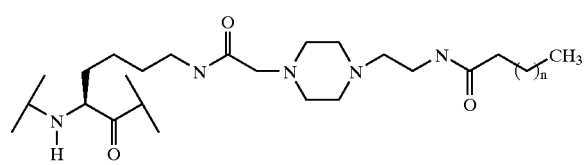

The variable n in the foregoing structures is 1–30. What is meant by Lys (Nε-ace-alkanoyl) is represented by the structure:

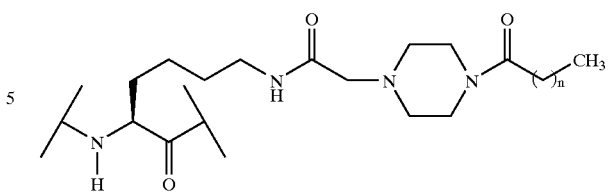

The full names for other abbreviations used herein are as follows: Boc for t-butyloxycarbonyl, HF for hydrogen fluoride, Fm for formyl, Xan for xantbyl, Bzl for benzyl, Tos for tosyl, DNP for 2,4-dinitrophenyl, DMF for dimethylformamide, DCM for dichloromethane, HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2CIZ for 2-chlorobenzyloxycarbonyl, 2BrZ for 2-bromobenzyloxycarbonyl, OcHex for O-cyclohexyl, Fmoc for 9-fluorenylmethoxycarbonyl, HOBt for N-hydroxybenzotriazole and PAM resin for 4-hydroxymethylphenylacetamidomethyl resin.

The term "halo" encompasses fluoro, chloro, bromo and iodo.

The term "($C_1$–$C_{30}$)hydrocarbon moiety" encompasses alkyl, alkenyl and alkynyl, and in the case of alkenyl and alkynyl there are $C_2$–$C_{30}$.

A peptide of this invention is also denoted herein by another format, e.g., (A5c$^8$)hGLP-1 (7-36)NH$_2$ (SEQ ID NO:66), with the substituted amino acids from the natural sequence placed between the set of parentheses (e.g., A5c$^8$ for Ala$^8$ in hGLP-1). The abbreviation GLP-1 means glucagon-like peptide-1; hGLP-1 means human glucagon-like peptide-1. The numbers between the parentheses refer to the number of amino acids present in the peptide (e.g., hGLP-1 (7-36) (SEQ ID NO:1) is amino acids 7 through 36 of the peptide sequence for human GLP-1). The sequence for hGLP-1(7-37) (SEQ ID NO:413) is listed in Mojsov, S., Int. J. Peptide Protein Res, 40, 1992, pp. 333–342. The designation "NH$_2$" in hGLP-1(7-36)NH$_2$ (SEQ ID NO:1) indicates that the C-terminus of the peptide is amidated. hGLP-1(7-36) (SEQ ID NO:1) means that the C-terminus is the free acid. In hGLP-1(7-38) (SEQ ID NO:414), residues in positions 37 and 38 are Gly and Arg, respectively.

DETAILED DESCRIPTION

The peptides of this invention can be prepared by standard solid phase peptide synthesis. See, e.g., Stewart, J. M., et al., Solid Phase Synthesis (Pierce Chemical Co., 2d ed. 1984). The substituents $R^2$ and $R^3$ of the above generic formula may be attached to the free amine of the N-terminal amino acid by standard methods known in the art. For example, alkyl groups, e.g., ($C_1$–$C_{30}$)alkyl, may be attached using reductive alkylation. Hydroxylalkyl groups, e.g., ($C_1$–$C_{30}$) hydroxyalkyl, may also be attached using reductive alkylation wherein the free hydroxy group is protected with a t-butyl ester. Acyl groups, e.g., COE$^1$, may be attached by coupling the free acid, e.g., E$^1$COOH, to the free amine of the N-terminal amino acid by mixing the completed resin with 3 molar equivalents of both the free acid and diisopropylcarbodiimide in methylene chloride for one hour. If the free acid contains a free hydroxy group, e.g., p-hydroxyphenylpropionic acid, then the coupling should be performed with an additional 3 molar equivalents of HOBT.

When $R^1$ is NH—$X^2$—CH$_2$—CONH$_2$, (i.e., $Z^0$=CONH$_2$), the synthesis of the peptide starts with Boc- HN—X²—CH₂—COOH which is coupled to the MBHA resin. If R¹ is NH—X²—CH₂—COOH, (i.e., Z⁰═COOH) the synthesis of the peptide starts with Boc-HN—X²—CH₂—COOH which is coupled to the PAM resin. For this particular step, 4 molar equivalents of Boc-HN—X²—COOH, HBTU and HOBt and 10 molar equivalents of DIEA are used. The coupling time is about 8 hours.

The protected amino acid —(N-tert-butoxycarbonyl-amino)-1-cyclohexane-carboxylic acid (Boc-A6c-OH) was synthesized as follows. 19.1 g (0.133 mol) of 1-amino-1-cyclohexanecarboxylic acid (Acros Organics, Fisher Scientific, Pittsburgh, Pa.) was dissolved in 200 ml of dioxane and 100 ml of water. To it was added 67 ml of 2N NaOH. The solution was cooled in an ice-water bath. 32.0 g (0.147 mol) of di-tert-butyl-dicarbonate was added to this solution. The reaction mixture was stirred overnight at room temperature. Dioxane was then removed under reduced pressure. 200 ml of ethyl acetate was added to the remaining aqueous solution. The mixture was cooled in an ice-water bath. The pH of the aqueous later was adjusted to about 3 by adding 4N HCl. The organic layer was separated. The aqueous later was extracted with ethyl acetate (1×100 ml). The two organic layers were combined and washed with water (2×150 ml), dried over anhydrous $MgSO_4$, filtered, and concentrated to dryness under reduced pressure. The residue was recrystallized in ethyl acetate/hexanes. 9.2 g of the pure product was obtained. 29% yield.

Boc-A5c-OH was synthesized in an analogous manner to that of Boc-A6c-OH. Other protected Acc amino acids can be prepared in an analogous manner by a person of ordinary skill in the art as enabled by the teachings herein.

In the synthesis of a GLP-1 analogue of this invention containing A5c, A6c and/or Aib, the coupling time is 2 hrs. for these residues and the residue immediately following them. For the synthesis of (Tma-His⁷)hGLP-1(7-36)NH₂ (SEQ ID NO:67), HBTU (2 mmol) and DIEA (1.0 ml) in 4 ml DMF are used to react with the N-terminal free amine of the peptide-resin in the last coupling reaction; the coupling time is about 2 hours.

The substituents $R^2$ and $R^3$ of the above generic formula can be attached to the free amine of the N-terminal amino acid by standard methods known in the art. For example, alkyl groups, e.g., $(C_1-C_{30})$alkyl, can be attached using reductive alkylation. Hydroxyalkyl groups, e.g., $(C_1-C_{30})$ hydroxyalkyl, can also be attached using reductive alkylation wherein the free hydroxy group is protected with a t-butyl ester. Acyl groups, e.g., $COX^1$, can be attached by coupling the free acid, e.g., $X^1COOH$, to the free amine of the N-terminal amino acid by mixing the completed resin with 3 molar equivalents of both the free acid and diisopropylcarbodiimide in methylene chloride for about one hour. If the free acid contains a free hydroxy group, e.g., p-hydroxyphenylpropionic acid, then the coupling should be performed with an additional 3 molar equivalents of HOBT.

A compound of the present invention can be tested for activity as a GLP-1 binding compound according to the following procedure.

Cell Culture:

RIN 5F rat insulinoma cells (ATCC-# CRL-2058, American Type Culture Collection, Manassas, Va.), expressing the GLP-1 receptor, were cultured in Dulbecco's modified Eagle's medium (DMEM) containing 10% fetal calf serum, and maintained at about 37° C. in a humidified atmosphere of 5% $CO_2$/95% air.

Radioligand Binding:

Membranes were prepared for radioligand binding studies by homogenization of the RIN cells in 20 ml of ice-cold 50 mM Tris-HCl with a Brinkman Polytron (Westbury, N.Y.) (setting 6. 15 sec). The homogenates were washed twice by centrifugation (39,000 g/10 min), and the final pellets were resuspended in 50 mM Tris-HCl, containing 2.5 mM $MgCl_2$, 0.1 mg/ml bacitracin (Sigma Chemical, St. Louis, Mo.), and 0.1% BSA. For assay, aliquots (0.4 ml) were incubated with 0.05 nM ($^{125}$I)GLP-1(7-36) (SEQ ID NO:415) (~2200 Ci/mmol, New England Nuclear, Boston, Mass.), with and without 0.05 ml of unlabeled competing test peptides. After a 100 min incubation (25° C.), the bound ($^{125}$)GLP-1(7-36) (SEQ ID NO:415) was separated from the free by rapid filtration though GF/C filters (Brandel, Gaithersburg, Md.), which had been previously soaked in 0.5% polyethyleneimine. The filters were then washed three times with 5 ml aliquots of ice-cold 50 mM Tris-HCl, and the bound radioactivity trapped on the filters was counted by gamma spectrometry (Wallac LKB, Gaithersburg, Md.). Specific binding was defined as the total ($^{125}$I)GLP-1(7-36) (SEQ ID NO:415) bound minus that bound in the presence of 1000 nM GLP-1(7-36) (SEQ ID NO:1) (Bachem, Torrence, Calif.).

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs., (2) 0.25N acetic acid aqueous solution for 0.5 hrs. and (3) a linear gradient (20% to 100% of solution B over 30 min.) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

As is well known to those skilled in the art, the known and potential uses of GLP-1 is varied and multitudinous (See, Todd, J. F., et al., Clinical Science, 1998, 95, pp. 325–329: and Todd, J. F. et al., European Journal of Clinical Investigation, 1997, 27, pp.533–536). Thus, the administration of the compounds of this invention for purposes of eliciting an agonist effect can have the same effects and uses as GLP-1 itself. These varied uses of GLP-1 may be summarized as follows, treatment of: Type I diabetes, Type II diabetes, obesity, glucagonomas, secretory disorders of the airway, metabolic disorder, arthritis, osteoporosis, central nervous system diseases, restenosis, neurodegenerative diseases, renal failure, congestive heart failure, nephrotic syndrome, cirrhosis, pulmonary edema, hypertension, and disorders wherein the reduction of food intake is desired. GLP-1 analogous of the present invention that elicit an antagonist effect from a subject can be used for treating the following: hypoglycemia and malabsorption syndrome associated with gastroectomy or small bowel resection.

Accordingly, the present invention includes within its scope pharmaceutical compositions comprising, as an active ingredient, at least one of the compounds of formula (I) in association with a pharmaceutically acceptable carrier.

The dosage of active ingredient in the compositions of this invention may be varied: however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. U.S. application Ser. No. 09/015,394 (now abandoned) filed Jan. 29, 1998, teaches absorbable sustained release compositions of a bioactive agent. U.S. Application No. 09/121,653 (now abandoned) filed Jul. 23, 1998, teaches a process for making microparticles comprising a therapeutic agent such as a peptide in an oil-in-water process. U.S. application Ser. No. 09/131,472 (now abandoned) filed Aug. 10, 1998, teaches complexes comprising a therapeutic agent such as a peptide and a phosphorylated polymer. U.S. Application No. 09/184,413 (now abandoned) filed Nov. 2, 1998, teaches complexes comprising a therapeutic agent such as a peptide and a polymer bearing a non-polymerizable lactone. The teachings of the foregoing patents and applications are incorporated herein by reference.

Unless defined otherwise, all technical and scientific terms used herein have the same meaning as commonly understood by one of ordinary skill in the art to which this invention belongs. Also, all publications, patent applications, patents and other references mentioned herein are incorporated by reference.

The following examples describe synthetic methods for making a peptide of this invention, which methods are well-known to those skilled in the art. Other methods are also known to those skilled in the art. The examples are provided for the purpose of illustration and is not meant to limit the scope of the present invention in any manner.

Boc-βAla-OH, Boc-D-Arg(Tos)-OH and Boc-D-Asp (OcHex) were purchased from Nova Biochem, San Diego, Calif. Boc-Aun-OH was purchased from Bachem. King of Prussia, Pa. Boc-Ava-OH and Boc-Ado-OH were purchased from Chem-Implex International, Wood Dale, Ill. Boc-Nal-OH was purchased from Synthetech, Inc. Albany, Oreg.

EXAMPLE 1

(Aib$^{8,35}$)hGLP-1(7-36)NH$_2$ (SEQ ID NO:2)

The title peptide was synthesized on an Applied Biosystems (Foster City, Calif.) model 430A peptide synthesizer which was modified to do accelerated Boc-chemistry solid phase peptide synthesis. See Schnolzer, et al., Int. J. Peptide Protein Res., 90:180 (1992). 4-methylbenz-hydrylamine (MBHA) resin (Peninsula, Belmont, Calif.) with the substitution of 0.91 mmol/g was used. The Boc amino acids (Bachem, Calif., Torrance, Calif.; Nova Biochem., LaJolla, Calif.) were used with the following side chain protection: Boc-Ala-OH, Boc-Arg(Tos)-OH, Boc-Asp(OcHex)-OH, Boc-Tyr(2BrZ)-OH, Boc-His(DNP)—OH, Boc-Val-OH, Boc-Leu-OH, Boc-Gly-OH, Boc-Gln-OH. Boc-Ile-OH, Boc-Lys(2ClZ)-OH, Boc-Thr(Bzl)-OH, Boc-Ser(Bzl)-OH, Boc-Phe-OH, Boc-Aib-OH, Boc-Glu(OcHex)-OH and Boc-Trp(Fm)-OH. The synthesis was carried out on a 0.20 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 min. except for the Boc-Aib-OH residues and the following residues, Boc-Lys(2ClZ)-OH and Boc-His(DNP)—OH wherein the coupling times were 2 hours.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. After neutralization of the peptide-resin with 10% DIEA in DMF (1×1 min), the formyl group on the side chain of Trp was removed by treatment with a a solution of 15% ethanolamine/15% water/70% DMF for 2×30 min. The peptide-resin was washed with DMF and DCM and dried under reduced pressure. The final cleavage was done by stirring the peptide-resin in 10 mL of HF containing 1 mL of anisole and dithiothreitol (24 mg) at 0° C. for 75 min. HF was removed by a flow of nitrogen. The residue was washed with ether (6×10 mL) and extracted with 4N HOAc (6×10 mL).

The peptide mixture in the aqueous extract was purified on reverse-phase preparative high pressure liquid chromatography (HPLC) using a reverse phase VYDAC(& $C_{18}$ column (Nest Group, Southborough, Mass.). The column was eluted with a linear gradient (20% to 50% of solution B over 105 min.) at a flow rate of 10 mL/min (Solution A=water containing 0.1% TFA; Solution B=acetonitrile containing 0.1% of FTA). Fractions were collected and checked on analytical HPLC. Those containing pure product were combined and lyophilized to dryness. 135 mg of a white solid was obtained. Purity was 98.6% based on analytical HPLC analysis. Electro-spray mass spectrometer (MS (ES))S analysis gave the molecular weight at 3339.7 (in agreement with the calculated molecular weight of 3339.7).

EXAMPLE 2

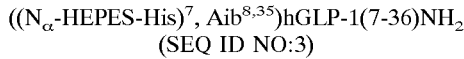

$((N_\alpha\text{-HEPES-His})^7, \text{Aib}^{8,35})\text{hGLP-1}(7\text{-}36)\text{NH}_2$
(SEQ ID NO:3)

The title compound (HEPES is (4-(2-hydroxyethyl)-1-piperazine-ethanesulfonic acid)) can be synthesized as follows: after assembly of the peptide $(\text{Aib}^{8,35})\text{hGLP-1}(7\text{-}36)\text{NH}_2$ (SEQ ID NO:2) on MBHA resin (0.20 mmol) according to the procedure of Example 1, the peptide-resin is treated with 100% TFA (2×2 min.) and washed with DMF and DCM. The resin is then neutralized with 10% DIEA in DMF for 2 min. After washing with DMF and DCM, the resin is treated with 0.23 mmol of 2-chloro-1-ethanesulfonyl chloride and 0.7 mmol of DIEA in DMF for about 1 hour. The resin is washed with DMF and DCM and treated with 1.2 mmol of 2-hydroxyethylpiperazine for about 2 hours. The resin is washed with DMF and DCM and treated with different reagents ((1) 20% mercaptoethanol/10% DIEA in DMF and (2) 15% ethanolamile/15% water/70% DMF) to remove the DNP group on the His side chain and formyl group on the Trp side chain as described above before the final HF cleavage of the peptide from the resin.

EXAMPLE 3

$((N_\alpha\text{-HEPA-His})^7, \text{Aib}^{8,35})\text{hGLP-1}(7\text{-}36)\text{NH}_2$ (SEQ ID NO:4)

The title compound (HEPA is (4-(2-hydroxyethyl)-1-piperazineacetyl)) can be made substantially according to the procedure described in Example 2 for making $((N_\alpha\text{—HEPES-His})^7, \text{Aib}^{8,35})\text{hGLP-1}(7\text{-}36)\text{NH}_2$ (SEQ ID NO:3) except that 2-bromoacetic anhydride is used in place of 2chloro-1-ethanesulfonyl chloride.

EXAMPLE 4

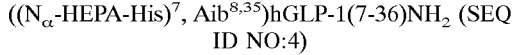

$(\text{Aib}^8, \beta\text{-Ala}^{35})\text{hGLP-1}(7\text{-}36)\text{NH}_2$ (SEQ ID NO:5)

The title compound was synthesized substantially according to the procedure described for Example 1 using the appropriate protected amino acids. MS (ES)=3325.7, calculated MW 3325.8, purity=99%, yield=85 mg.

The synthesis of other compounds of the present invention can be accomplished in substantially the same manner as the procedure described for the synthesis of $(\text{Aib}^{8,35})$ hGLP-1(7-36)NH$_2$ (SEQ ID NO:2) in Example 1 above, but using the appropriate protected amino acids depending on the desired peptide.

EXAMPLE 5

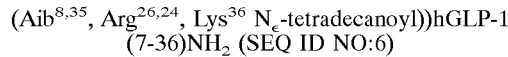

$(\text{Aib}^{8,35}, \text{Arg}^{26,24}, \text{Lys}^{36} \text{ N}_\epsilon\text{-tetradecanoyl}))\text{hGLP-1}$
(7-36)NH$_2$ (SEQ ID NO:6)

The Boc amino acids used were the same as those in the synthesis of $(\text{Aib}^{8,35})\text{hGLP-1}(7\text{-}36)\text{NH}_2$ (SEQ ID NO:2) described in Example 1 except that Fmoc-Lys(Boc)-OH was used in this example. The first amino acid residue was coupled to the resin manually on a shaker. 2.5 mmol of Fmoc-Lys(Boc)-OH was dissolved in 4 mL of 0.5N HBTU in DMF. To the solution was added 1 mL of DIEA. The mixture was shaken for about 2 min. To the solution was then added 0.2 mmol of MBHA resin (substitution=0.91 mmol/g). The mixture was shaken for about 1 hr. The resin was washed with DMF and treated with 100% TFA for 2×2 min to remove the Boc protecting group. The resin was washed with DMF. Myristic acid (2.5 mmol) was pre-activated with HBTU (2.0 mmol) and DIEA (1.0 mL) in 4 mL of DMF for 2 min and was coupled to the Fmoc-Lys-resin. The coupling time was about 1 hr. The resin was washed with DMF and treated with 25% piperidine in DMF for 2×20 min to remove the Fmoc protecting group. The resin was washed with DMF and transferred to the reaction vessel of the peptide synthesizer. The following steps synthesis and purification procedures for the peptide were the same as those in the synthesis of $(\text{Aib}^{8,35})\text{hGLP-1}(7\text{-}36)\text{NH}_2$ (SEQ ID NO:2) in Example 1.43.1 mg of the title compound were obtained as a white solid. Purity was 98% based on analytical HPLC analysis. Electro-spray mass spectrometer analysis gave the molecular weight at 3577.7 in agreement with the calculated molecular weight 3578.7.

EXAMPLE 6-8

Examples 6–8 were synthesized substantially according to the procedure described for Example 5 using the appropriate protected amino acid and the appropriate acid in place of the Myristic acid used in Example 5.
Example 6: $(\text{Aib}^{8,35}, \text{Arg}^{26}, \text{Lys}^{34}(\text{N}_\epsilon\text{-tetradecanoyl}))$ hGLP-1 (7-36)NH$_2$ (SEQ ID NO:7); Yield=89.6 mg; MS(ES)=3577.2, Calculated MW=3578.7; Purity 96%.
Example 7: (Aib $^{8,35,37}$, Arg$^{26,34}$, Lys$^{36}$(N$_\epsilon$-tetradecanoyl)) hGLP-1(7-38)NH$_2$ (SEQ ID NO:8); Yield=63.3 mg; MS(ES)=3818.7; Calculated MW=3819.5; Purity 96%.
Example 8: (Aib$^{8,35}$, Arg$^{26,34}$, Lys$^{36}$(N$_\epsilon$-decanoyl))hGLP-1 (7-36)NH$_2$ (SEQ ID NO:9); Yield=57.4 mg; MS(ES)= 3521.5; Calculated MW=3522.7; Purity 98%; Acid= decanoic acid.

The syntheses of the other compounds of the present invention containing Lys(N$_\epsilon$-alkanoyl) residue can be carried out in an analogous manner to the procedure described for Example 5, (Aib$^{8,35}$, Arg$^{26,34}$, Lys$^{36}$(N$_\epsilon$-tetradecanoyl)) hGLP-1 (7-36)NH$_2$ (SEQ ID NO:6). Fmoc-Lys(Boc)-OH amino acid is used for the residue of Lys(N$_\epsilon$-alkanoyl) in the peptide, while Boc-Lys(2ClZ)-OH amino acid is used for the residue of Lys. If the Lys(N$_\epsilon$-alkanoyl) residue is not at the C-terminus, the peptide fragment immediately prior to the Lys(N$_\epsilon$-alkanoyl) residue is assembled on the resin on the peptide synthetizer first. The appropriate acid corresponding to the desired alkanoyl can be purchased from Aldrich Chemical Co., Inc. Milwaukee, Wis., USA, e.g., octanoic acid, decanoic acid, lauric acid and palmitic acid.

EXAMPLE 9

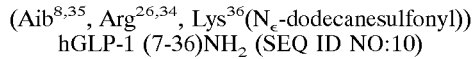

$(\text{Aib}^{8,35}, \text{Arg}^{26,34}, \text{Lys}^{36}(\text{N}_\epsilon\text{-dodecanesulfonyl}))$
hGLP-1 (7-36)NH$_2$ (SEQ ID NO:10)

The Boc amino acids to be used in this synthesis are the same as those used in the synthesis of Example 5. The first amino acid residue is coupled to the resin manually on a shaker. 2.5 mmol of Fmoc-Lys(Boc)-OH is dissolved in 4 mL of 0.5N HBTU in DMF. To the solution is added 1 mL of DIEA. The mixture is shaken for about 2 min. To the solution is then added 0.2 mmol of MBHA resin (substitution=0.91 mmol/g). The mixture is shaken for about 1 hr. The resin is washed with DMF and treated with 100% TFA for 2×2 min to remove the Boc protecting group. The resin is washed with DMF and to it is added 0.25 mmol of 1-dodecanesulfonyl chloride in 4 mL of DMF and 1 mL of DIEA. The mixture is shaken for about 2 hrs. The resin is washed with DMF and treated with 25% piperidine in DMF for 2×20 min to remove the Fmoc protecting group. The resin is washed with DMF and transferred to the reaction vessel of the peptide synthesizer. The synthesis of the rest of the peptide and purification procedures are the same as those described in Example 1.

The syntheses of other compounds of the present invention containing Lys($N_\epsilon$-alkylsulfonyl) residue can be carried out in an analogous manner to the procedure described in Example 9. Fmoc-Lys(Boc)-OH amino acid is used for the residue of Lys($N_\epsilon$-alkylsulfonyl) in the peptide, while Boc-Lys(2CIZ)-OH amino acid is used for the residue of Lys. If the Lys($N_\epsilon$-alkylsulfonyl) residue is not at the C-terminus, the peptide fragment immediately prior to the Lys($N_\epsilon$-alkylsulfonyl) residue is assembled on the resin on the peptide synthesizer first. The appropriate akylsulfonyl chloride can be obtained from Lancaster Synthesis Inc., Windham, N.H., USA, e.g., 1-octanesulfonyl chloride, 1-decanesulfonyl chloride, 1-dodecanesulfonyl chloride, 1-hexadecanesulfonyl chloride and 1-octadecylsulfonyl chloride.

EXAMPLE 10

(Aib$^{8,35}$, Arg$^{26,34}$, Lys$^{36}$($N_\epsilon$-(2-(4-tetradecyl-1-piperazine)-acetyl)))hGLP-1(7-36)N H$_2$ (SEQ ID NO:11)

The Boc amino acids to be used for this example are the same as those used in the synthesis of Example 5. The first amino acid residue is coupled to the resin manually on a shaker. 2.5 mmol of Fmoc-Lys(Boc)-OH is dissolved in 4 mL of 0.5N HBTU in DMF. To the solution is added 1 mL of DIEA. The mixture is shaken for about 2 min. To the solution is then added 0.2 mmol of MBHA (substitution= 0.91 mmol/g). The mixture is shaken for about 1 hr. The resin is washed with DMF and treated with 100% TFA for 2×2 min to remove the Boc protecting group. The resin is washed with DMF. The 2-bromoacetic acid (2.5 mmol) is pre-activated with HBTU (2.0 mmol) and DIEA (1 mL) in 4 mL of DMF for about 2 min and is added to the resin. The mixture is shaken for about 10 min and washed with DMF. The resin is then treated with 1.2 mmol of piperazine in 4 mL of DMF for about 2 hrs. The resin is washed with DMF and treated with 2 mmol of 1-iodotetradecane for about 4 hrs. After washing with DMF, the resin is treated with 3 mmol of acetic anhydride and 1 mL of DIEA in 4 ml of DMF for about 0.5 hr. The resin is washed with DMF and treated with 25% piperidine in DMF for 2×20 min. The resin is washed with DMF and transferred to the reaction vessel of the peptide synthesizer to continue the synthesis. The remaining synthesis and purification procedures for the peptide are the same as the procedures described for Example 1.

The syntheses of other compounds of the present invention containing Lys(N-(2-(4-alkyl-1-piperazine)-acetyl)) residue are carried out in an analogous manner as the procedure described for the synthesis of Example 10. Fmoc-Lys(Boc)-OH amino acid is used for the residue of Lys(N-(2-(4-alkyl-1-piperazine)-acetyl)) in the peptide, while Boc-Lys(2CIZ)-OH amino acid is used for the residue of Lys. The corresponding iodoalkane is used for the residue of Lys($N_\epsilon$-(2-(4-alky-1-piperazine)-acetyl)) during the alkylation step. If the Lys(N-(2-(4-alkyl-1-piperazine)-acetyl)) residue is not at the C-terminus, the peptide fragment immediately prior to the Lys($N_\epsilon$-(2-(4-alkyl-1-piperazine)-acetyl)) residue is assembled on the resin on the peptide synthesizer first.

EXAMPLE 11

(Aib$^{8,35}$, Arg$^{26,34}$ Asp$^{36}$ (1-(4-tetradecyl-piperazine)))hGLP-1(7-36)NH$_2$ (SEQ ID NO:12)

The Boc amino acids to be used in this example are the same as the amino acids used in synthesis of Example 5 except Fmoc-Asp(O-tBu)-OH is used at position 36. The first amino acid residue is coupled to the resin manually on a shaker. 2.5 mmol of Fmoc-Asp(O-tBu)-OH is dissolved in 4 mL of 0.5N HBTU in DMF. To the solution is added 1 mL of DIEA. The mixture is shaken for about 2 min. To the solution is then added 0.2 mmol of MBHA (substitution= 0.91 mmol/g) resin. The mixture is shaken for about 1 hr. The resin is washed with DMF and treated with 100% TFA for 2×15 min to remove the tBu protecting group. The resin is washed with DMF and is treated with HBTU (0.6 mmol) and DIEA (1 mL) in 4 mL of DMF for about 15 min. 0.6 mmol of piperazine is added to the reaction mixture and the mixture is shaken for about 1 hr. The resin is washed with DMF and treated with 3 mmol of 1-iodotetradecane for about 4 hrs. After washing with DMF, the resin is treated with 3 mmol of acetic anhydride and 1 mL of DIEA in 4 mL of DMF for about 0.5 hr. The resin is washed with DMF and treated with 25% piperidine in DMF for 2×20 min to remove the Fmoc protecting group. The resin is washed with DMF and transferred to the reaction vessel of the peptide synthesizer to continue the synthesis. The remaining synthesis and purification procedures for the peptide are the same as those for the synthesis of Example 1.

The syntheses of other compounds of the present invention comprising Asp(1-(4-alkylpiperazine)) or Glu(1-(4-alkylpiperazine)) residue are carried out in an analogous manner as the procedure described for the synthesis of Example 11. Fmoc-Asp(O-tBu)-OH or Fmoc-Glu(O-tBu)-OH amino acid is used for the residue of Asp(1-(4-alkylpiperazine)) or Glu(1-(4-alkylpiperazine)) in the peptide, while Boc-Asp(OcHex)-OH or Boc-Glu(OcHex)-OH amino acid is used for the residue of Asp or Glu. The corresponding iodoalkane is used for the residue of Lys(Ne (2-(4-alkyl-1-piperazine)-acetyl)) during the alkylation step. If the Asp(1-(4-alkylpiperazine)) or Glu(1-(4-alkylpiperazine)) residue is not at the C-terminus, the peptide fragment immediately prior to the Asp(1-(4-alkylpiperazine)) or Glu(1-(4-alkylpiperazine)) residue is assembled on the resin on the peptide synthesizer first.

EXAMPLE 12

(Aib$^{8,35}$, Arg$^{26,34}$, Asp$^{36}$(1-tetradecylamino))hGLP-1(7-36)NH$_2$ (SEQ ID NO:13)

The Boc amino acids to be used for this example are the same as those used in Example 5. The first amino acid residue is coupled to the resin manually on a shaker. 2.5 mmol of Fmoc-Asp(O-tBu)-OH is dissolved in 4 mL of 0.5N HBTU in DMF. To the solution is added 1 mL of DIEA. The mixture is shaken for about 2 min. To the solution is then added 0.2 mmol of MBHA (substitution= 0.91 mmol/g) resin. The mixture is shaken for about 1 hr. The resin is washed with DMF and treated with 100% TFA for 2×15 min to remove the t-Bu protecting group. The resin is washed with DMF and is treated with HBTU (0.6 mmol) and DIEA (1 mL)in 4 mL of DMF for about 15 min. 0.6 mmol of 1-tetradecaneamine is added to the reaction mixture and the mixture is shaken for about 1 hr. The resin is washed with DMF and treated with 25% piperidine in DMF for 2×20 min to remove the Fmoc protecting group. The resin is washed with DMF and transferred to the reaction vessel of the peptide synthesizer to continue the synthesis. The remaining synthesis and purification procedures for the peptide of this example are the same as those described for the synthesis of Example 1.

The syntheses of other compounds of the present invention containing Asp(1-alkylamino) or Glu(1-alkylamino) residue are carried out in an analogous manner as described for the synthesis of Example 12. Fmoc-Asp(O-tBu)-OH or Fmoc-Glu(O-tBu)-OH amino acid is used for the residue of Asp(1-alkylamino) or Glu(1-alkylamino), respectively, in the peptide, while Boc-Asp(OcHex)-OH or Boc-Glu (OcHex)-OH amino acid is used for the residue of Asp or Glu, respectively. If the Asp(1-alkylamino) or Glu(1-alkylamino) residue is not at the C-terminus, the peptide fragment immediately prior to the Asp(1-alkylamino) or Glu(1-alkylamino) residue is assembled on the resin on the peptide synthesizer first.

EXAMPLE 13

(Aib$^{8,35}$, Arg$^{26,34}$, Lys$^{36}$(N$_\epsilon$-tetradecanoyl), β-Ala$^{37}$) hGLP-1(7-37)—OH (SEQ ID NO:14)

The Boc amino acids used are the same as those in the synthesis of (Aib$^{8,35}$, Arg$^{26,34}$, Lys$^{36}$(N$_\epsilon$-tetradecanoyl)) hGLP-1(7-36)NH$_2$ (SEQ ID NO:6) (Example 5). 270 mg of Boc-β-Ala-PAM resin (Novabiochem, San Diego, Calif., substitution=0.74 mmol/g) was used. The Bio protecting group on Boc-β-Ala-PAM resin was deblocked on a shaker with 100% TFA for 2×2 min first. The remainder of the synthesis and purification procedures were the same as that in Example 5. 83.0 mg of the title peptide was obtained as white solid. Purity was 99% based oil analytical HPLC analysis. Electro-spray mass spectrometer analysis gave the molecular weight at 3650.5 in agreement with the calculated weight 3650.8.

EXAMPLE 14

(Aib$^{8,35}$, Arg$^{26,34}$, Lys$^{36}$(N$_\epsilon$-tetradecanoyl))hGLP-1 (7-36)—OH (SEQ ID NO:15)

The Boc amino acids to be used are the same as those in the synthesis of (Aib $^{8,35}$, Arg$^{26,34}$, Lys$^{36}$ N$_\epsilon$-tetradecanoyl)) hGLP-1(7-36)NH$_2$ (SEQ ID NO:6) (Example 5). Fmoc-Lys (Boc)-OH (2.5 mmol) is pre-activated with HBTU (2.0 mmol), HOBt (2.0 mmol) and DIEA (2.5 ml) in DMF (4 ml) for about 2 min. This amino acid is coupled to 235 mg of PAM resin (Chem-Impex, Wood Dale, Ill.; substitution=0.85 mmol/g) manually on a shaker. The coupling time is about 8 hrs. The remainder of the synthesis and purification procedures are the same as those in Example 5. Electro-spray mass spectrometer analysis gave the molecular weight It 3579.15 in agreement with the calculated weight 3579.5.

The synthesis of other analogs of hGLP-1 (7-36)—OH (SEQ ID NO:1), hGLP-1(7-37)—OH (SEQ ID NO:413) and hGLP-1(7-38)—OH (SEQ ID NO:414) of the instant invention which contain Lys(N$_\epsilon$(alkanoyl) residue can be carried out in an analogous manner according to the procedure described for the synthesis of Example 14. Fmoc-Lys(Boc)-OH amino acid is used for the residue of Lys(N$_\epsilon$(alkanoyl) in the peptide, while Boc-Lys(2ClZ)-OH amino acid is used for the residue of Lys.

EXAMPLE 366

(Aib$^8$, β-Ala$^{35}$, Aec$^{37}$)hGLP-1(7-37)NH$_2$ (SEQ ID NO:68)

A mixture of MBHA resin (0.2 mmol, substitution=0.91 mmol/g), Fmoc-Aec-OH (0.40g, 0.829 mmol), HBTU (1.5 mL (0.5M in DMF) and DIEA (0.5 mL) in a reaction vessel was shaken on a shaker for 4h at room temperature. The resin was then washed with DMF and treated with 25% piperidine in DMF for 2×20 min. The resin was washed with DMF and DCM and transferred to the reaction vessel of the peptide synthesizer to continue the assembly of the rest of the peptide according the procedure described for Example 1. The purification procedure was also the same as the one described in Example 1. Electro-spry mass spectrometer analysis gave the molecular weight at 3494.8 in agreement with the calculated molecular weight 3494.99.

Purity 93%; Yield 79.1 mg.

EXAMPLE 367

(Aib$^8$, β-Ala$^{35}$, Aec$^{37,38}$)hGLP-1(7-38)NH$_2$ (SEQ ID NO:69)

Example 367 was synthesized substantially according to the procedure described for Example 366. MS(ES)=3551.7, calculated MW=3552.04; Purity 97%; Yield 97.4 mg.

EXAMPLE 368

(Aib$^8$, β-Ala$^{35}$, Aec$^{37,38}$) hGLP-1(7-38)NH$_2$ (SEQ ID NO:70)

A mixture of MBHA resin (0.2 mmol, substitution=0.91 mmol/g), Fmoc-Aec-OH (0.289g, 0.6 mmol), HBTU (1.12 mL @ 0.5M in DMF) and DIEA (0.4 mL) in a reaction vessel was shaken on a shaker for 2h at room temperature. The resin was then washed with DMF and treated with 30% piperidine in DMF for 2×5 min. The resin as washed with DMF. To the reaction vessel were added Fmoc-Aec-OH (0.289 g, 0.6 mmol), HBTU (1.12 mL @ 0.5M in DMF) and DIEA (0.4 mL). The mixture was shaken at room temperature for 2 h. The resin was washed with DMF and treated with 30% piperidine in DMF for 2×15 min. The resin was washed with DMF and DCM and transferred to the reaction vessel of the peptide synthesizer to continue the assembly of the rest of the peptide according the procedure described for Example 1. The purification procedure was also the same as the one described in Example 1. Electro-spry, mass spectrometer analysis gave the molecular weight at 3663.9 in agreement with the calculated molecular weight 3664.26. Purity 100%; Yield 75.3 mg.

EXAMPLE 369

(Aib$^8$, Arg$^{26,34}$, β-Ala$^{35}$, Lys$^{36}$(N$^\epsilon$-Aec-decanoyl)) hGLP-1(7-36)NH$_2$ (SEQ ID NO:25)

A mixture of MBHA resin (0.2 mmol, substitution=0.91 mmol/g), Boc-Lys(Fmoc)-OH (1.17 g, 2.5 mmol), HBTU (4 mL @ 0.5M in DMF) and DIEA (1 mL) in a reaction vessel was shaken on a shaker at room temperature for 10 min. The resin was washed with DMF and treated with 25% piperidine in DMF for 2×15 min. The resin was washed with DMF. To the reaction vessel were added Fmoc-Aec-OH (0.289 g, 0.6 mmol), HBTU (1.12 mL @ 0.5M in DMF) and DIEA (0.4 mL). The mixture was shaken at room temperature for 10 min. The resin was washed with DMF and treated with 30% piperidine in DMF for 2×1 5 min. The resin was washed with DMF and treated with a mixture of decanoic acid (431 mg, 2.5 mmol), HBTU (4 mL @ (0.5M in DMF) and DIEA (1 mL) for 10 min. The resin was washed with DMF and treated with 100% TFA for 2×2 min. The resin was washed with DMF and DCM and transferred to the reaction vessel of the peptide synthesizer to continue the assembly of the rest of the peptide according the procedure described for Example 1. The purification procedure was also the same as the one described in Example 1. Elecro-spry mass spectrometer analysis gave the molecular weight at 3677.0 in agreement with the calculated molecular weight 3677.25. Purity 97.6%; Yield 44.1 mg.

The following examples can be made according to the appropriate procedures described hereinabove.

Example 15: (Aib$^{35}$)hGLP-1(7-36)NH$_2$ (SEQ ID NO:71)
Example 16: (β-Ala$^{35}$)hGLP-1(7-36)NH$_2$ (SEQ ID NO:72)
Example 17: ((N$^α$-Me-His)$^7$, Aib$^{8,35}$)hGLP-1(7-36)NH$_2$ (SEQ ID NO:73)
Example 18: ((N$^α$-Me-His)$^7$, Aib$^8$, β-Ala$^{35}$)hGLP-1(7-36)NH$_2$ (SEQ ID NO:74)
Example 19: ((N$^α$-Me-His)$^7$, Aib$^{8,35}$, Arg$^{26,34}$)hGLP-1(7-36)NH$_2$ (SEQ ID NO:75)
Example 20: ((N$^α$-Me-His)$^7$, Aib$^8$, Arg$^{26,34}$, β-Ala$^{35}$)hGLP-1(7-36)NH$_2$ (SEQ ID NO:76)
Example 21: (Aib$^8$, A6c$^{35}$)hGLP-1(7-36)NH$_2$ (SEQ ID NO:77)
Example 22: (Aib$^8$, A5c$^{35}$)hGLP-1(7-36)NH$_2$ (SEQ ID NO:78)
Example 23: (Aib$^8$, D-Ala$^{35}$)hGLP-1(7-36)NH$_2$ (SEQ ID NO:79)
Example 24: (Aib$^{8,35}$, A6c$^{32}$)hGLP-1(7-36)NH$_2$ (SEQ ID NO:16)
Example 25: (Aib$^{8,35}$, A5c$^{32}$)hGLP-1(7-36)NH$_2$ (SEQ ID NO:80)
Example 26: (Aib$^{8,35}$, Glu$^{23}$)hGLP-1(7-36)NH$_2$ (SEQ ID NO:17)
Example 27: (Aib$^{8,24,35}$)hGLP-1 (7-36)NH$_2$ (SEQ ID NO:18)
Example 28: (Aib$^{8,30,35}$)hGLP-1(7-36)NH$_2$ (SEQ ID NO:81)
Example 29: (Aib $^{8,25,35}$)hGLP-1(7-36)NH$_2$ (SEQ ID NO:82)
Example 30: (Aib$^{8,35}$ A6c$^{16,20}$)hGLP-1(7-36)NH$_2$ (SEQ ID NO:83)
Example 31: (Aib$^{8,35}$, A6c$^{16,29,32}$)hGLP-1(7-36)NH$_2$ (SEQ ID NO:84)
Example 32: (Aib$^{8,35}$ A6c$^{20,32}$)hGLP-1(7-36)NH$_2$ (SEQ ID NO:85)
Example 33: (Aib$^{8,35}$, A6c$^{20}$)hGLP-1(7-36)NR$_2$ (SEQ ID NO:86)
Example 34: (Aib$^{8,35}$, Lys$^{25}$)hGLP-1(7-36)NH$_2$ (SEQ ID NO:87)
Example 33: (Aib$^{8,35}$, A6c$^{20}$)hGLP-1(7-36)NH$_2$ (SEQ ID NO:88)
Example 36: (Aib$^{8,35}$, A6c$^{29,32}$)hGLP-1(7-36)NH$_2$ (SEQ ID NO:89)
Example 37: (Aib$^{8,24,35}$ A6c$^{29,32}$)hGLP-1(7-36)NH$_2$ (SEQ ID NO:90)
Example 38: (Aib$^{8,35}$, A6c$^{12}$)hGLP-1(7-36)NH$_2$ (SEQ ID NO:91)
Example 39: (Aib$^{8,35}$, Cha$^{20}$)hGLP-1(7-36)NH$_2$ (SEQ ID NO:92)
Example 40: (Aib$^{8,35}$, A6c$^{33}$)hGLP-1(7-36)NH$_2$ (SEQ ID NO:93)
Example 41: (Aib$^{8,35}$, A6c$^{20,32}$)hGLP-1(7-36)NH$_2$ (SEQ ID NO:85)
Example 42: (Aib$^8$, A6c$^{16,20}$, β-Ala$^{35}$)hGLP-1(7-36)NH$_2$ (SEQ ID NO:94)
Example 43: (Aib$^{8,35}$, β-Ala$^{22}$)hGLP-1(7-36)NH$_2$ (SEQ ID NO:95)
Example 44: (Aib$^{8,22,35}$)hGLP-1(7-36)NH$_2$ (SEQ ID NO:96)
Example 45: (Aib$^{8,35}$ Glu$^{23}$ A6c$^{32}$)hGLP-1(7-36)NH$_2$ (SEQ ID NO:89)
Example 46: (Aib$^{8,24,35}$ Glu$^{23}$ A6c$^{32}$)hGLP-1(736)NH$_2$ (SEQ ID NO:97)
Example 47: (Aib$^{8,24,25,35}$, Glu$^{23}$, A6c$^{32}$)hGLP-1(7-36)N$_2$ (SEQ ID NO:98)
Example 48: (Aib$^{8,24,25,35}$, A6c$^{16,20,32}$, Glu$^{23}$,)hGLP-1(7-36)NH$_2$ (SEQ ID NO:99)
Example 49: (Aib$^8$, A6c$^{32}$, β-Ala$^{35}$)hGLP-1(7-36)NH$_2$ (SEQ ID NO:100)
Example 50: (Aib$^8$, A5c$^{32}$, β-Ala$^{35}$)hGLP-1(7-36)NH$_2$ (SEQ ID NO:101)
Example 51: (Aib$^8$, Glu$^{23}$, β-Ala$^{35}$)hGLP-1(7-36)NH$_2$ (SEQ ID NO:20)
Example 52: (Aib$^{8,24}$, β-Ala$^{35}$)hGLP-1(7-36)NH$_2$ (SEQ ID NO:102)
Example 53: (Aib$^{8,30}$, β-Ala$^{35}$)hGLP-1(7-36)NH$_2$ (SEQ ID NO:103)
Example 54: (Aib$^{8,25}$, β-Ala$^{35}$)hGLP-1(7-36)NH$_2$ (SEQ ID NO:104)
Example 55: (Aib$^8$, A6c$^{16,20}$, β-Ala$^{35}$)hGLP-1(7-36)NH$_2$ (SEQ ID NO:94)
Example 56: (Aib$^8$, A6c$^{20,32}$, β-Ala$^{35}$)hGLP-1(7-36)NH$_2$ (SEQ ID NO:105)
Example 57: (Aib$^8$, A6c$^{20}$, β-Ala$^{35}$)hGLP-1(7-36)NH$_2$ (SEQ ID NO:106)
Example 58: (Aib$^8$, A6c$^{20}$, β-Ala$^{35}$)hGLP-1(7-36)NH$_2$ (SEQ ID NO:107)
Example 59: (Aib$^8$, Lys$^{25}$, β-Ala$^{35}$)hGLP-1(7-36)NH$_2$ (SEQ ID NO:108)
Example 60: (Aib$^{8,24}$, A6c$^{20}$, β-Ala$^{35}$)hGLP-1(7-36)NH$_2$ (SEQ ID NO:108)
Example 61: (Aib$^8$, A6C$^{29,32}$, β-Ala$^{35}$)hGLP-1(7-36)NH$_2$ (SEQ ID NO:110)
Example 62: (Aib$^{8,24}$, A6c$^{29,32}$, β-Ala$^{35}$)hGLP-1(7-36)NH$_2$ (SEQ ID NO:111)
Example 63: (Aib$^8$, A6c$^{12}$, β-Ala$^{35}$)hGLP-1(7-36)NH$_2$ (SEQ ID NO:112)
Example 64: (Aib$^8$, Cha$^{20}$, β-Ala$^{35}$)hGLP-1(7-36)NR$_2$ (SEQ ID NO:113)
Example 65: (Aib$^8$, A6c$^{33}$, β-Ala$^{35}$)hGLP-1(7-36)NH$_2$ (SEQ ID NO:114)
Example 66: (Aib$^8$ A6c$^{20,32}$, β-Ala$^{35}$)hGLP-1(7-36)NH$_2$ (SEQ ID NO:106)
Example 67: (Aib$^8$, β-Ala$^{22,35}$)hGLP-1(7-36)NH$_2$ (SEQ ID NO:115)
Example 66: (Aib$^{8,22}$, β-Ala$^{35}$)hGLP-1(7-36)N N$_2$ (SEQ ID NO:116)
Example 69: (Aib$^8$, Glu$^{23}$ A6c$^{32}$, β-Ala$^{35}$)hGLP-1(7-36)NH$_2$ (SEQ ID NO:117)
Example 70: (Aib$^{8,24}$, Glu$^{23}$, A6c$^{32}$, β-Ala$^{35}$)hGLP-1(7-36)NH$_2$ (SEQ ID NO:118)
Example 71: (Aib$^{8,24}$, Glu$^{23}$, A6c$^{32}$, Lys$^{34}$(N$_ε$-octanoyl), β-Ala$^{35}$)hGLP-1(7-36)NH$_2$ (SEQ ID NO:119)
Example 72: (Aib$^{8,24,25}$, Glu$^{23}$, A6c$^{32}$, β-Ala$^{35}$)hGLP-1(7-36)NH$_2$ (SEQ ID NO:120)

Example 73: (Aib$^{8,24,25}$, A6c$^{16,20,32}$ Glu$^{23}$, β-Ala$^{35}$)hGLP-1(7-36)NH$_2$ (SEQ ID NO:121)
Example 74: (Aib$^{8,35}$, D-Arg$^{36}$)hGLP-1(7-36)NH$_2$ (SEQ ID NO:122)
Example 75: (Aib$^{8,35}$, D-Lys$^{36}$)hGLP-1 (7-36)NH$_2$ (SEQ ID NO:123)
Example 76: (Aib$^8$, β-Ala$^{35}$, D-Arg$^{36}$)hGLP-1(7-36)NH$_2$ (SEQ ID NO:124)
Example 77: (Aib$^8$, β-Ala$^{35}$, D-Lys$^{36}$)hGLP-1(7-36)NH$_2$ (SEQ ID NO:125)
Example 78: (Aib$^{8,35}$ Arg$^{26,34}$)hGLP-1(7-36)NH$_2$ (SEQ ID NO:21)
Example 79: (Aib$^8$, Arg$^{226,34}$ β-Ala$^{35}$)hGLP-1(7-36)NH$_2$ (SEQ ID NO:126)
Example 80: (Aib$^{8,35}$ Arg$^{25,26,34}$)hGLP-1(7-36)NH$_2$ (SEQ ID NO:127)
Example 81: (Aib 8, Arg$^{25,26,34}$, β-Ala$^{35}$)hGLP-1(7-36)NH$_2$ (SEQ ID NO:128)
Example 82: (Aib$^8$, Arg$^{26,34}$, β-Ala$^{36}$, Lys$^{36}$(N$^ε$-tetradecanoyl))hGLP-1(7-36)OH (SEQ ID NO:129)
Example 83: (Aib$^{8,35}$, Arg$^{26,34}$, Lys$^{36}$(N$^ε$-tetradecanoyl)) hGLP-1(7-37)OH (SEQ ID NO:130)
Example 84: (Aib$^{8,35,37}$, Arg$^{26,34}$, Lys$^{36}$N$^ε$-tetradecanoyl)) hGLP-1(7-37)0H (SEQ ID NO:131)
Example 84: (Aib$^{8,35,37}$, Arg$^{26,34}$, Lys$^{36}$(N$^ε$-tetradecanoyl)) hGLP-1(7-37)OH (SEQ ID NO:131)
Example 85: (Aib$^{8,35}$, Arg$^{26,34}$, Lys$^{36}$(N$^ε$-tetradecanoyl), D-Ala$^{37}$)hGLP-1(7-37)OH (SEQ ID NO:132)
Example 86: (Aib$^{8,35,37}$, Arg$^{26,34}$, Lys$^{38}$(N$^ε$-tetradecanoyl)) hGLP-1(7-38)OH (SEQ ID NO:133)
Example 87: (Aib$^{8,35}$, Arg$^{26,34}$, β-Ala$^{37}$, Lys$^{38}$(N$^ε$-tetradecanoyl))hGLP-1(7-38)OH (SEQ ID NO:134)
Example 88: (Aib$^{8,35}$, Arg$^{26,34}$ Lys$^{38}$(N$^ε$-tetradecanoyl)) hGLP-1(7-38)OH(SEQ ID NO:135)
Example 89: (Aib$^8$, Arg$^{26,34}$, Lys$^{36}$ (N$^ε$-tetradecanoyl), β-Ala$^{37}$)hGLP-1(7-37)OH (SEQ ID NO:136)
Example 90: (Aib$^{8,37}$, Arg$^{26,34}$, Lys$^{36}$(N$^ε$-tetradecanoyl)) hGLP-1(7-37)OH(SEQ ID NO:137)
Example 91: (Aib$^{8,35}$, Arg$^{26,34}$, Ado$^{37}$)hGLP-[(7-37)OH (SEQ ID NO:138)
Example 92: (Aib$^{8,35}$ Arg$^{26,34}$ Ado$^{37}$)hGLP-1(7-37)NH$_2$ (SEQ ID NO:139)
Example 93: (Aib$^8$, Arg$^{26,34}$, Lys$^{36}$(N$^ε$-tetradecanoyl), D-Ala$^{37}$)hGLP-1(7-37)OH (SEQ ID NO 140)
Example 94: (Aib$^{8,37}$, Arg$^{26,34}$, Lys$^{38l\ (Nε}$-tetradecanoyl)) hGLP-1(7-38)OH (SEQ ID NO:141)
Example 95: (Aib$^8$, Arg$^{26,34}$, Ala$^{37}$, Lys$^{38}$(N$^ε$-tetradecanoyl))hGLP-1(7-38)OH (SEQ ID NO:142)
Example 96: (Aib$^{8,35}$, Lys$^{26}$(N$^ε$-octanoyl))hGLP-1(7-36) NH$_2$ (SEQ ID NO:143)
Example 97: (Aib$^{8,35}$, Lys$^{26}$(N$^ε$-tetradecanoyl))hGLP-1(7-36)NH$_2$ (SEQ ID NO:144)
Example 98: (Aib$^{8,35}$, Lys$^{26}$ (N$^ε$-hexadecanoyl))hGLP-1 (7-36)NH$_2$ (SEQ ID NO:145)
Example 99: (Aib$^8$, Lys$^{26}$ (N$^ε$-octanoyl), β-Ala$^{35}$)hGLP-1 (7-36)NH$_2$ (SEQ ID NO:146)
Example 100: (Aib$^8$, Lys$^{26}$(N$^ε$-tetradecanoyl), β-Ala$^{35}$)] GLP-1(7-36)NH$_2$ (SEQ ID NO:147)
Example 101: (Aib$^8$, Lys$^{26}$(N$^ε$-hexadecanoyl), β-Ala$^{35}$) hGLP-1(7-36)NH$_2$ (SEQ ID NO:148)
Example 102: (Aib$^{8,35}$, Lys$^{26}$ (N$^ε$-octanoyl), Arg$^{34}$)hGLP-1 (7-36)NH$_2$ (SEQ ID NO:149)
Example 103: (Aib$^{8,35}$, Lys$^{26}$(N$^ε$-tetradecanoyl), Arg$^{34}$) hGLP-1(7-36)NH$_2$ (SEQ ID NO:150)
Example 104: (Aib$^{8,35}$, Lys$^{26}$ (N$^ε$-hexadecanoyl), Arg$^{34}$) hGLP-1(7-36)NH$_2$ (SEQ ID NO:151)
Example 105: (Aib$^{8,35}$, Lys$^{26}$(N$^ε$-decanoyl), Arg$^{34}$)hGLP-1 (7-36)NH$_2$ (SEQ ID NO:152)

Example 106: (Aib$^{8,35}$, Lys$^{25}$, Lys$^{26}$(N$^ε$-octanoyl), Arg$^{34}$) hGLP-1(7-36)NH$_2$ (SEQ ID NO:153)
Example 107: (Aib $^{8,35}$, Lys$^{25}$, Lys$^{26}$(N$^ε$-tetradecanoyl), Arg$^{34}$)hGLP-1(7-36)NH$_2$ (SEQ ID NO:154)
Example 108: (Aib$^{8,35}$, Lys$^{25}$, Lys$^{26}$(N$^ε$-hexadecanoyl), Arg$^{34}$)hGLP-1(7-36)NH$_2$ (SEQ ID NO:155)
Example 109: (Aib$^{8,35}$ Arg$^{25,34}$, Lys$^{26}$(N$^ε$-octanoyl))hGLP-1(7-36)NH$_2$ (SEQ ID NO:156)
Example 110: (Aib$^{8,35}$, Arg$^{25,34}$, Lys$^{26}$(N$^ε$-tetradecanoyl)) hGLP-1 (7-36)NH$_2$ (SEQ ID NO:157)
Example 111: (Aib$^{8,35}$, Arg$^{25,34}$, Lys$^{26}$ (N$^ε$-hexadecanoyl)) hGLP-1(7-36)NH$_2$ (SEQ ID NO:158)
Example 112: (Aib$^{8,35}$ Arg$^{25,34}$ Lys$^{26}$(N$^ε$-decanoyl))hGLP-1(7-36)NH$_2$ (SEQ ID NO:159)
Example 113: (Aib$^8$, Lys$^{26}$(N$^ε$-octanoyl), Arg$^{34}$, β-Ala$^{35}$) hGLP-1(7-36)NH$_2$ (SEQ ID NO:160)
Example 1114: (Aib$^8$, Lys$^{26}$(N$^ε$-tetradecanoyl), Arg$^{34}$, β-Ala$^{35}$)hGLP-1(7-36)NH$_2$ (SEQ ID NO:161)
Example 115: (Aib$^8$, Lys$^{26}$(N$^ε$-hexadecanoyl), Arg$^{34}$, β-Ala$^{35}$)hGLP-1(7-36)NH$_2$ (SEQ ID NO:162)
Example 116: (Aib$^8$, Lys$^{26}$ (N$^ε$-decanoyl), Arg$^{34}$, β-Ala$^{35}$) hGLP-1 (7-36)NH$_2$ (SEQ ID NO:163)
Example 117: (Aib$^{8,35}$, Lys$^{34}$(N$^ε$-octanoyl))hGLP-1(7-36) NH$_2$ (SEQ ID NO:164)
Example 118: (Aib$^{8,35}$, Lys$^{34}$(N-tetradecanoyl))hGLP-1(7-36)NH$_2$ (SEQ ID NO:165)
Example 119: (Aib$^{8,35}$, Lys$^{34}$ (N$^ε$-hexadecanoyl))hGLP-1 (7-36)NH$_2$ (SEQ ID NO:166)
Example 120: (Aib$^{8,35}$, Arg$^{26}$, Lys$^{34}$(N$^ε$-octanoyl))hGLP-1 (736)NH$_2$ (SEQ ID NO:167)
Example 121: (Aib$^{8,35}$, Arg$^{26}$, Lys$^{34}$(N$^ε$-hexadecanoyl)) hGLP-1(7736)NH$_2$ (SEQ ID NO:168)
Example 122: (Aib$^{8,35}$, Arg$^{26}$, Lys$^{34}$(N$^ε$-decanoyl))hGLP-1 (7-36)NH$_2$ (SEQ ID NO:169)
Example 123: (Aib$^{8,35}$, Arg$^{25,26}$ Lys$^{34}$ (N$^ε$-octanoyl))hGLP-1(736)NH$_2$(SEQ ID NO 170)
Example 124: (Aib$^{8,35}$, Arg$^{25,26}$ Lys$^{34}$(N$^ε$-tetradecanoyl)) hGLP-1(7-36)NH$_2$ (SEQ ID NO: 71)
Example 125: (Aib$^{8,35}$, Arg$^{25,26}$, Lys$^{34}$(N$^ε$-hexadecanoyl)) hGLP-11(7736)NH$_2$ (SEQ ID NO:172)
Example 126: (Aib$^{8,35}$, Arg$^{25,26}$, Lys$^{34}$(N$^ε$-decanoyl)) hGLP-1(7-36)NH$_2$ (SEQ ID NO:173)
Example 127: (Aib$^{8,35}$, Lys$^{25}$, Arg$^{26}$, Lys$^{34}$(N$^ε$-octanoyl)) hGLP-1(7-36)NH$_2$ (SEQ ID NO:174)
Example 128: (Aib$^{8,35}$ Lys$^{25}$, Arg$^{26}$, Lys$^{34}$(N$^ε$-tetradecanoyl))hGLP-1(7-36)NH$_2$ (SEQ ID NO:175)
Example 129: (Aib$^{8,35}$, Lys$^{25}$, Arg$^{26}$ Lys$^{34}$(N$^ε$-hexadecanoyl))hGLP-1 (7-36)NH$_2$ (SEQ ID NO:176)
Example 130: (Aib$^{8,35}$, Lys$^{36}$(N$^ε$-octanoyl))hGLP-1(7-36) NH$_2$ (SEQ ID NO:177)
Example 131: (Aib$^{8,35}$, Lys$^{36}$(N$^ε$-tetradecanoyl))hGLP-1(7-36)NH$_2$ (SEQ ID NO:178)
Example 132: (Aib$^{8,35}$, Lys$^{36}$(N$^ε$-hexadecanoyl))hGLP-1 (7-36)NH$_2$ (SEQ ID NO:179)
Example 133: (Aib$^{8,35}$, Arg$^{26}$, Lys$^{36}$(N$^ε$-octanoyl))hGLP-1 (7-36)NH$_2$ (SEQ ID NO:180)
Example 134: (Aib$^{8,35}$, Arg$^{16}$, Lys$^{36}$(N$^ε$-tetradecanoyl)) hGLP-1(7-36)NH$_2$ (SEQ ID NO:181)
Example 135: (Aib$^{8,35}$, Arg$^{26}$, Lys$^{36}$(N$^ε$-hexadecanoyl)) hGLP-1(7-36)NH$_2$ (SEQ ID NO:182)
Example 136: (Aib$^{8,35}$, Arg$^{26,34}$ Lys$^{36}$(N$^ε$-octanoyl))hGLP-1(7-36)NH$_2$ (SEQ ID NO:183)
Example 137: (Aib$^{8,35}$, Arg$^{26,34}$, Lys$^{36}$(N$^ε$-hexadecanoyl)) hGLP-1(7-36)NH$_2$ (SEQ ID NO:184)
Example 138: (Aib$^{8,35}$, Arg$^{26,34}$, Lys$^{38}$(N$^ε$-octanoyl))hGLP-1(7-38)NH$_2$ (SEQ ID NO:185)
Example 139: (Aib$^{8,35}$, Arg$^{26,34}$, Lys$^{38}$(N$^ε$-decanoyl)) hGLP-1(7-38)NH$_2$ (SEQ ID NO:186)

Example 140: (Aib$^{8,35}$ Arg$^{26,34}$ Lys$^{38}$ N$^\epsilon$-tetradecanoyl)) hGLP-1(7-38)NH$_2$ (SEQ ID NO:187)

Example 141: (Aib$^{8,35}$, Arg$^{26,34}$, Lys$^{38}$(N$^\epsilon$-hexadecanoyl)) hGLP-1(7-38)NH$_2$ (SEQ ID NO:188)

Example 142: (Aib$^{8,35,37}$, Arg$^{25,26,34}$, Lys$^{38}$(N$^\epsilon$-octanoyl)) hGLP-1(7-38)NH$_2$ (SEQ ID NO:189)

Example 143 (Aib$^{8,35,37}$, Arg$^{26,26,34}$ Lys$^{38}$(N$^\epsilon$-decanoyl)) hGLP-1(7-38)NH$_2$ (SEQ ID NO:190)

Example 144: (Aib$^{8,35,37}$ Arg$^{25,26,34}$ Lys$^{38}$(N$^\epsilon$-tetradecanoyl))hGLP-1(738)NH$_2$(SEQ ID NO:191)

Example 145: (Aib$^{8,35,37}$, Arg$^{25,26,34}$, Lys$^{38}$(N$^\epsilon$-hexadecanoyl))hGLP-1(7-38)NH$_2$ (SEQ ID NO:191)

Example 146: (Aib$^{8,35,37}$, Arg$^{26,34}$, Lys$^{38}$(N$^\epsilon$-octanoyl)) hGLP-1(7-38)NH$_2$(SEQ ID NO:193)

Example 147: (Aib$^{8,35,37}$, Arg$^{26,34}$, Lys$^{38}$(N$^\epsilon$-decanoyl)) hGLP-1(7-38)NH$_2$ (SEQ ID NO:194)

Example 148: (Aib$^{8,35,37}$, Arg$^{26,34}$, Lys$^{38}$(N$^\epsilon$-hexadecanoyl))hGLP-1(7-38)NH$_2$ (SEQ ID NO:195)

Example 149: (Aib$^{8,35,37}$, Arg$^{25,26}$, Lys$^{38}$(N$^\epsilon$-octanoyl)) hGLP-1(7-38)NH$_2$ (SEQ ID NO:189)

Example 150: (Aib$^{8,35,37}$, Arg$^{25,26,34}$, Lys$^{38}$(N$^\epsilon$-decanoyl)) hGLP-1(7-38)NH$_2$ (SEQ ID NO:190)

Example 151: (Aib$^{8,35,37}$, Arg$^{25,26,34}$, Lys$^{38}$(N$^\epsilon$-tetradecanoyl))hGLP-1(7-38)N H$_2$ (SEQ ID NO:191)

Example 152: (Aib$^{8,35,37}$, Arg$^{25,26,34}$, Lys$^{38}$(N$^\epsilon$-hexadecanoyl))hGLP-1(7-38)NH$_2$(SEQ ID NO:192)

Example 153: (Aib$^{8,35}$ Lys$^{25}$ Arg$^{26,34}$ Lys$^{36}$(N$^\epsilon$-octanoyl)) hGLP-1(7-36)NH$_2$ (SEQ ID NO:196)

Example 154: (Aib$^{8,35}$, Lys$^{25}$, Arg$^{26,34}$, Lys$^{36}$ (N$^\epsilon$-tetradecanoyl))hGLP-1(7-36)NH$_2$ (SEQ ID NO:197)

Example 155: (Aib$^{8,35}$, Lys$^{25}$, Arg$^{26,34}$, Lys$^{36}$(N$^\epsilon$-hexadecanoyl))hGLP-1(7-36)NH$_2$(SEQ ID NO:198)

Example 156: (Aib$^{8,35}$, Arg$^{25,26,34}$, Lys$^{36}$(N$^\epsilon$-octanoyl)) hGLP-1(7-36)NH$_2$ (SEQ ID NO:199)

Example 157: (Aib$^{8,35}$, Arg$^{25,26,34}$, Lys$^{36}$(N$^\epsilon$-tetradecanoyl))hGLP-1(7-36)NH$_2$ (SEQ ID NO:200)

Example 158: (Aib$^{8,35}$, Arg$^{25,26,34}$, Lys$^{36}$(N$^\epsilon$-hexadecanoyl))hGLP-1(7-36)NH$_2$ (SEQ ID NO:201)

Example 159: (Aib$^{8,35}$, Arg$^{25,26,34}$, Lys$^{36}$(N$^\epsilon$-decanoyl)) hGLP-1(7-36)NH$_2$ (SEQ ID NO:202)

Example 160: (Aib$^8$, Lys$^{34}$(N$^\epsilon$-octanoyl), β-Ala$^{35}$)hGLP-1 (7-36)NH$_2$ (SEQ ID NO:203)

Example 161: (Aib$^8$, Lys$^{34}$(N$^\epsilon$-tetradecanoyl), β-Ala$^{35}$) hGLP-1(7-36)NH$_2$ (SEQ ID NO:204)

Example 162: (Aib$^8$, Lys$^{34}$(N$^\epsilon$-hexadecanoyl), 13-Ala$^{35}$) hGLP-1(7-36)NH$_2$ (SEQ ID NO:205)

Example 163: (Aib$^8$, A6c$^{32}$, Lys$^{34}$(N$_\epsilon$-octanoyl), β-Ala$^{35}$) hGLP-1(7-36)NH$_2$ (SEQ ID NO:206)

Example 164: (Aib$^8$, Glu$^{23}$, Lys$^{34}$ (N$^\epsilon$-octanoyl), β-Ala$^{35}$) hGLP-1(7-36)NH$_2$ (SEQ ID NO:207)

Example 165: (Aib$^8$, Glu$^{23}$, A6c$^{32}$, Lys$^{34}$ (N$^\epsilon$-octanoyl), β-Ala$^{35}$)hGLP-1(7-36)NH$_2$ (SEQ ID NO:208)

Example 166: (Aib$^8$, Arg$^{26}$, Lys$^{34}$(N$^\epsilon$-octanoyl), β-Ala$^{35}$) hGLP-1(7-36)NH$_2$ (SEQ ID NO:209)

Example 167: (Aib$^8$, Arg$^{26}$, Lys$^{34}$ (N$^\epsilon$-tetradecanoyl), β-Ala$^{35}$)hGLP-1(7-36)NH$_2$ (SEQ ID NO:210)

Example 168: (Aib$^8$, Arg$^{26}$, Lys$^{34}$(N$^\epsilon$-hexadecanoyl), β-Ala$^{35}$)hGLP-1(7-36)NH$_2$ (SEQ ID NO:211)

Example 169: (Aib$^8$, Arg$^{26}$, Lys$^{34}$(N$^\epsilon$-decanoyl), β-Ala$^{35}$) hGLP-1(7-36)NH$_2$ (SEQ ID NO:212)

Example 170: (Aib$^8$, Arg$^{25,26}$, Lys$^{34}$(N$^\epsilon$-octanoyl), β-Ala$^{35}$) hGLP-1(7-36)NH$_2$ (SEQ ID NO:213)

Example 171: (Aib$^8$, Arg$^{25,26}$, Lys$^{34}$(ε-tetradecanoyl), β-Ala$^{35}$)hGLP-1(7-36)NH$_2$(SEQ ID NO:214)

Example 172: (Aib$^8$, Arg$^{25,26}$, Lys$^{34}$(N$^\epsilon$-hexadecanoyl), β-Ala$^{35}$)hGLP-1 (7-36)NH$_2$ (SEQ ID NO:215)

Example 173: (Aib$^8$, Arg$^{25,26}$, Lys$^{34}$(N$^\epsilon$-decanoyl), β-Ala$^{35}$) hGLP-1(7-36)NH$_2$ (SEQ ID NO:216)

Example 174: (Aib$^8$, Lys$^{25}$, Arg$^{26}$, Lys$^{34}$(N$^\epsilon$-octanoyl), β-Ala$^{35}$)hGLP-1(7-36)NH$_2$ (SEQ ID NO:217)

Example 175: (Aib$^8$, Lys$^{25}$, Arg$^{26}$, Lys$^{34}$(N$^\epsilon$-tetradecanoyl), β-Ala$^{35}$)hGLP-1(7-36)NH$_2$ (SEQ ID NO:218)

Example 176: (Aib$^8$, Lys$^{25}$, Arg$^{26}$, Lys$^{34}$(N$^\epsilon$-hexadecanoyl), β-Ala$^{35}$)hGLP-1(7-36)NH$_2$ (SEQ ID NO:219)

Example 177: (Aib$^8$, β-Ala$^{35}$, Lys$^{36}$(N$^\epsilon$-octanoyl))hGLP-1 (7-36)NH$_2$ (SEQ ID NO:220)

Example 178: (Aib$^8$, β-Ala$^{35}$, Lys$^{36}$(N$^\epsilon$-tetradecanoyl)) hGLP-1(7-36)NH$_2$ (SEQ ID NO:221)

Example 179: (Aib$^8$, β-Ala$^{35}$, Lys$^{36}$(N$^\epsilon$-hexadecanoyl)) hGLP-1(7-36)NH$_2$ (SEQ ID NO:222)

Example 180: (Aib$^8$, Arg$^{26}$, β-Ala$^{35}$, Lys$^{36}$(N$^\epsilon$-octanoyl)) hGLP-1(7-36)NH$_2$ (SEQ ID NO:223)

Example 181: (Aib$^8$, Arg$^{26}$, β-Ala$^{35}$, Lys$^{36}$(N$^\epsilon$-tetradecanoyl))hGLP-1(7-36)NH$_2$ (SEQ ID NO:224)

Example 182: (Aib$^8$, Arg$^{26}$, β-Ala$^{35}$, Lys$^{36}$ (N$^\epsilon$-hexadecanoyl)hGLP-1(7-36)NH$_2$ (SEQ ID NO:225)

Example 183: (Aib$^8$, Arg$^{26,34}$, β-Ala$^{35}$, Lys$^{36}$(N$^\epsilon$-octanoyl)) hGLP-1(7-36)NH$_2$ (SEQ ID NO:226)

Example 184: (Aib$^8$, Arg$^{26,34}$, β-Ala$^{35}$, Lys$^{36}$(N$^\epsilon$-tetradecanoyl))hGLP-1(7-36)NH$_2$ (SEQ ID NO:227)

Example 185: (Aib$^8$, Arg$^{26,34}$, β-Ala$^{35}$, Lys$^{36}$(N$^\epsilon$-hexadecanoyl))hGLP-1(7-36)NH$_2$ (SEQ ID NO:228)

Example 186: (Aib$^8$, Arg$^{26,34}$, β-Ala$^{35}$, Lys$^{36}$ (N$^\epsilon$-decanoyl))hGLP-1(7-36)NH$_2$ (SEQ ID NO:229)

Example 187: (Aib$^8$, Lys$^{25}$, Arg$^{26,34}$, β-Ala$^{35}$, Lys$^{36}$(N$^\epsilon$-octanoyl))hGLP-1(7-36)NH$_2$ (SEQ ID NO:230)

Example 188: (Aib$^8$, Lys$^{25}$, Arg$^{26,34}$, Lys$^{36}$ (N$^\epsilon$-tetradecanoyl), P3-Ala$^{35}$)hGLP-1(7-36)NH$_2$ (SEQ ID NO:231)

Example 189: (Aib$^8$, Lys$^{25}$, Arg$^{26,34}$, β-Ala$^{35}$, Lys$^{36}$ (N$^\epsilon$-hexadecanoyl))hGLP-1(7-36)NH$_7$ (SEQ ID NO:232)

Example 190: (Aib$^8$, Arg$^{25,26,34}$, β-Ala$^{35}$, Lys$^{36}$(N$^\epsilon$-octanoyl))hGLP-1(7-36)NH$_2$ (SEQ ID NO:233)

Example 191: (Aib$^8$, Arg$^{25,26,34}$, β-Ala$^{35}$, Lys$^{36}$(N$^\epsilon$-tetradecanoyl))hGLP-1(7-36)NH$_2$ (SEQ ID NO:234)

Example 192: (Aib$^8$, Arg$^{25,26,34}$, β-Ala$^{35}$, Lys$^{36}$(N$^\epsilon$-hexadecanoyl))hGLP-1(7-36)NH$_2$ (SEQ ID NO:235)

Example 193: (Aib$^8$, Arg$^{25,26,34}$, β-Ala$^{35}$, Lys$^{36}$(N$^\epsilon$-decanoyl))hGLP-1(7-36)NH$_2$ (SEQ ID NO:236)

Example 194: (Aib$^{8,35}$, Lys$^{26}$(N$^\epsilon$-octanoyl), A6c$^{32}$, Arg$^{34}$) hGLP-1(7-36)NH$_2$ (SEQ ID NO:237)

Example 195: (Aib$^{8,35}$, Lys$^{26}$(N$^\epsilon$-tetradecanoyl), A6c$^{32}$, Arg)hGLP-1(7-36)NH$_2$ (SEQ ID NO:238)

Example 196: (Aib$^{8,35}$, Lys$^{26}$(N$^\epsilon$-hexadecanoyl), A6c$^{32}$, Arg$^{34}$)hGLP-1(7-36)NH$_2$ (SEQ ID NO:239)

Example 197: (Aib$^{8,35}$, A6c$^{32}$, Lys$^{34}$ (N$^\epsilon$-octanoyl))hGLP-1(7-36)NH$_2$ (SEQ ID NO:240)

Example 198: (Aib$^{8,35}$, A6c$^{32}$, Lys$^{34}$(N$^\epsilon$-tetradecanoyl)) hGLP-1(7-36)NH$_2$ (SEQ ID NO:241)

Example 199: (Aib$^{8,35}$, A6c$^{32}$, Lys$^{34}$(N$^\epsilon$-hexadecanoyl)) hGLP-1(7-36)NH$_2$ (SEQ ID NO:242)

Example 200: (Aib$^{8,35}$, Arg$^{26}$, A6c$^{32}$, Lys$^{34}$(N$^\epsilon$-octanoyl)) hGLP-1(7-36)NH$_2$ (SEQ ID NO:243)

Example 201: (Aib$^{8,35}$, Arg, A6c$^{32}$, Lys$^{34}$ (N$^\epsilon$-tetradecanoyl))hGLP-1(7-36)NH$_2$ (SEQ ID NO:244)

Example 202: (Aib$^{8,35}$, A6c$^{32}$, Lys$^{36}$(N$^\epsilon$-octanoyl))hGLP-1 (7-36)NH$_2$ (SEQ ID NO:245)

Example 203: (Aib$^{8,35}$, A6c$^{32}$, Lys$^{36}$(N$^\epsilon$-tetradecanoyl)) hGLP-1(7-36)NH$_2$ (SEQ ID NO:246)

Example 204: (Aib$^{8,35}$, A6c$^{32}$, Lys$^{36}$(N$^\epsilon$-hexadecanoyl)) hGLP-1(7-36)NH$_2$(SEQ ID NO:247)

Example 205: (Aib$^{8,35}$, Arg$^{26}$, A6c$^{32}$, Lys$^{36}$(N$^\epsilon$-octanoyl)) hGLP-1(7-36)NH$_2$ (SEQ ID NO:248)

Example 206: (Aib$^{8,35}$, Arg$^{26}$, A6c$^{32}$, Lys$^{36}$(N$^\epsilon$-tetradecanoyl))hGLP-1(7-36)NH$_2$ (SEQ ID NO:249)

Example 207: (Aib$^{8,35}$, Arg$^{26}$, A6c$^{32}$, Lys$^{36}$(N$^\epsilon$-hexadecanoyl))hGLP-1 (7-36)NH$_2$ (SEQ ID NO:250)
Example 208: (Aib$^{8,35}$, Arg$^{26,34}$ A6c$^{32}$ Lys$^{36}$(N$^\epsilon$-octanoyl)) hGLP-1(7-36)NH$_2$ (SEQ ID NO:251)
Example 209: (Aib$^{3,35}$, Arg$^{26,34}$, A6c$^{32}$ Lys$^{36}$(N$^\epsilon$-decanoyl)) hGLP-1(7-36)NH$_2$ (SEQ ID NO:252)
Example 210: (Aib$^{8,35}$, Arg$^{26,34}$, A6c$^{32}$ Lys$^{36}$(N$^\epsilon$-tetradecanoyl))hGLP-1(7-36)NH$_2$ (SEQ ID NO:253)
Example 211 (Aib$^{8,35}$, Arg$^{26,34}$, A6c$^{32}$ Lys$^{36}$ (N$^\epsilon$-hexadecanoyl))hGLP-1(7-6)NH$_2$ (SEQ ID NO:254)
Example 211: (Aib$^{8,35}$, Arg$^{26,34}$, A6c$^{32}$ Ly (N$^\epsilon$-hexadecanoyl))hGLP)-(7-36)NH$_2$(SEQ ID NO:254)
Example 212: (Aib$^{8,24,35}$, Lys$^{26}$(N$^\epsilon$-octanoyl), Arg$^{34}$)hGLP-1(7-36)NH$_2$ (SEQ ID NO:255)
Example 213: (Aib$^{824,35}$, Lys$^{26}$ (N$^\epsilon$-tetradecanoyl), Arg$^{34}$) hGLP-1(7-36)NH$_2$ (SEQ ID NO:256)
Example 214: (Aib$^{8,24,35}$, Lys$^{26}$(N$^\epsilon$-hexadecanoyl), Arg$^{34}$) hGLP-1(7-36)NH$_2$ (SEQ ID NO:257)
Example 215: (Aib$^{8,24,35}$, Arg$^{26}$, Lys$^{34}$(N$^\epsilon$-octanoyl))hGLP-1(7-36)NH$_2$ (SEQ ID NO:258)
Example 216: (Aib$^{8,24,35}$, Arg$^{26}$, Lys$^{34}$(N$^\epsilon$-tetradecanoyl)) hGLP-1(736)NH$_2$ (SEQ ID NO:259)
Example 217: (Aib $^{8,24,35}$, Arg$^{26}$, Lys$^{34}$(N$^\epsilon$-hexadecanoyl)) hGLP-1 (7-36)NH$_2$ (SEQ ID NO:260)
Example 218: (Aib$^{8,24,35}$ Arg$^{26,34}$, Lys$^3$(N$^\epsilon$-octanoyl)) hGLP-1(7-36)NH$_2$ (SEQ ID NO:261)
Example 219: (Aib$^{8,24,35}$, Arg$^{26,34}$, Lys$^{36}$(N$^\epsilon$-tetradecanoyl))hGLP-1(7-36)NH$_2$ (SEQ ID NO:262)
Example 220: (Aib$^{8,24,35}$, Arg$^{26,34}$, Lys$^{36}$(N$^\epsilon$-hexadecanoyl))hGLP-1(7-36)NH$_2$ (SEQ ID NO:263)
Example 221: (Aib$^{8,24,35}$ Glu$^{23}$, A6c$^{32}$, Lys$^{34}$(N$^\epsilon$-octanoyl)) hGLP-1(7-36)NH$_2$ (SEQ ID NO:264)
Example 222: (Aib$^{8,35}$, Glu$^{23}$, Lys$^{26}$ N$^\epsilon$-octanoyl), Arg$^{34}$) hGLP-1(7-36)NH$_2$ (SEQ ID NO:265)
Example 223: (Aib$^{8,35}$, Glu$^{23}$ Lys$^{26}$(N$^\epsilon$-tetradecanoyl), Arg$^{34}$)hGLP-1(7-36)NH$_2$ (SEQ ID NO:266)
Example 224: (Aib$^{8,35}$, Glu$^{23}$, Lys$^{26}$ (N$^\epsilon$-hexadecanoyl), Arg$^{34}$)hGLP-1(7-36)NH$_2$ (SEQ ID NO:267)
Example 225: (Aib$^{8,35}$, Glu$^{23}$, Lys$^{34}$ (N$^\epsilon$-octanoyl)) hGLP-1(7-36)NH$_2$ (SEQ ID NO:268)
Example 226: (Aib$^{8,35}$, Glu$^{23}$, A6c$^{32}$, Lys$^{34}$ (N$^\epsilon$-octanoyl)) hGLP-1(7-36)NH$_2$ (SEQ ID NO:269)
Example 227: (Aib$^{8,35}$, Glu$^{23}$, Arg$^{26}$, Lys$^{34}$(N$^\epsilon$-octanoyl)) hGLP-1(7-36)NH$_2$ (SEQ ID NO:270)
Example 228: (Aib$^{8,35}$, Glu$^{23}$, Arg$^{26}$, Lys$^{34}$(N$^\epsilon$-tetradecanoyl))hGLP-1(7-36)NH$_2$ (SEQ ID NO:271)
Example 229: (Aib$^{8,35}$, Glu$^{23}$, Arg$^{26}$, Lys$^{34}$(N$^\epsilon$-hexadecanoyl))hGLP-1(7-36)NH$_2$ (SEQ ID NO:272)
Example 230: (Aib$^{8,35}$, Glu$^{23}$, Lys$^{36}$(N$^\epsilon$-octanoyl))hGLP-1(7-36)NH$_2$ (SEQ ID NO:273)
Example 231: (Aib$^{8,35}$, Glu$^{23}$, Lys$^{36}$(N$^\epsilon$-tetradecanoyl)) hGLP-1(7-36)NH$_2$ (SEQ ID NO:274)
Example 232: (Aib$^{8,35}$, Glu$^{23}$, Lys$^{36}$ (N$^\epsilon$-hexadecanoyl)) hGLP-1 (7-36)NH$_2$ (SEQ ID NO:275)
Example 233: (Aib$^{8,35}$, Glu$^{23}$, Arg$^{26,34}$, Lys$^{36}$ (N$^\epsilon$-octanoyl))hGLP-1(7-36)NH$_2$ (SEQ ID NO:276)
Example 234: (Aib$^{8,35}$ Glu$^{23}$ Arg$^{26,34}$ Lys$^{36}$(N$^\epsilon$-tetradecanoyl))hGLP-1(7-36)NH$_2$ (SEQ ID NO:277)
Example 235: (Aib$^{8,35}$, Glu$^{23}$ Arg$^{26,34}$ Lys$^{36}$(N$^\epsilon$-hexadecanoyl))hGLP-1(7-36)NH$_2$ (SEQ ID NO:278)
Example 236: (Aib$^{8,30,35}$, Lys$^{26}$(N$^\epsilon$-octanoyl), Arg$^{34}$)hGLP-1(7-36)NH$_2$ (SEQ ID NO:279)
Example 237: (Aib$^{8,30,35}$, Lys$^{26}$ (N$^\epsilon$-tetradecanoyl), Arg$^{34}$) hGLP-1(7-36)NH$_2$ (SEQ ID NO:280)
Example 238: (Aib$^{8,30,35}$, Lys$^{26}$ (N$^\epsilon$-hexadecanoyl), Arg$^{34}$) hGLP-1(7-36)NH$_2$ (SEQ ID NO:281)
Example 239: (Aib$^{8,30,35}$, Arg$^{26}$, Lys$^{34}$(N$^\epsilon$-octanoyl))hGLP-1(7-36)NH$_2$ (SEQ ID NO:282)
Example 240: (Aib$^{8,30,35}$, Arg$^{26}$, Lys$^{34}$(N$^\epsilon$-tetradecanoyl)) hGLP-1(7-36)NH$_2$ (SEQ ID NO:283)
Example 241: (Aib$^{8,30,35}$, Arg$^{26}$, Lys$^{34}$(N$^\epsilon$-hexadecanoyl)) hGLP-1(7-36)NH$_2$ (SEQ ID NO:284)
Example 242: (Aib$^{8,30,35}$, Arg$^{26,34}$, Lys$^{36}$(N$^\epsilon$-6-octanoyl)) hGLP-1(7-36)NH$_2$ (SEQ ID NO:285)
Example 243: (Aib$^{8,30,35}$, Arg$^{26,34}$, Lys$^{36}$(N$^\epsilon$-tetradecanoyl))hGLP-1(7-36)NH$_2$ (SEQ ID NO:286)
Example 244: (Aib$^{8,30,35}$ Arg$^{26,34}$ Lys$^{36}$(N$^\epsilon$-hexadecanoyl)) hGLP-1(7-36)NH$_2$ (SEQ ID NO:287)
Example 245: (Aib$^{8,35}$, Glu$^{23}$, A6c$^{32}$, Lys$^{36}$(N$^\epsilon$-octanoyl)) hGLP-1(7-36)NH$_2$ (SEQ ID NO:288)
Example 246: (Aib$^{8,35}$, Glu$^{23}$, A6c$^{32}$, Lys$^{36}$(N$^\epsilon$-tetradecanoyl))hGLP-1(7-36)NH$_2$ (SEQ ID NO:289)
Example 247: (Aib$^{8,35}$, Glu$^{23}$, A6c$^{32}$, Lys$^{36}$ (N$^\epsilon$-hexadecanoyl))hGLP-1(7-36)NH$_2$ (SEQ ID NO:290)
Example 248: (Aib $^{8,35}$, Glu$^{23}$, Arg$^{26,34}$, A6c$^{32}$, Lys$^{36}$(N$^\epsilon$-octanoyl))hGLP-1(7-36)NH$_2$ (SEQ ID NO:291)
Example 249: (Aib$^{8,35}$, Glu$^{23}$ Arg$^{26,34}$ A6c$^{32}$ Lys$^{36}$(N$^\epsilon$-tetradecanoyl))hGLP-1(7-36)NH$_2$ (SEQ ID NO:292)
Example 250: (Aib$^{8,35}$, Glu$^{35}$Arg$^{26,34}$ A6c$^{32}$ Lys$^{36}$(N$^\epsilon$-hexadecanoyl))hGLP-1(7-36)NH$_2$ (SEQ ID NO:293)
Example 251: (Aib$^{8,24,35}$, Glu$^{23}$, Arg$^{26,34}$, A6c$^{32}$, Lys$^{36}$(N$^\epsilon$-octanoyl))hGLP-1(7-36)NH$_2$ (SEQ ID NO:294)
Example 252: (Aib$^{8,24,35}$, Glu$^{23}$, Arg$^{26,34}$, A6c$^{32}$, Lys$^{36}$(N$^\epsilon$-tetradecanoyl))hGLP-1(7-36)NH$_2$ (SEQ ID NO:295)
Example 253: (Aib$^{8,24,35}$, Glu$^{23}$, Arg$^{26,34}$, A6c$^{32}$, Lys$^{36}$(N$^\epsilon$-hexadecanoyl))hGLP-1(7-36)NH$_2$ (SEQ ID NO:296)
Example 254: (Aib$^{8,24,30,35}$, Glu$^{23}$, Arg$^{26,34}$, A6c$^{32}$, Lys$^{36}$ (N$^\epsilon$-octanoyl))hGLP-1 (7-36)NH$_2$ (SEQ ID NO:297)
Example 255: (Aib $^{24,30,35}$, Glu$^{23}$, Arg$^{26,34}$ A6c$^{32}$, Lys$^{36}$(N$^\epsilon$-tetradecanoyl))hGLP-1(7-36)NH$_2$ (SEQ ID NO:298)
Example 256: (Aib$^{8,24,30,35}$, Glu$^{23}$, Arg$^{26,34}$, A6c$^{32}$, Lys$^{36}$ (N$^\epsilon$-hexadecanoyl hGLP-1(7-36)NH$_1$ (SEQ ID NO:299)
Example 257: ((N$^\alpha$-HEPES-His)$^7$, Aib$^{35}$)hGLP-1(7-36)NH$_2$ (SEQ ID NO:300)
Example 258: ((N$^\alpha$-HEPES-His)$^7$, β-Ala$^{35}$)hGLP-1(7-36)NH$_2$ (SEQ ID NO:301)
Example 259: ((N$^\alpha$-HEPES-His)$^7$, Aib$^8$, β-Ala$^{35}$)hGLP-1(7-36)NH$_2$ (SEQ ID NO:302)
Example 260: ((N$^\alpha$-HEPA-His)$^7$, Aib$^{35}$)hGLP-1(7-36)NH$_2$ (SEQ ID NO:303)
Example 261: ((N$^\alpha$-HEPA-His)$^7$, β-Ala$^{35}$)hGLP-1(7-36)NH$_2$ (SEQ ID NO:304)
Example 262: ((N$^\alpha$-HEPA-His)$^7$, Aib$^8$, β-Ala$^{35}$)hGLP-1(7-36)NH$_2$ (SEQ ID NO:305)
Example 263: ((N$^\alpha$-tetradecanoyl-His)$^7$, Aib$^{35}$)hGLP-1(7-36)NH$_2$ (SEQ ID NO:306)
Example 264: ((N$^\alpha$-tetradecanoyl-His)$^7$, β-Ala$^{35}$)hGLP-1(7-36)NH$_2$ (SEQ ID NO:307)
Example 265: ((N$^\alpha$-tetradecanoyl-His)$^7$, Aib$^{8,35}$)hGLP-1(7-36)NH$_2$ (SEQ ID NO:308)
Example 266: ((N$^\alpha$-tetradecanoyl-His)$^7$, Aib$^8$, β-Ala$^{35}$) hGLP-1(7-36)NH$_2$ (SEQ ID NO:309)
Example 267: (N$^\alpha$-tetradecanoyl-His)$^7$, Arg$^{26,34}$, Aib$^{35}$) hGLP-1(7-36)NH$_2$ (SEQ ID NO:310)
Example 268: ((N$^\alpha$-tetradecanoyl-His)$^7$, Arg$^{26,34}$, β-Ala$^{35}$)hGLP-1(7-36)NH$_2$ (SEQ ID NO:311)
Example 269: ((N$^\alpha$-tetradecanoyl-His)$^7$, Aib$^{8,35}$, Arg$^{26,34}$) hGLP-1 (7-36)NH$_2$ (SEQ ID NO:312)
Example 270: ((N$^\alpha$-tetradecanoyl-His)$^7$, Aib$^8$, Arg$^{26,34,35}$) hGLP-1(7-36)NH$_2$ (SEQ ID NO:313)
Example 271: ((N$^\alpha$-tetradecanoyl-His)$^7$, Arg$^{25,26,34}$, β-Ala$^{35}$)hGLP-1(7-36)NH$_2$ (SEQ ID NO:314)
Example 272: ((N$^\alpha$-tetradecanoyl-His)$^7$, Aib$^{8,35}$, Arg$^{25,26,34}$)hGLP-1(7-36)NH$_2$ (SEQ ID NO:315)
Example 273: ((N$^\alpha$-tetradecanoyl-His)$^7$, Aib$^8$, Arg$^{25,26,34}$, β-Ala$^{35}$)hGLP-1(7-36)NH$_2$ (SEQ ID NO:316)

Example 274: (Aib$^{8,35}$, Lys$^{26}$(N$^\alpha$-octanesulfonyl), Arg$^{34}$) hGLP-1(7-36)NH$_2$ (SEQ ID NO:317)

Example 275: (Aib$^{8,35}$, Lys$^{26}$ (N-dodecanesulfonyl), Arg$^{34}$) hGLP-1 (7-36)NH$_2$ (SEQ ID NO:318)

Example 276: (Aib$^{8,35}$, Lys$^{26}$(N$^\alpha$-hexadecanesulfonyl), Arg$^{34}$)hGLP-1(7-36)NH$_2$ (SEQ ID NO:319)

Example 277: (Aib$^{8,35}$, Arg$^{26}$, Lys$^{34}$(N$^\epsilon$-octanesulfonyl)) hGLP-1(7-36)NH$_2$ (SEQ ID NO:320)

Example 278: (Aib$^{8,35}$, Arg$^{26}$, Lys$^{34}$(dodecanesulfonyl)) hGLP-1(7-36)NH$_2$ (SEQ ID NO:21

Example 279: (Aib$^{8,35}$, Arg$^{26}$, Lys$^{34}$(N$^\epsilon$-hexadecanesulfonyl))hGLP-1(736)NH$_2$ (SEQ ID NO:322)

Example 280: (Aib$^{8,35}$, Arg$^{26,34}$, Lys$^{36}$(N$^\epsilon$-octanesulfonyl)) hGLP-1(7-36)NH$_2$ (SEQ ID NO:323)

Example 281: (Aib$^{8,35}$ Arg$^{26,34}$ Lys$^{36}$(N$^\epsilon$-hexadecanesulfonyl))hGLP-1(7-36)NH$_2$ (SEQ ID NO:324)

Example 282: (Aib$^{8,35}$, Asp$^{26}$(1-(4-decylpiperazine)), Arg$^{34}$)hGLP-1 (7-36)NH$_2$ (SEQ ID NO:325)

Example 283: (Aib$^{8,35}$, Asp$^{26}$(1-(4-dodecylpiperazine)), Arg$^{34}$)hGLP-1(7-36)NH$_2$ (SEQ ID NO:326)

Example 284: (Aib$^{8,35}$, Asp$^{26}$(1-(4-tetradecylpiperazine)), Arg$^{34}$)hGLP-1(7-36)NH$_2$ (SEQ ID NO:327)

Example 285: (Aib$^{8,35}$, Asp$^{26}$(1-(4-hexadecylpiperazine)), Arg$^{34}$)hGLP-1(7-36)NH$_2$ (SEQ ID NO:328)

Example 286: (Aib$^{8,35}$, Arg$^{26}$, Asp$^{34}$(1-(4-decylpiperazine)))hGLP-1(7-36)NH$_2$ (SEQ ID NO:329)

Example 287: (Aib$^{8,35}$, Arg$^{26}$ Asp$^{34}$(2-(4-dodecylpiperazine)))hGLP-1(7-36)NH$_2$ (SEQ ID NO:330)

Example 288: (Aib$^{8,35}$, Arg$^{26}$ Asp$^{34}$(1-(4-tetradecylpiperazine)))hGLP-1(7-36)NH$_2$ (SEQ ID NO:331)

Example 289: (Aib$^{8,35}$, Arg$^{26}$, Asp$^{34}$(1-(4-hexadecylpiperazine)))hGLP-1 (7-36)NH$_2$ (SEQ ID NO:332)

Example 290: (Aib$^{8,35}$, Arg$^{26,34}$, Asp$^{36}$(1-(4-decylpiperazine)))hGLP-1(7-36)NH$_2$ (SEQ ID NO:333)

Example 291: (Aib$^{8,35}$, Arg$^{26,34}$ Asp$^{36}$(1-(4-dodecylpiperazine)))hGLP-1(7-36)NH$_2$ (SEQ ID NO:334)

Example 292: (Aib$^{8,35}$, Arg$^{26,34}$, Asp$^{36}$(1-(4-hexadecylpiperazine)))hGLP-1(7-36)NH$_2$ (SEQ ID NO:335)

Example 293: (Aib$^{8,35}$, Arg$^{26,34}$ Asp$^{38}$ (1-(4-decylpiperazine)))hGLP-1(7-38)NH$_2$ (SEQ ID NO:336)

Example 294: (Aib$^{8,35}$, Arg$^{26,34}$, Asp$^{38}$(1-(4-dodecylpiperazine)))hGLP-1(7-38)NH$_2$ (SEQ ID NO:337)

Example 295: (Aib$^{8,35}$, Arg$^{26,34}$, Asp$^{38}$(1-(4-tetradecylpiperazine)))hGLP-1(7-38)NH$_2$ (SEQ ID NO:338)

Example 296: (Aib$^{8,35}$, Arg$^{26,34}$, Asp$^{38}$(1-(4-hexadecylpiperazine)))hGLP-1(7-38)NH$_2$ (SEQ ID NO:339)

Example 297: (Aib$^{8,35,37}$, Arg$^{26,34}$, Asp$^{38}$(1-(4-decylpiperazine)))hGLP-1(7-38)NH$_2$ (SEQ ID NO:340)

Example 298: (Aib$^{8,35,37}$, Arg$^{26,34}$, Asp$^{38}$(1-(4-dodecylpiperazine)))hGLP-1(7-38)NH$_2$ (SEQ ID NO:341)

Example 299: (Aib$^{8,35,37}$, Arg$^{26,34}$, Asp$^{38}$(1-(4-tetradecylpiperazine)))hGLP-1(7-38)NH$_2$ (SEQ ID NO:342)

Example 300: (Aib$^{8,35,37}$ Arg$^{26,34}$, Asp$^{38}$(1-(4-hexadecylpiperazine)))hGLP-1(7-38)NH$_2$ (SEQ ID NO:343)

Example 301: (Aib$^{8,35}$, Arg $^{25,34}$, Asp$^{26}$(1-(4-decylpiperazine)))hGLP-1(7-36)NH$_2$ (SEQ ID NO:344)

Example 302: (Aib$^{8,35}$, Arg$^{25,34}$, Asp$^{26}$(1-(4-dodecylpiperazine)))hGLP-1(7-36)NH$_2$ (SEQ ID NO:345)

Example 303: (Aib$^{8,35}$, Arg$^{25,34}$, Asp$^{26}$(1-(4-tetradecylpiperazine)))hGLP-1(7-36)NH$_2$ (SEQ ID NO:346)

Example 304: (Aib$^{8,35}$, Arg$^{25,34}$, Asp$^{26}$(1-(4-hexadecylpiperazine)))hGLP-1(7-36)NH$_2$ (SEQ ID NO:347)

Example 305: (Aib$^{8,35}$, Arg$^{25,26}$, Asp$^{34}$(1-(4-decylpiperazine)))hGLP-1(7-36)NH$_2$ (SEQ ID NO:348)

Example 306: (Aib$^{8,35}$, Arg$^{25,26}$, Asp$^{34}$(1-(4-dodecylpiperazine)))hGLP-1(7-36)NH$_2$ (SEQ ID NO:349)

Example 307: (Aib$^{8,35}$, Arg$^{25,26}$, Asp$^{34}$(1-(4-tetradecylpiperazine)))hGLP-1(7-36)NH$_2$ (SEQ ID NO:350)

Example 308: (Aib$^{8,35}$, Arg$^{25,26}$, Asp$^{34}$(1-(4-hexadecylpiperazine)))hGLP-1(7-36)NH$_2$ (SEQ ID NO:351)

Example 309: (Aib$^{8,35}$, Arg$^{25,26,34}$, Asp$^{36}$(1-(4-decylpiperazine)))hGLP-1(7-36)NH$_2$ (SEQ ID NO:352)

Example 310: (Aib$^{8,35}$ Arg$^{25,26,34}$ Asp$^{36}$(1-(4-dodecylpiperazine)))hGLP-1(7-36)NH$_2$ (SEQ ID NO:353)

Example 311: (Aib$^{8,35}$, Arg$^{25,26,34}$, Asp$^{36}$(1-(4-tetradecylpiperazine)))hGLP-1(7-36)NH$_2$ (SEQ ID NO:354)

Example 312: (Aib$^{8,35}$, Arg$^{25,26,34}$, Asp$^{36}$(1-(4-hexadecylpiperazine)))hGLP-1(7-36)NH$_2$ (SEQ ID NO:355)

Example 313: (Aib$^{8,35}$, Arg$^{25,26,34}$ Asp$^{38}$(1-(4-decylpiperazine)))hGLP-1(7-38)NH$_2$ (SEQ ID NO:356)

Example 314: (Aib$^{8,35}$, Arg$^{25,26,34}$, Asp$^{38}$(1-(4-dodecylpiperazine)))hGLP-1(7-38)NH$_2$ (SEQ ID NO:357)

Example 315: (Aib$^{8,35}$, Arg$^{25,26,34}$, Asp$^{38}$(1-(4-tetradecylpiperazine)))hGLP-1(7-38)NH$_2$ (SEQ ID NO:358)

Example 316: (Aib$^{8,35}$, Arg$^{25,26,34}$, Asp$^{38}$(1-(4-hexadecylpiperazine)))hGLP-1(7-38)NH$_2$ (SEQ ID NO:359)

Example 317: (Aib$^{8,35,37}$, Arg$^{25,26,34}$ Asp$^{38}$(1-(4-decylpiperazine)))hGLP-1(7-38)NH$_2$ (SEQ ID NO:360)

Example 318: (Aib$^{8,35,37}$, Arg$^{25,26,34}$, Asp$^{38}$(1-(4-dodecylpiperazine)))hGLP-1(7-38)NH$_2$ (SEQ ID NO:361)

Example 319: (Aib$^{8,35,37}$, Arg$^{25,26,34}$ Asp$^{38}$(1-(4-tetradecylpiperazine)))hGLP-1(7-38)NH$_2$ (SEQ ID NO:362)

Example 320: (Aib$^{8,35,37}$, Arg$^{25,26,34}$, Asp$^{38}$(1-(4-hexadecylpiperazine)))hGLP-1(7-38)NH$_2$ (SEQ ID NO:363)

Example 321: (Aib$^{8,35}$, Arg$^{26,34}$, Glu$^{36}$(1-dodecylamino)) hGLP-1 (7-36)NH, (SEQ ID NO:364)

Example 322: (Aib$^{8,35}$, Glu$^{26}$(1-dodecylamino), Arg$^{34}$) hGLP-1(7-36)NH$_2$ (SEQ ID NO:365)

Example 323: (Aib$^{8,35}$, Arg$^{26}$, Glu$^{34}$(1-dodecylamino)) hGLP-1(7-36)NH$_2$ (SEQ ID NO:366)

Example 324: (Aib$^{8,35,37}$ Arg$^{26,24}$, Glu$^{38}$(1-dodecylamino)) hGLP-1(7-38)NH$_2$ (SEQ ID NO:367)

Example 325: (Aib$^{8,35}$, Arg$^{34}$, Lys$^{26}$(N$^\epsilon$-(2-(4-decyl-1-piperazine)-acetyl)))hGLP-1 (7-36)NH$_2$ (SEQ ID NO:368)

Example 326: (Aib$^{8,35}$, Arg$^{34}$, Lys$^{26}$(N$^\epsilon$-(2-(4-dodecyl-1-piperazine)-acetyl)))hGLP-1 (7-36)NH$_2$ (SEQ ID NO:369)

Example 327: (Aib$^{8,35}$, Arg$^{34}$, Lys$^{26}$(N$^\epsilon$(2-(4-tetradecyl-1-piperazine)-acetyl)))hGLP-1(7-36)NH$_2$ (SEQ ID NO:370)

Example 328: (Aib$^{8,35}$, Arg$^{34}$, Lys$^{26}$(N$^\epsilon$(4-hexadecyl-1-piperazine)-acetyl)))hGLP-1 (7-36)NH$_2$ (SEQ ID NO:371)

Example 329: (Aib$^{8,35}$, Arg$^{26}$, Lys$^{34}$(N$^\epsilon$(2-(4-decyl-1-piperazine)-acetyl)))hGLP-1(7-36)NH$_2$ (SEQ ID NO:372)

Example 330: (Aib$^{8,35}$, Arg$^{26}$, Lys$^{34}$(N$^\epsilon$(2-(4-dodecyl-1-piperazine)-acetyl)))hGLP-1(7-36)NH$_2$ (SEQ ID NO:373)

Example 331: (Aib$^{8,35}$, Arg$^{26}$, Lys$^{34}$(N$^\epsilon$(2-(4-tetradecyl-1-piperazine)-acetyl)))hGLP-1(7-36)NH$_2$ (SEQ ID NO:374)

Example 332: (Aib$^{8,35}$, Arg$^{26}$, Lys$^{34}$ (N$^\epsilon$-(2-(4-hexadecyl-1-piperazine)-acetyl)))hGLP-1(7-36)NH$_2$ (SEQ ID NO:375)

Example 333: (Aib$^{8,35}$, Arg$^{26,34}$, Lys$^{36}$(N$^\epsilon$-(2(4-decyl-1-piperazine)-acetyl)))hGLP-1(7-36)NH$_2$ (SEQ ID NO:376)

Example 334: (Aib$^{8,35}$, Arg$^{26}$,34, Lys$^{36}$(N$^\epsilon$-(2-(4-dodecyl-1-piperazine)-acetyl)))hGLP-1(7-36)NH$_2$ (SEQ ID NO:377)

Example 335: (Aib$^{8,35}$, Arg$^{26,34}$, Lys$^{36}$(N$^\epsilon$-(2-(4-hexadecyl-1-piperazine)-acetyl)))hGLP-1(7-36)NH$_2$ (SEQ ID NO:378)

Example 336: (Aib$^{8,35}$, Arg$^{26,34}$, Lys$^{38}$(N$^\epsilon$-(2-(4-decyl-1-piperazine)-acetyl)))hGLP-1(7-38)N H$_2$ (SEQ ID NO:379)

Example 337: (Aib$^{8,35}$, Arg$^{26,34}$, Lys$^{3}$(N$^\epsilon$-(2-(4-dodecyl-1-piperazine)-acetyl)))hGLP-1(7-38)NH$_2$ (SEQ ID NO:380)

Example 338: (Aib$^{8,35}$, Arg$^{26,34}$ Lys$^{38}$(N$^\epsilon$-(2-(4-tetradecyl-1-piperazine)-acetyl)))hGLP-1(7-38)NH$_2$(SEQ ID NO:381)

Example 339: (Aib$^{8,35}$, Arg$^{26,34}$, Lys$^{38}$(N$^\epsilon$-(2-(4-hexadecyl-1-piperazine)-acetyl)))hGLP-1(7-38)NH$_2$ (SEQ ID NO:382)

Example 340: (Aib$^{8,35,37}$, Arg$^{26,34}$, Lys$^{38}$(N$^\epsilon$-(2-(4-decyl-1-piperazine)-acetyl)))hGLP-1 (7-38)NH$_2$ (SEQ ID NO:383)

Example 341: (Aib$^{8,35,37}$, Arg$^{26,34}$, Lys$^{38}$(N$^\epsilon$-(2-(4-dodecyl-1-piperazine)-acetyl)))hGLP-1(7-38)NH$_2$ (SEQ ID NO:384)

Example 342: (Aib$^{8,35,37}$, Arg$^{26,34}$, Lys$^{38}$(N$^\epsilon$-(2-(4-tetradecyl-1-piperazine)-acetyl)))hGLP-1 (7-8)NH$_2$ (SEQ ID NO:385)

Example 343: (Aib$^{8,35,37}$, Arg$^{26,34}$, Lys$^{38}$(N$^\epsilon$-(2-(4-hexadecyl-1-piperazine)-acetyl)))hGLP-1 (7-38)NH$_2$ (SEQ ID NO:386)

Example 344: Aib$^{8,35}$, Arg$^{25,34}$, Lys$^{26}$ (N$^\epsilon$-(2-(4-decyl-1-piperazine)-acetyl)))hGLP-1 (7-36)NH$_2$ (SEQ ID NO:387)

Example 344: (Aib$^{8,35}$, Arg$^{25,34}$, Lys$^{26}$(N$^\epsilon$(2-_4-dodecyl-1-piperazine)-acetyl)))hGLP)-1(7-36)NH$_2$(SEQ ID NO:387)

Example 345: (Aib$^{8,35}$, Arg$^{25,34}$, Lys$^{26}$(N$^\epsilon$(2-(4-dodecyl-1-piperazine)-acetyl)))hGLP-1(7-36)NH$_2$ (SEQ ID NO:388)

Example 346: (Aib$^{8,35}$, Arg$^{25,34}$, Lys$^{26}$(N$^\epsilon$(2-(4-tetradecyl-1-piperazine)-acetyl)))hGLP-1(7-36)NH$_2$ (SEQ ID NO:389)

Example 347: (Aib$^{8,35}$, Arg$^{25,34}$, Lys$^{26}$(N$^\epsilon$(2-(4-hexadecyl-1-piperazine)-acetyl)))hGLP-1 (7-36)NH$_2$ (SEQ ID NO:390)

Example 348: (Aib$^{8,35}$, Arg$^{25,26}$, Lys$^{34}$ (N$^\epsilon$-(2-(4-decyl-1-piperazine)-acetyl)))hGLP-1(7-36)NH$_2$ (SEQ ID NO:391)

Example 349: (Aib$^{8,35}$, Arg$^{25,26}$, Lys$^{34}$ (N$^\epsilon$-(2-(4-dodecyl-1-piperazine)-acetyl)))hGLP-1(7-36)NH$_2$ (SEQ ID NO:392)

Example 350: (Aib$^{8,35}$, Arg$^{25,26}$, Lys$^{34}$(N$^\epsilon$-(2-(4-tetradecyl-1-piperazine)-acetyl)))hGLP-1 (7-36)NH$_2$ (SEQ ID NO:393)

Example 351: (Aib$^{8,35}$, Arg$^{25,26}$, Lys$^{34}$(N$^\epsilon$-(2-(4-hexadecyl-1-piperazine)-acetyl)))hGLP-1(7-36)NH$_2$ (SEQ ID NO:394)

Example 352: (Aib$^{8,35}$, Arg$^{25,26,34}$ Lys$^{36}$(N$^\epsilon$-(2-(4-decyl-1-piperazine)-acetyl)))hGLP-1(7-36)NH$_2$ (SEQ ID NO:395)

Example 353: (Aib$^{8,35}$, Arg$^{25,26,34}$ Lys$^{36}$(N$^\epsilon$-(2-(4-dodecyl-1-piperazine)-acetyl)))hGLP-1 (7-36)NH$_2$ (SEQ ID NO:396)

Example 354: (Aib$^{8,35}$, Arg$^{25,26,34}$ Lys$^{36}$(N$^\epsilon$-(2-(4-tetradecyl-1-piperazine)-acetyl)))hGLP-1(7-36)NH$_2$ (SEQ ID NO:397)

Example 355: (Aib$^{8,35}$, Arg$^{25,26,34}$ Lys$^{36}$(N$^\epsilon$-(2-(4-hexadecyl-1-piperazine)-acetyl)))hGLP-1(7-36)NH$_2$ (SEQ ID NO:398)

Example 356: (Aib$^{8,35}$, Arg$^{25,26,34}$ Lys$^{38}$(N$^\epsilon$-(2(4-decyl-1-piperazine)-acetyl)))hGLP-1(7-38)NH$_2$ (SEQ ID NO:399)

Example 357: (Aib$^{8,35}$, Arg$^{25,26,34}$, Lys$^{38}$(N$^\epsilon$-(2-(4-dodecyl-1-piperazine)-acetyl)))hGLP-1(7-38)NH$_2$ (SEQ ID NO:400)

Example 358: (Aib$^{8,35}$, Arg$^{25,26,34}$, Lys$^{38}$(N$^\epsilon$-(2-(4-tetradecyl-1-piperazine)-acetyl)))GLP-1(7-38)NH$_2$ (SEQ ID NO:401)

Example 359: (Aib$^{8,35}$, Arg$^{25,26,34}$, Lys$^{38}$(N$^\epsilon$-(2-(4-hexadecyl-1-piperazine)-acetyl)))hGLP-1(7-38)NH$_2$ (SEQ ID NO:402)

Example 360: (Aib$^{8,35,37}$, Arg$^{25,26,34}$, Lys$^{38}$(N$^\epsilon$-(2-(4-decyl-1-piperazine)-acetyl)))hGLP-1(7-38)NH$_2$ (SEQ ID NO:403)

Example 361: (Aib$^{8,35,37}$, Arg$^{25,26,34}$, Lys$^{38}$(N$^\epsilon$-(2-(4-dodecyl-1-piperazine)-acetyl)))hGLP-1(7-38)NH$_2$ (SEQ ID NO:404)

Example 362: (Aib$^{8,35,37}$, Arg$^{25,26,34}$, Lys$^{38}$(N$^\epsilon$-(2-(4-tetradecyl-1-piperazine)-acetyl)))hGLP-1(7-38)NH$_2$ (SEQ ID NO:405)

Example 363: (Aib$^{8,35,37}$, Arg$^{25,26,34}$, Lys$^{38}$(N$^\epsilon$-(2-(4-hexadecyl-1-piperazine)-acetyl)))hGLP-1(7-38)NH$_2$ (SEQ ID NO:406)

Example 364: (Aib$^{8,35}$, Arg$^{26,34}$, Lys$^{36}$(N$^\epsilon$-decanoyl))hGLP-1(7-36)OH (SEQ ID NO:407)

Example 365: (Aib$^{8,35}$, Lys$^{25}$, Arg$^{26,34}$, Lys$^{36}$(N$^\epsilon$-decanoyl))hGLP-1(7-36)OH (SEQ ID NO:408)

Example 370: (Aib$^{8,33}$, Arg$^{26,34}$, Ava$^{37}$, Ado$^{39}$)hGLP-1(7-38)NH$_2$ (SEQ ID NO:409)

Example 371: (Aib$^{8,35}$, Arg$^{26,34}$ Asp$^{37}$ Ava$^{38}$ Ado$^{39}$)hGLP-1(7-39)NH$_2$ (SEQ ID NO:27)

Example 372: (Aib$^{8,35}$, Arg$^{26,34}$, Aun$^{37}$)hGLP-1(7-37)NH$_2$ (SEQ ID NO:28)

Example 373: (Aib$^{8,17,35}$)hGLP-1(7-36)NH$_2$ (SEQ ID NO:29)

Example 374: (Aib$^{8}$, Arg$^{26,34}$, β-Ala$^{35}$, D-Asp$^{37}$ Ava$^{38}$, Aun$^{39}$)hGLP-1(7-39)NH$_2$ (SEQ ID NO:30)

Example 375: (Gly$^{8}$, β-Ala$^{35}$)hGLP-1(7-36)NH$_2$ (SEQ ID NO:31)

Example 376: (Ser$^{8}$, β-Ala$^{35}$)hGLP-1(7-36)NH$_2$ (SEQ ID NO:32)

Example 377: (Aib$^{8}$, Glu$^{22,23}$ Ala$^{35}$)hGLP-1(7-36)NH$_2$ (SEQ ID NO:33)

Example 378: (Gly$^{8}$, Aib$^{35}$)hGLP-1(7-36)NH$_2$ (SEQ ID NO:34)

Example 379: (Aib⁸, Lys¹⁸, β-Ala³⁵)hGLP-1(7-36)NH₂ (SEQ ID NO: 35)
Example 380: (Aib⁸, Leu²⁷, β-Ala³⁵)hGLP-1(7-36)NH₂ (SEQ ID NO:36)
Example 381: (Aib⁸, Lys³³, β-Ala³⁵)hGLP-1(7-36)NH₂ (SEQ ID NO:37)
Example 382: (Aib⁸, Lys⁸, Leu²⁷, β-Ala³⁵)hGLP-1(7-36) NH₂ (SEQ ID NO:38)
Example 383: (Aib⁸, D-Arg³⁶)hGLP-1 (7-36)NH₂ (SEQ ID NO:39)
Example 384: (Aib⁸, β-Ala³⁵, D-Arg³⁷)hGLP-1(7-37)NH₂ (SEQ ID NO:40)
Example 385: (Aib⁸,²⁷, β-Ala³⁵)hGLP-1 (7-36)NH₂ (SEQ ID NO:41)
Example 386: (Aib⁸,²⁷, β-Ala³⁵,³⁷ Arg³⁸)hGLP-(7-38)NH₂ (SEQ ID NO:42)
Example 387: (Aib⁸,²⁷, β-Ala³⁵,³⁷ Arg³⁸,³⁹)hGLP-1(7-39) NH₂(SEQ ID NO:43)
Example 388: (Aib⁸, Lys¹⁸,²⁷, β-Ala³⁵)hGLP-1(7-36)NH₂ (SEQ ID NO:44)
Example 389: (Aib⁸, Lys²⁷, β-Ala³⁵)hGLP-1(7-36)NH₂ (SEQ ID NO:45)
Example 390: (Aib⁸, β-Ala³⁵, Arg³⁸)hGLP-1(7-38)NH₂ (SEQ ID NO:46)
Example 391: (Aib⁸, Arg²⁶,³⁴, β-Ala³⁵)hGLP-1(7-36)NH₂ (SEQ ID NO:47)
Example 392: (Aib⁸, D-Arg³⁵)hGLP-1(7-36)NH₂ (SEQ ID NO:48)
Example 393: (Aib⁸, β-Ala³⁵, Arg³⁷)hGLP-1(7-37)NH₂ (SEQ ID NO:49)
Example 394: (Aib⁸, Phe³¹, β-Ala³⁵)hGLP-1(7-36)NH₂ (SEQ ID NO:50)
Example 395: (Aib⁸,³⁵, Phe³¹, β-Ala³⁵)hGLP-1(7-36)NH₂ (SEQ ID NO:51)
Example 396: (Aib⁸,³⁵, Nal³¹)hGLP-1(7-36)NH₂ (SEQ ID NO:52)
Example 397: (Aib⁸,³⁵, Nal²⁸,³¹)hGLP-1(7-36)NH₂ (SEQ ID NO:53)
Example 398: (Aib⁸,³⁵, Arg²⁶,³⁴, Nal³¹)hGLP-1(7-36)NH₂ (SEQ ID NO:54)
Example 399: (Aib⁸,³⁵, Arg²⁶,³⁴ Phe³¹)hGLP-1(7-36)NH₂ (SEQ ID NO:55)
Example 400: (Aib⁸,³⁵, Nal¹⁹,³¹)hGLP-1(7-36)NH₂ (SEQ ID NO:56)
Example 401: (Aib⁸,³⁵, Nal¹²,³¹)hGLP-1 (7-36)NH₂ (SEQ ID NO:57)
Example 402: (Aib⁸,³⁵, Lys³⁶(Nᵉ-decanoyl))hGLP-1(7-36) NH₂ (SEQ ID NO:58)
Example 403: (Aib⁸,³⁵, Arg³⁴, Lys²⁶(Nᵉ-decanoyl))hGLP-1 (7-36)NH₂ (SEQ ID NO:59)
Example 404: (Aib⁸,³⁵, Arg²⁶,³⁴, Lys³⁶(Nᵉ-dodecanoyl)) hGLP-1(7-36)NH₂ (SEQ ID NO:60)
Example 405: (Aib⁸, β-Ala³⁵, Ser³⁷(O-decanoyl))hGLP-1 (7-37)NH₂ (SEQ ID NO:61)
Example 406: (Aib⁸,²⁷, β-Ala³⁵,³⁷, Arg³⁸, Lys³⁷(N-octanoyl))hGLP-1(7-39)NH₂ (SEQ ID NO:62)
Example 407: (Aib⁸, Arg²⁶,³⁴, β-Ala³⁵, Lys³⁷(Nᵉ-octanoyl)) hGLP-1(7-37)NH₂ (SEQ ID NO:63)
Example 408: (Aib⁸, Arg²⁶,³⁴, β-Ala³⁵, Lys³⁷(Nᵉ-decanoyl)) hGLP-1(7-37)NH₂ (SEQ ID NO:64)
Example 409: (Aib⁸, Arg²⁶,³⁴, β-Ala³⁵, Lys³⁷(Nᵉ-6-tetradecanoyl))hGLP-1(7-37)NH₂ (SEQ ID NO:65)
Example 410: (Aib⁸, Arg²⁶,³⁴, β-Ala³⁵, Lys³⁷(Nᵉ-dodecanoyl))hGLP-1(7-37)NH₂ (SEQ ID NO:410)
Example 411: (Aib⁸, Arg²⁶,³⁴, β-Ala³⁵, Lys³⁷(Nᵉ-dodecanoyl))hGLP-1(8-37)NH₂ (SEQ ID NO:411)

Physical data for a representative sampling of the compounds exemplified herein are given in Table 1.

TABLE 1

| Example Number | Mol. Wt. Expected | Mol. Wt. MS(ES) | Purity (HPLC) |
|---|---|---|---|
| 24 | 3351.8 | 3352.2 | 88% |
| 26 | 3340.17 | 3340.9 | 99% |
| 27 | 3353.81 | 3353.9 | 99% |
| 29 | 3353.81 | 3353.9 | 99% |
| 45 | 3352.6 | 3352.5 | 97% |
| 51 | 3326.74 | 3326.6 | 99% |
| 78 | 3395.81 | 3395.5 | 96% |
| 136 | 3494 | 3494 | 99% |
| 364 | 3523.02 | 3523.6 | 99% |
| 365 | 3580.13 | 3580.3 | 95% |
| 369 | 3677.25 | 3677 | 97% |
| 370 | 3692.28 | 3692.4 | 98% |
| 371 | 3807.37 | 3807.3 | 98% |
| 372 | 3579.11 | 3579.7 | 97.90% |
| 373 | 3337.81 | 3338.5 | 94% |
| 374 | 3779.3 | 3779.5 | 94% |
| 375 | 3297.7 | 3297.5 | 99% |
| 376 | 3327.7 | 3327.4 | 98% |
| 377 | 3398.8 | 3398.7 | 97.50% |
| 378 | 3311.6 | 3311 | 93% |
| 379 | 3366.85 | 3366.5 | 97% |
| 380 | 3309.8 | 3309.4 | 99% |
| 381 | 3354.8 | 3354.5 | 97.70% |
| 382 | 3350.9 | 3350.3 | 97.20% |
| 383 | 3311.73 | 3310.7 | 92% |
| 384 | 3481.95 | 3481.3 | 94.30% |
| 385 | 3281.76 | 3281.6 | 98% |
| 386 | 3509.02 | 3509.1 | 99.40% |
| 387 | 3665.2 | 3665.1 | 99% |
| 388 | 3365.91 | 3365 | 97% |
| 389 | 3324.79 | 3324.2 | 95% |
| 390 | 3539 | 3539.2 | 93% |
| 391 | 3381.74 | 3381.3 | 97% |
| 392 | 3410.89 | 3409.8 | 99% |
| 393 | 3481.95 | 3481.1 | 90% |
| 394 | 3286.76 | 3286.2 | 99.20% |
| 395 | 3300.76 | 3299.4 | 93% |
| 396 | 3350.81 | 3349.4 | 99% |
| 397 | 3400.87 | 3400.1 | 99% |
| 398 | 3406.84 | 3406.4 | 99% |
| 399 | 3356.77 | 3356.6 | 99% |
| 400 | 3384.87 | 3384.43 | 94% |
| 401 | 3400.87 | 3401.3 | 99% |
| 402 | 3466.03 | 3466.9 | 97.40% |
| 403 | 3522.05 | 3522.06 | 93% |
| 404 | 3550.11 | 3550.2 | 98% |
| 405 | 3567.09 | | 99% |
| 406 | 3763.38 | 3763.2 | 95% |
| 407 | 3636.15 | 3635.8 | 99% |
| 408 | 3664.21 | 3663.3 | 99% |
| 409 | 3720.32 | 3719.5 | 99% |
| 410 | 3692.27 | 3691.7 | 99% |
| 411 | 3555.13 | 3554.4 | 99% |

What is claimed is:

1. A compound wherein said compound is [Aib$^{8,35}$]hGLP-1(7-36)NH$_2$ (SEQ ID NO:2), or a pharmaceutically acceptable salt thereof.

2. A composition comprising a compound according to claim 1 or a pharmaceutically acceptable salt thereof and a pharmaceutically acceptable carrier or diluent.

* * * * *

SEQUENCE LISTING

<160> NUMBER OF SEQ ID NOS: 415

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 2

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N-alpha-HEPES-His
      (N-alpha-(4-(2-hydroxyethyl)-1-piperazine-ethanesulfonic
      acid)-histidine)
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 3

Xaa Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Mutagen -continued

```
<220> FEATURE:
<221> NAME/KEY: VARIANT
<222> LOCATION: 1
<223> OTHER INFORMATION: Xaa = Na-HEPA-His
      (N-alpha-(4-(2-hydroxyethyl)-1-piperazineacetyl)-
      histidine)
<220> FEATURE:
<221> NAME/KEY: VARIANT
<222> LOCATION: 2,29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 4

Xaa Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 5

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 6

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30
```

```
<210> SEQ ID NO 7
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 7

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Xaa Xaa Arg
         20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 8

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Xaa Arg Xaa Xaa
         20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 9

His Xaa Glu Gly Thr Phe Thr Ser Asp Val Ser Ser Tyr Leu Glu Gly
```

```
            1               5                  10                 15
Gln Ala Ala Arg Glu Phe Ile Ala Trp Leu Val Arg Xaa Xaa
            20                 25                 30

<210> SEQ ID NO 10
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-dodecanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 10

His Xaa Glu Gly Thr Phe Thr Ser Asp Val Ser Ser Tyr Leu Glu Gly
 1               5                  10                 15

Gln Ala Ala Arg Glu Phe Ile Ala Trp Leu Val Arg Xaa Xaa
            20                 25                 30

<210> SEQ ID NO 11
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa =
     N-epsilon-(2-(4-tetradecyl-1-piperazine)-acetyl)lysine
<220> FEATURE:
<221> NAME/KEY: VARIANT
<222> LOCATION:
<223> OTHER INFORMATION: this sequence has an amidated c-terminus

<400> SEQUENCE: 11

His Xaa Glu Gly Thr Phe Thr Ser Asp Val Ser Ser Tyr Leu Glu Gly
 1               5                  10                 15

Gln Ala Ala Arg Glu Phe Ile Ala Trp Leu Val Arg Xaa Xaa
            20                 25                 30

<210> SEQ ID NO 12
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = 1-(4-tetradecyl-piperazine)asparagine
<220> FEATURE:
<221> NAME/KEY: VARIANT
```

```
<222> LOCATION:
<223> OTHER INFORMATION: this sequence has an amidated c-terminus

<400> SEQUENCE: 12

His Xaa Glu Gly Thr Phe Thr Ser Asp Val Ser Ser Tyr Leu Glu Gly
 1               5                   10                  15

Gln Ala Ala Arg Glu Phe Ile Ala Trp Leu Val Arg Xaa Xaa
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = (1-tetradecylamino)asparagine
<220> FEATURE:
<221> NAME/KEY: VARIANT
<222> LOCATION:
<223> OTHER INFORMATION: this sequence has an amidated c-terminus

<400> SEQUENCE: 13

His Xaa Glu Gly Thr Phe Thr Ser Asp Val Ser Ser Tyr Leu Glu Gly
 1               5                   10                  15

Gln Ala Ala Arg Glu Phe Ile Ala Trp Leu Val Arg Xaa Xaa
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION: 31
<223> OTHER INFORMATION: Xaa = beta-alanine
<220> FEATURE:
<221> NAME/KEY: VARIANT
<222> LOCATION:
<223> OTHER INFORMATION: Xaa = this sequence has a hydroxylated
      c-terminus

<400> SEQUENCE: 14

His Xaa Glu Gly Thr Phe Thr Ser Asp Val Ser Ser Tyr Leu Glu Gly
 1               5                   10                  15

Gln Ala Ala Arg Glu Phe Ile Ala Trp Leu Val Arg Xaa Xaa Xaa
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Mutagen
```

```
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 15

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 16

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Xaa Arg
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2,29
<223> OTHER INFORMATION: Xaa = alpha-aminoisobutyric acid
<220> FEATURE:
<221> NAME/KEY: VARIANT
<222> LOCATION:
<223> OTHER INFORMATION: this sequence has an amidated c-terminus

<400> SEQUENCE: 17

His Xaa Glu Gly Thr Phe Thr Ser Asp Val Ser Ser Tyr Leu Glu Gly
 1               5                  10                  15

Glu Ala Ala Lys Glu Phe Ile Ala Trp Leu Val Lys Xaa Arg
            20                  25                  30

<210> SEQ ID NO 18
<211> LENGTH: 30
<212> TYPE: PRT
<213> ORGANISM: Artificial Sequence
```

```
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 18

His Xaa Glu Gly Thr Phe Thr Ser Asp Val Ser Ser Tyr Leu Glu Gly
 1               5                  10                  15

Gln Xaa Ala Lys Glu Phe Ile Ala Trp Xaa Val Lys Xaa Arg
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2,29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
     acid)
<220> FEATURE:
<221> NAME/KEY: VARIANT
<222> LOCATION:
<223> OTHER INFORMATION: this sequence has an amidated c-terminus

<400> SEQUENCE: 19

His Xaa Glu Gly Thr Phe Thr Ser Asp Val Ser Ser Tyr Leu Glu Gly
 1               5                  10                  15

Glu Ala Ala Lys Glu Phe Ile Ala Trp Xaa Val Lys Xaa Arg
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-alanine
<220> FEATURE:
<221> NAME/KEY: VARIANT
<222> LOCATION:
<223> OTHER INFORMATION: this sequence has an amidated c-terminus

<400> SEQUENCE: 20

His Xaa Glu Gly Thr Phe Thr Ser Asp Val Ser Ser Tyr Leu Glu Gly
 1               5                  10                  15

Glu Ala Ala Lys Glu Phe Ile Ala Trp Leu Val Lys Xaa Arg
            20                  25                  30

<210> SEQ ID NO 21
<211> LENGTH: 30
```

```
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2,29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 21

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 22

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 23

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 24
```

-continued

```
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 24

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Arg Xaa Xaa
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-alanine
<220> FEATURE:
<221> NAME/KEY: VARIANT
<222> LOCATION: 30
<223> OTHER INFORMATION: Xaa = N-epsilon-4-(2-aminoethyl)-1-
      carboxymethyl-piperazine-decanoyl-lysine
<220> FEATURE:
<221> NAME/KEY: VARIANT
<222> LOCATION:
<223> OTHER INFORMATION: this sequence has an amidated c-terminus

<400> SEQUENCE: 25

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 31
<223> OTHER INFORMATION: Xaa = Ava (5-aminovaleric acid)
<220> FEATURE:
<221> NAME/KEY: VARIANT
<222> LOCATION: 32
<223> OTHER INFORMATION: Xaa = Ado (12-aminododecanoic acid)
<220> FEATURE:
```

```
<221> NAME/KEY: VARIANT
<222> LOCATION:
<223> OTHER INFORMATION: this sequence has an amidated c-terminus

<400> SEQUENCE: 26

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Xaa Xaa
            20                  25                  30

<210> SEQ ID NO 27
<211> LENGTH: 33
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = Ava (5-aminovaleric acid)
<220> FEATURE:
<221> NAME/KEY: VARIANT
<222> LOCATION: 33
<223> OTHER INFORMATION: Xaa = Ado (12-aminododecanoic acid)
<220> FEATURE:
<221> NAME/KEY: VARIANT
<222> LOCATION:
<223> OTHER INFORMATION: this sequence has an amidated c-terminus

<400> SEQUENCE: 27

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Asp Xaa
            20                  25                  30

Xaa

<210> SEQ ID NO 28
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 31
<223> OTHER INFORMATION: Xaa = Aun (11-aminoundecanoic acid)

<400> SEQUENCE: 28

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
```

```
<222> LOCATION: 2, 11, 29
<223> OTHER INFORMATION: Xaa = Aib (alpha-aminoisobutyric acid)

<400> SEQUENCE: 29

His Xaa Glu Gly Thr Phe Thr Ser Asp Val Xaa Ser Tyr Leu Glu Gly
 1               5                  10                  15

Gln Ala Ala Lys Glu Phe Ile Ala Trp Leu Val Lys Xaa Arg
             20                  25                  30

<210> SEQ ID NO 30
<211> LENGTH: 33
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 31
<223> OTHER INFORMATION: Xaa = D-Asp
<220> FEATURE:
<221> NAME/KEY: VARIANT
<222> LOCATION: 32
<223> OTHER INFORMATION: Xaa = Ava (5-aminovaleric acid)
<220> FEATURE:
<221> NAME/KEY: VARIANT
<222> LOCATION: 33
<223> OTHER INFORMATION: Xaa = Aun (11-aminoundecanoic acid)

<400> SEQUENCE: 30

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
             20                  25                  30

Xaa

<210> SEQ ID NO 31
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 31

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
             20                  25                  30

<210> SEQ ID NO 32
<211> LENGTH: 30
<212> TYPE: PRT
<213> ORGANISM: Artificial Sequence
<220> FEATURE:
```

```
<223> OTHER INFORMATION: Mutagen
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 32

His Ser Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 33

His Xaa Glu Gly Thr Phe Thr Ser Asp Val Ser Ser Tyr Leu Glu Glu
 1               5                  10                  15

Glu Ala Ala Lys Glu Phe Ile Ala Trp Leu Val Lys Xaa Arg
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 34

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
```

```
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 35

His Xaa Glu Gly Thr Phe Thr Ser Asp Val Ser Lys Tyr Leu Glu Gly
 1               5                  10                  15

Gln Ala Ala Lys Glu Phe Ile Ala Trp Leu Val Lys Xaa Arg
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 36

His Xaa Glu Gly Thr Phe Thr Ser Asp Val Ser Ser Tyr Leu Glu Gly
 1               5                  10                  15

Gln Ala Ala Lys Leu Phe Ile Ala Trp Leu Val Lys Xaa Arg
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 37

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Lys Lys Xaa Arg
            20                  25                  30

<210> SEQ ID NO 38
<211> LENGTH: 30
<212> TYPE: PRT
```

```
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 38

His Xaa Glu Gly Thr Phe Thr Ser Asp Val Ser Lys Tyr Leu Glu Gly
  1               5                  10                  15

Gln Ala Ala Lys Leu Phe Ile Ala Trp Leu Val Lys Xaa Arg
             20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = D-Arg
<220> FEATURE:
<221> NAME/KEY: VARIANT
<222> LOCATION:
<223> OTHER INFORMATION: this sequence has an amidated c-terminus

<400> SEQUENCE: 39

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Xaa
             20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 31
<223> OTHER INFORMATION: Xaa = D-Arg
<220> FEATURE:
<221> NAME/KEY: VARIANT
<222> LOCATION:
<223> OTHER INFORMATION: this sequence has an amidated c-terminus

<400> SEQUENCE: 40

His Xaa Glu Gly Thr Phe Thr Ser Asp Val Ser Ser Tyr Leu Glu Gly
```

-continued

```
                  1               5              10              15

Gln Ala Ala Lys Glu Phe Ile Ala Trp Leu Val Lys Xaa Arg Xaa
             20                  25              30

<210> SEQ ID NO 41
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 21
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 41

His Xaa Glu Gly Thr Phe Thr Ser Asp Val Ser Ser Tyr Leu Glu Gly
 1               5                  10              15

Gln Ala Ala Lys Xaa Phe Ile Ala Trp Leu Val Lys Xaa Arg
             20                  25              30

<210> SEQ ID NO 42
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 21
<223> OTHER INFORMATION: Xaa = Aib (alpha-aminoisobutyric acid)
<220> FEATURE:
<221> NAME/KEY: VARIANT
<222> LOCATION: 29, 31
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 42

His Xaa Glu Gly Thr Phe Thr Ser Asp Val Ser Ser Tyr Leu Glu Gly
 1               5                  10              15

Gln Ala Ala Lys Xaa Phe Ile Ala Trp Leu Val Lys Xaa Arg Xaa Arg
             20                  25              30

<210> SEQ ID NO 43
<211> LENGTH: 33
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 21
<223> OTHER INFORMATION: Xaa = Aib (alpha-aminoisobutyric acid)
<220> FEATURE:
<221> NAME/KEY: VARIANT
<222> LOCATION: 29, 31
<223> OTHER INFORMATION: Xaa = beta-Ala (beta-alanine)
<220> FEATURE:
<221> NAME/KEY: VARIANT
<222> LOCATION:
```

-continued

```
<223> OTHER INFORMATION: this sequence has an amidated c-terminus

<400> SEQUENCE: 43

His Xaa Glu Gly Thr Phe Thr Ser Asp Val Ser Ser Tyr Leu Glu Gly
  1               5                  10                  15

Gln Ala Ala Lys Xaa Phe Ile Ala Trp Leu Val Lys Xaa Arg Xaa Arg
             20                  25                  30

Arg

<210> SEQ ID NO 44
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 44

His Xaa Glu Gly Thr Phe Thr Ser Asp Val Ser Lys Tyr Leu Glu Gly
  1               5                  10                  15

Gln Ala Ala Lys Lys Phe Ile Ala Trp Leu Val Lys Xaa Arg
             20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 45

His Xaa Glu Gly Thr Phe Thr Ser Asp Val Ser Ser Tyr Leu Glu Gly
  1               5                  10                  15

Gln Ala Ala Lys Lys Phe Ile Ala Trp Leu Val Lys Xaa Arg
             20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
```

```
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 46

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg Gly Arg
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 47

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = D-Arg
<220> FEATURE:
<221> NAME/KEY: VARIANT
<222> LOCATION:
<223> OTHER INFORMATION: this sequence has an amidated c-terminus

<400> SEQUENCE: 48

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 49
<211> LENGTH: 31
<212> TYPE: PRT
<213> ORGANISM: Artificial Sequence
<220> FEATURE:
```

```
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 49

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg Arg
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 50

His Xaa Glu Gly Thr Phe Thr Ser Asp Val Ser Ser Tyr Leu Glu Gly
 1               5                  10                  15

Gln Ala Ala Lys Glu Phe Ile Ala Phe Leu Val Lys Xaa Arg
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 51

His Xaa Glu Gly Thr Phe Thr Ser Asp Val Ser Ser Tyr Leu Glu Gly
 1               5                  10                  15

Gln Ala Ala Lys Glu Phe Ile Ala Phe Leu Val Lys Xaa Arg
            20                  25                  30

<210> SEQ ID NO 52
<211> LENGTH: 30
<212> TYPE: PRT
<213> ORGANISM: Artificial Sequence
```

-continued

```
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 25
<223> OTHER INFORMATION: Xaa = Nal (naphthylalanine)
<220> FEATURE:
<221> NAME/KEY: VARIANT
<222> LOCATION:
<223> OTHER INFORMATION: this sequence has an amidated c-terminus

<400> SEQUENCE: 52

His Xaa Glu Gly Thr Phe Thr Ser Asp Val Ser Ser Tyr Leu Glu Gly
 1               5                  10                  15

Gln Ala Ala Lys Glu Phe Ile Ala Xaa Leu Val Lys Xaa Arg
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 22, 25
<223> OTHER INFORMATION: Xaa = Nal (naphthylalanine)
<220> FEATURE:
<221> NAME/KEY: VARIANT
<222> LOCATION:
<223> OTHER INFORMATION: this sequence has an amidated c-terminus

<400> SEQUENCE: 53

His Xaa Glu Gly Thr Phe Thr Ser Asp Val Ser Ser Tyr Leu Glu Gly
 1               5                  10                  15

Gln Ala Ala Lys Glu Xaa Ile Ala Xaa Leu Val Lys Xaa Arg
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 25
<223> OTHER INFORMATION: Xaa = Nal (naphthylalanine)
<220> FEATURE:
<221> NAME/KEY: VARIANT
<222> LOCATION:
<223> OTHER INFORMATION: this sequence has an amidated c-terminus

<400> SEQUENCE: 54

His Xaa Glu Gly Thr Phe Thr Ser Asp Val Ser Ser Tyr Leu Glu Gly
 1               5                  10                  15

Gln Ala Ala Arg Glu Phe Ile Ala Xaa Leu Val Arg Xaa Arg
            20                  25                  30
```

```
<210> SEQ ID NO 55
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 55

His Xaa Glu Gly Thr Phe Thr Ser Asp Val Ser Ser Tyr Leu Glu Gly
 1               5                  10                  15

Gln Ala Ala Arg Glu Phe Ile Ala Phe Leu Val Arg Xaa Arg
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 13, 25
<223> OTHER INFORMATION: Xaa = Nal (naphthylalanine)
<220> FEATURE:
<221> NAME/KEY: VARIANT
<222> LOCATION:
<223> OTHER INFORMATION: this sequence has an amidated c-terminus

<400> SEQUENCE: 56

His Xaa Glu Gly Thr Phe Thr Ser Asp Val Ser Ser Xaa Leu Glu Gly
 1               5                  10                  15

Gln Ala Ala Lys Glu Phe Ile Ala Xaa Leu Val Lys Xaa Arg
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 6, 25
<223> OTHER INFORMATION: Xaa = Nal (naphthylalanine)
<220> FEATURE:
<221> NAME/KEY: VARIANT
<222> LOCATION:
<223> OTHER INFORMATION: this sequence has an amidated c-terminus

<400> SEQUENCE: 57

His Xaa Glu Gly Thr Xaa Thr Ser Asp Val Ser Ser Tyr Leu Glu Gly
 1               5                  10                  15

Gln Ala Ala Lys Glu Phe Ile Ala Xaa Leu Val Lys Xaa Arg
            20                  25                  30
```

<210> SEQ ID NO 58
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-decanoyl-lysine

<400> SEQUENCE: 58

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 59

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-dodecanoyl-lysine
<220> FEATURE:
<221> NAME/KEY: VARIANT
<222> LOCATION:
<223> OTHER INFORMATION: this sequence has an amidated c-terminus

<400> SEQUENCE: 60

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa

```
                    20                  25                  30

<210> SEQ ID NO 61
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 31
<223> OTHER INFORMATION: Xaa = O-decanoyl-serine
<220> FEATURE:
<221> NAME/KEY: VARIANT
<222> LOCATION:
<223> OTHER INFORMATION: this sequence has an amidated c-terminus

<400> SEQUENCE: 61

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Xaa Arg Xaa
             20                  25                  30

<210> SEQ ID NO 62
<211> LENGTH: 33
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 21
<223> OTHER INFORMATION: Xaa = Aib (alpha-aminoisobutyric acid)
<220> FEATURE:
<221> NAME/KEY: VARIANT
<222> LOCATION: 29, 31
<223> OTHER INFORMATION: Xaa = beta-Ala (beta-alanine)
<220> FEATURE:
<221> NAME/KEY: VARIANT
<222> LOCATION: 33
<223> OTHER INFORMATION: Xaa = N-epsilon-octanoyl-lysine

<400> SEQUENCE: 62

His Xaa Glu Gly Thr Phe Thr Ser Asp Val Ser Ser Tyr Leu Glu Gly
  1               5                  10                  15

Gln Ala Ala Lys Xaa Phe Ile Ala Trp Leu Val Lys Xaa Arg Xaa Arg
             20                  25                  30

Xaa

<210> SEQ ID NO 63
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
```

```
<220> FEATURE:
<221> NAME/KEY: VARIANT
<222> LOCATION: 31
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 63

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 31
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 64

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 31
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 65

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa
```

-continued

```
                    20                  25                  30

<210> SEQ ID NO 66
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = A5c (1-amino-1-cyclopentanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 66

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = Tma-His (N,N-tetramethylamidino-
      histidine)
<220> FEATURE:
<221> NAME/KEY: VARIANT
<222> LOCATION:
<223> OTHER INFORMATION: this sequence has an amidated c-terminus

<400> SEQUENCE: 67

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 68
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 31
<223> OTHER INFORMATION: Xaa = Aec (4-(2-aminoethyl)-1-carboxymethyl-
      piperazine)
<220> FEATURE:
<221> NAME/KEY: VARIANT
<222> LOCATION:
<223> OTHER INFORMATION: this sequence has an amidated c-terminus

<400> SEQUENCE: 68
```

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Xaa
            20                  25                  30
```

<210> SEQ ID NO 69
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 32
<223> OTHER INFORMATION: Xaa = Aec (4-(2-aminoethyl)-1-carboxymethyl-
     piperazine)
<220> FEATURE:
<221> NAME/KEY: VARIANT
<222> LOCATION:
<223> OTHER INFORMATION: this sequence has an amidated c-terminus

<400> SEQUENCE: 69

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Gly Xaa
            20                  25                  30
```

<210> SEQ ID NO 70
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 31, 32
<223> OTHER INFORMATION: Xaa = Aec (4-(2-aminoethyl)-1-carboxymethyl-
     piperazine)
<220> FEATURE:
<221> NAME/KEY: VARIANT
<222> LOCATION:
<223> OTHER INFORMATION: this sequence has an amidated c-terminus

<400> SEQUENCE: 70

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Xaa Xaa
            20                  25                  30
```

<210> SEQ ID NO 71
<211> LENGTH: 30
<212> TYPE: PRT
<213> ORGANISM: Artificial Sequence
<220> FEATURE:
<223> OTHER INFORMATION: Mutagen

```
<220> FEATURE:
<221> NAME/KEY: VARIANT
<222> LOCATION: 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 71

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 72

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N-alpha-Me-His (N-methyl histidine)
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 73

Xaa Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
```

```
<223> OTHER INFORMATION: Xaa = N-alpha-Me-His (N-methyl histidine)
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 74

Xaa Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N-alpha-Me-His (N-methyl histidine)
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 75

Xaa Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N-alpha-Me-His (N-alfa-methyl histidine)
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 76

Xaa Xaa Glu Gly Thr Phe Thr Ser Asp Val Ser Ser Tyr Leu Glu Gly
 1               5                  10                  15
```

```
Gln Ala Ala Arg Glu Phe Ile Ala Trp Leu Val Arg Xaa Arg
            20                  25                  30

<210> SEQ ID NO 77
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = A6c (1-amino-1-cycloxexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 77

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Xaa Arg
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = A5c (1-amino-1-cyclopentanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 78

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Xaa Arg
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = D-Ala
<220> FEATURE:
<221> NAME/KEY: VARIANT
<222> LOCATION:
```

<223> OTHER INFORMATION: this sequence has an amidated c-terminus

<400> SEQUENCE: 79

His Xaa Glu Gly Thr Phe Thr Ser Asp Val Ser Ser Tyr Leu Glu Gly
 1               5                   10                  15

Gln Ala Ala Lys Glu Phe Ile Ala Trp Leu Val Lys Xaa Arg
             20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A5c (1-amino-1-cyclopentanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 80

His Xaa Glu Gly Thr Phe Thr Ser Asp Val Ser Ser Tyr Leu Glu Gly
 1               5                   10                  15

Gln Ala Ala Lys Glu Phe Ile Ala Trp Xaa Val Lys Xaa Arg
             20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 81

His Xaa Glu Gly Thr Phe Thr Ser Asp Val Ser Ser Tyr Leu Glu Gly
 1               5                   10                  15

Gln Ala Ala Lys Glu Phe Ile Xaa Trp Leu Val Lys Xaa Arg
             20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 19, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus -continued

```
<400> SEQUENCE: 82

His Xaa Glu Gly Thr Phe Thr Ser Asp Val Ser Ser Tyr Leu Glu Gly
 1               5                  10                  15

Gln Ala Xaa Lys Glu Phe Ile Ala Trp Leu Val Lys Xaa Arg
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 10, 14
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 83

His Xaa Glu Gly Thr Phe Thr Ser Asp Xaa Ser Ser Tyr Xaa Glu Gly
 1               5                  10                  15

Gln Ala Ala Lys Glu Phe Ile Ala Trp Leu Val Lys Xaa Arg
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 10, 23, 26
<223> OTHER INFORMATION: Xaa = A6c (1-amino-1-cycloxexanecarboxylic
     acid)
<220> FEATURE:
<221> NAME/KEY: VARIANT
<222> LOCATION:
<223> OTHER INFORMATION: this sequence has an amidated c-terminus

<400> SEQUENCE: 84

His Xaa Glu Gly Thr Phe Thr Ser Asp Xaa Ser Ser Tyr Leu Glu Gly
 1               5                  10                  15

Gln Ala Ala Lys Glu Phe Xaa Ala Trp Xaa Val Lys Xaa Arg
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
```

```
<222> LOCATION: 14, 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 85

His Xaa Glu Gly Thr Phe Thr Ser Asp Val Ser Ser Tyr Xaa Glu Gly
 1               5                  10                  15

Gln Ala Ala Lys Glu Phe Ile Ala Trp Xaa Val Lys Xaa Arg
            20                  25                  30

<210> SEQ ID NO 86
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 14
<223> OTHER INFORMATION: Xaa = A6c (1-amino-1-cyclohexanecarboxylic
      acid
<220> FEATURE:
<221> NAME/KEY: VARIANT
<222> LOCATION:
<223> OTHER INFORMATION: this sequence has an amidated c-terminus

<400> SEQUENCE: 86

His Xaa Glu Gly Thr Phe Thr Ser Asp Val Ser Ser Tyr Xaa Glu Gly
 1               5                  10                  15

Gln Ala Ala Lys Glu Phe Ile Ala Trp Leu Val Lys Xaa Arg
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 87

His Xaa Glu Gly Thr Phe Thr Ser Asp Val Ser Ser Tyr Leu Glu Gly
 1               5                  10                  15

Gln Ala Lys Lys Glu Phe Ile Ala Trp Leu Val Lys Xaa Arg
            20                  25                  30

<210> SEQ ID NO 88
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
```

-continued

```
<223> OTHER INFORMATION: Xaa = Aib (alpha-aminoisobutyric acid)
<220> FEATURE:
<221> NAME/KEY: VARIANT
<222> LOCATION: 14
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 88

His Xaa Glu Gly Thr Phe Thr Ser Asp Val Ser Ser Tyr Xaa Glu Gly
 1               5                  10                  15

Gln Xaa Ala Lys Glu Phe Ile Ala Trp Leu Val Lys Xaa Arg
             20                  25                  30

<210> SEQ ID NO 89
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 23, 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 89

His Xaa Glu Gly Thr Phe Thr Ser Asp Val Ser Ser Tyr Leu Glu Gly
 1               5                  10                  15

Gln Ala Ala Lys Glu Phe Xaa Ala Trp Xaa Val Lys Xaa Arg
             20                  25                  30

<210> SEQ ID NO 90
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 23, 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 90

His Xaa Glu Gly Thr Phe Thr Ser Asp Val Ser Ser Tyr Leu Glu Gly
 1               5                  10                  15

Gln Xaa Ala Lys Glu Phe Xaa Ala Trp Xaa Val Lys Xaa Arg
             20                  25                  30

<210> SEQ ID NO 91
```

```
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 6
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 91

His Xaa Glu Gly Thr Xaa Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 92
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 14
<223> OTHER INFORMATION: Xaa = Cha (alpha-amino acid cyclohexylalanine)
<220> FEATURE:
<221> NAME/KEY: VARIANT
<222> LOCATION:
<223> OTHER INFORMATION: this sequence has an amidated c-terminus

<400> SEQUENCE: 92

His Xaa Glu Gly Thr Phe Thr Ser Asp Val Ser Ser Tyr Xaa Glu Gly
 1               5                  10                  15

Gln Ala Ala Lys Glu Phe Ile Ala Trp Leu Val Lys Xaa Arg
            20                  25                  30

<210> SEQ ID NO 93
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 27
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 93

His Xaa Glu Gly Thr Phe Thr Ser Asp Val Ser Ser Tyr Leu Glu Gly
```

```
                1               5                  10                  15
Gln Ala Ala Lys Glu Phe Ile Ala Trp Leu Xaa Lys Xaa Arg
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 10,14
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 94

His Xaa Glu Gly Thr Phe Thr Ser Asp Xaa Ser Ser Tyr Xaa Glu Gly
 1               5                  10                  15
Gln Ala Ala Lys Glu Phe Ile Ala Trp Leu Val Lys Xaa Arg
            20                  25                  30

<210> SEQ ID NO 95
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 16
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 95

His Xaa Glu Gly Thr Phe Thr Ser Asp Val Ser Ser Tyr Leu Glu Xaa
 1               5                  10                  15
Gln Ala Ala Lys Glu Phe Ile Ala Trp Leu Val Lys Xaa Arg
            20                  25                  30

<210> SEQ ID NO 96
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 16, 29
<223> OTHER INFORMATION: Xaa = Aib (alpha-aminoisobutyric acid)
<220> FEATURE:
<221> NAME/KEY: VARIANT
```

```
-continued

<222> LOCATION:
<223> OTHER INFORMATION: this sequence has an amidated c-terminus

<400> SEQUENCE: 96

His Xaa Glu Gly Thr Phe Thr Ser Asp Val Ser Ser Tyr Leu Glu Xaa
 1               5                  10                  15

Gln Ala Ala Lys Glu Phe Ile Ala Trp Leu Val Lys Xaa Arg
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 97

His Xaa Glu Gly Thr Phe Thr Ser Asp Val Ser Ser Tyr Leu Glu Gly
 1               5                  10                  15

Gln Xaa Ala Lys Glu Phe Glu Ala Trp Xaa Val Lys Xaa Arg
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 19, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 98

His Xaa Glu Gly Thr Phe Thr Ser Asp Val Ser Ser Tyr Leu Glu Gly
 1               5                  10                  15

Glu Xaa Xaa Lys Glu Phe Glu Ala Trp Xaa Val Lys Xaa Arg
            20                  25                  30

<210> SEQ ID NO 99
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 19, 29
```

```
<223> OTHER INFORMATION: Xaa = Aib (alpha-aminoisobutyric acid)
<220> FEATURE:
<221> NAME/KEY: VARIANT
<222> LOCATION: 10,14, 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 99

His Xaa Glu Gly Thr Phe Thr Ser Asp Xaa Ser Ser Tyr Xaa Glu Gly
 1               5                  10                  15

Glu Xaa Xaa Lys Glu Phe Ile Ala Trp Xaa Val Lys Xaa Arg
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 100

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Xaa Arg
            20                  25                  30

<210> SEQ ID NO 101
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A5c (1-amino-1-cyclopentanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 101
```

```
His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Xaa Arg
            20                  25                  30

<210> SEQ ID NO 102
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 102

His Xaa Glu Gly Thr Phe Thr Ser Asp Val Ser Ser Tyr Leu Glu Gly
 1               5                  10                  15

Gln Xaa Ala Lys Glu Phe Ile Ala Trp Leu Val Lys Xaa Arg
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 103

His Xaa Glu Gly Thr Phe Thr Ser Asp Val Ser Ser Tyr Leu Glu Gly
 1               5                  10                  15

Gln Ala Ala Lys Glu Phe Ile Xaa Trp Leu Val Lys Xaa Arg
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 19
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
```

```
<222> LOCATION:
<223> OTHER INFORMATION: this sequence has an amidated c-terminus

<400> SEQUENCE: 104

His Xaa Glu Gly Thr Phe Thr Ser Asp Val Ser Ser Tyr Leu Glu Gly
 1               5                  10                  15

Gln Ala Xaa Lys Glu Phe Ile Ala Trp Leu Val Lys Xaa Arg
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 10, 23, 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 105

His Xaa Glu Gly Thr Phe Thr Ser Asp Xaa Ser Ser Tyr Leu Glu Gly
 1               5                  10                  15

Gln Ala Ala Lys Glu Phe Xaa Ala Trp Xaa Val Lys Xaa Arg
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 14, 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 106

His Xaa Glu Gly Thr Phe Thr Ser Asp Val Ser Ser Tyr Xaa Glu Gly
 1               5                  10                  15

Gln Ala Ala Lys Glu Phe Ile Ala Trp Xaa Val Lys Xaa Arg
            20                  25                  30

<210> SEQ ID NO 107
```

```
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 14,
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 107

His Xaa Glu Gly Thr Phe Thr Ser Asp Val Ser Ser Tyr Xaa Glu Gly
 1               5                  10                  15

Gln Ala Ala Lys Glu Phe Ile Ala Trp Leu Val Lys Xaa Arg
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 108

His Xaa Glu Gly Thr Phe Thr Ser Asp Val Ser Ser Tyr Leu Glu Gly
 1               5                  10                  15

Gln Ala Lys Lys Glu Phe Ile Ala Trp Leu Val Lys Xaa Arg
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18
<223> OTHER INFORMATION: Xaa = Aib (alpha-aminoisobutyric acid)
<220> FEATURE:
<221> NAME/KEY: VARIANT
<222> LOCATION: 14
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
```

```
<220> FEATURE:
<221> NAME/KEY: VARIANT
<222> LOCATION:
<223> OTHER INFORMATION: this sequence has an amidated c-terminus

<400> SEQUENCE: 109

His Xaa Glu Gly Thr Phe Thr Ser Asp Val Ser Ser Tyr Xaa Glu Gly
 1               5                  10                  15

Gln Xaa Ala Lys Glu Phe Ile Ala Trp Leu Val Lys Xaa Arg
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 23, 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 110

His Xaa Glu Gly Thr Phe Thr Ser Asp Val Ser Ser Tyr Leu Glu Gly
 1               5                  10                  15

Gln Ala Ala Lys Glu Phe Xaa Ala Trp Xaa Val Lys Xaa Arg
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18
<223> OTHER INFORMATION: Xaa = Aib (alpha-aminoisobutyric acid)
<220> FEATURE:
<221> NAME/KEY: VARIANT
<222> LOCATION: 23, 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 111

His Xaa Glu Gly Thr Phe Thr Ser Asp Val Ser Ser Tyr Leu Glu Gly
 1               5                  10                  15

Gln Xaa Ala Lys Glu Phe Xaa Ala Trp Xaa Val Lys Xaa Arg
            20                  25                  30
```

```
<210> SEQ ID NO 112
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 6
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 112

His Xaa Glu Gly Thr Xaa Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 14
<223> OTHER INFORMATION: Xaa = Cha (alfa-amino acid-cyclohexylalanine)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 113

His Xaa Glu Gly Thr Phe Thr Ser Asp Val Ser Ser Tyr Xaa Glu Gly
 1               5                  10                  15

Gln Ala Ala Lys Glu Phe Ile Ala Trp Leu Val Lys Xaa Arg
            20                  25                  30

<210> SEQ ID NO 114
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 27
```

```
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 114

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Xaa Lys Xaa Arg
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 16, 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 115

His Xaa Glu Gly Thr Phe Thr Ser Asp Val Ser Ser Tyr Leu Glu Xaa
 1               5                  10                  15

Gln Ala Ala Lys Glu Phe Ile Ala Trp Leu Val Lys Xaa Arg
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 16
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 116

His Xaa Glu Gly Thr Phe Thr Ser Asp Val Ser Ser Tyr Leu Glu Xaa
 1               5                  10                  15

Gln Ala Ala Lys Glu Phe Ile Ala Trp Leu Val Lys Xaa Arg
            20                  25                  30

<210> SEQ ID NO 117
<211> LENGTH: 30
<212> TYPE: PRT
```

```
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 117

His Xaa Glu Gly Thr Phe Thr Ser Asp Val Ser Ser Tyr Leu Glu Gly
 1               5                  10                  15

Glu Ala Ala Lys Glu Phe Ile Ala Trp Xaa Val Lys Xaa Arg
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 118

His Xaa Glu Gly Thr Phe Thr Ser Asp Val Ser Ser Tyr Leu Glu Gly
 1               5                  10                  15

Glu Xaa Ala Lys Glu Phe Ile Ala Trp Xaa Val Lys Xaa Arg
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
```

```
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 119

His Xaa Glu Gly Thr Phe Thr Ser Asp Val Ser Ser Tyr Leu Glu Gly
 1               5                  10                  15

Glu Xaa Ala Lys Glu Phe Ile Ala Trp Xaa Val Xaa Xaa Arg
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 19
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 120

His Xaa Glu Gly Thr Phe Thr Ser Asp Val Ser Ser Tyr Leu Glu Gly
 1               5                  10                  15

Glu Xaa Xaa Lys Glu Phe Ile Ala Trp Xaa Val Lys Xaa Arg
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 19
<223> OTHER INFORMATION: Xaa = Aib (alpha-aminoisobutyric acid)
<220> FEATURE:
<221> NAME/KEY: VARIANT
<222> LOCATION: 10,14, 26
<223> OTHER INFORMATION: Xaa = A6c (1-amino-1-cyclohexanecarboxylic
      acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 121
```

-continued

```
His Xaa Glu Gly Thr Phe Thr Ser Asp Xaa Ser Ser Tyr Xaa Glu Gly
 1               5                  10                  15

Glu Xaa Xaa Lys Glu Phe Ile Ala Trp Xaa Val Lys Xaa Arg
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = D-Arg
<220> FEATURE:
<221> NAME/KEY: VARIANT
<222> LOCATION:
<223> OTHER INFORMATION: this sequence has an amidated c-terminus

<400> SEQUENCE: 122

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = D-Lys
<220> FEATURE:
<221> NAME/KEY: VARIANT
<222> LOCATION:
<223> OTHER INFORMATION: this sequence has an amidated c-terminus

<400> SEQUENCE: 123

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
```

```
<221> NAME/KEY: VARIANT
<222> LOCATION: 30
<223> OTHER INFORMATION: Xaa = D-Arg
<220> FEATURE:
<221> NAME/KEY: VARIANT
<222> LOCATION:
<223> OTHER INFORMATION: this sequence has an amidated c-terminus

<400> SEQUENCE: 124

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
            20                  25                  30

<210> SEQ ID NO 125
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = D-Lys
<220> FEATURE:
<221> NAME/KEY: VARIANT
<222> LOCATION:
<223> OTHER INFORMATION: this sequence has an amidated c-terminus

<400> SEQUENCE: 125

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 126

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg
            20                  25                  30

<210> SEQ ID NO 127
<211> LENGTH: 30
```

```
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 127

His Xaa Glu Gly Thr Phe Thr Ser Asp Val Ser Ser Tyr Leu Glu Gly
 1               5                   10                  15

Gln Ala Arg Arg Glu Phe Ile Ala Trp Leu Val Arg Xaa Arg
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 128

His Xaa Glu Gly Thr Phe Thr Ser Asp Val Ser Ser Tyr Leu Glu Gly
 1               5                   10                  15

Gln Ala Arg Arg Glu Phe Ile Ala Trp Leu Val Arg Xaa Arg
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 129

His Xaa Glu Gly Thr Phe Thr Ser Asp Val Ser Ser Tyr Leu Glu Gly
 1               5                   10                  15

Gln Ala Ala Arg Glu Phe Ile Ala Trp Leu Val Arg Xaa Xaa
            20                  25                  30
```

```
                     20                  25                  30

<210> SEQ ID NO 130
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 130

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Xaa Xaa Gly
             20                  25                  30

<210> SEQ ID NO 131
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 131

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Xaa Xaa Xaa
             20                  25                  30

<210> SEQ ID NO 132
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION: 31
<223> OTHER INFORMATION: Xaa = D-Ala
<220> FEATURE:
<221> NAME/KEY: VARIANT
```

```
<222> LOCATION:
<223> OTHER INFORMATION: this sequence has a hydroxylated c-terminus

<400> SEQUENCE: 132

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Xaa
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2,29,31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 133

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 31
<223> OTHER INFORMATION: Xaa = beta-Ala (beta-alanine)
<220> FEATURE:
<221> NAME/KEY: VARIANT
<222> LOCATION: 32
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 134

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Mutagen
<220> FEATURE:
```

```
<221> NAME/KEY: VARIANT
<222> LOCATION: 2,29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 135

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Xaa Arg Gly Xaa
             20                  25                  30

<210> SEQ ID NO 136
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION: 31
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has a hydroxylated c-terminus

<400> SEQUENCE: 136

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Gly Xaa Xaa
             20                  25                  30

<210> SEQ ID NO 137
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 31
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 137

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Gly Xaa Xaa
             20                  25                  30
```

```
<210> SEQ ID NO 138
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 31
<223> OTHER INFORMATION: Xaa = Ado (12-aminododecanoic acid)
<220> FEATURE:
<221> NAME/KEY: VARIANT
<222> LOCATION:
<223> OTHER INFORMATION: this sequence has a hydroxylated c-terminus

<400> SEQUENCE: 138

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 31
<223> OTHER INFORMATION: Xaa = Ado (12-aminododecanoic acid)
<220> FEATURE:
<221> NAME/KEY: VARIANT
<222> LOCATION:
<223> OTHER INFORMATION: this sequence has an amidated c-terminus

<400> SEQUENCE: 139

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa
            20                  25                  30

<210> SEQ ID NO 140
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION: 31
<223> OTHER INFORMATION: Xaa = D-Ala
<220> FEATURE:
<221> NAME/KEY: VARIANT
<222> LOCATION:
```

-continued

<223> OTHER INFORMATION: this sequence has a hydroxylated c-terminus

<400> SEQUENCE: 140

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Xaa Xaa
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 141

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Arg Xaa Xaa
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 31
<223> OTHER INFORMATION: Xaa = beta-Ala (beta-alanine)
<220> FEATURE:
<221> NAME/KEY: VARIANT
<222> LOCATION: 32
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has a hydroxylated c-terminus

<400> SEQUENCE: 142

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Arg Xaa Xaa
            20                  25                  30

<210> SEQ ID NO 143
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT -continued

```
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 143

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Xaa Arg
            20                  25                  30

<210> SEQ ID NO 144
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 144

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Xaa Arg
            20                  25                  30

<210> SEQ ID NO 145
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 145

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Xaa Arg
            20                  25                  30

<210> SEQ ID NO 146
<211> LENGTH: 30
<212> TYPE: PRT
```

```
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 146

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Xaa Arg
            20                  25                  30

<210> SEQ ID NO 147
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 147

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Xaa Arg
            20                  25                  30

<210> SEQ ID NO 148
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa =  N-epsilon-hexadecanoyl-lysine
<220> FEATURE:
<221> NAME/KEY: VARIANT
<222> LOCATION: 29
<223> OTHER INFORMATION: Xaa = beta-Ala (beta-alanine)
```

```
<220> FEATURE:
<221> NAME/KEY: VARIANT
<222> LOCATION:
<223> OTHER INFORMATION: this sequence has an amidated c-terminus

<400> SEQUENCE: 148

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Xaa Arg
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 149

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 150
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 150

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 151
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
```

```
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 151

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 152
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 152

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 153

His Xaa Glu Gly Thr Phe Thr Ser Asp Val Ser Ser Tyr Leu Glu Gly
 1               5                  10                  15

Gln Ala Lys Xaa Glu Phe Ile Ala Trp Leu Val Arg Xaa Arg
            20                  25                  30

<210> SEQ ID NO 154
<211> LENGTH: 30
<212> TYPE: PRT
<213> ORGANISM: Artificial Sequence
```

```
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 154

His Xaa Glu Gly Thr Phe Thr Ser Asp Val Ser Ser Tyr Leu Glu Gly
 1               5                  10                  15

Gln Ala Lys Xaa Glu Phe Ile Ala Trp Leu Val Arg Xaa Arg
            20                  25                  30

<210> SEQ ID NO 155
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 155

His Xaa Glu Gly Thr Phe Thr Ser Asp Val Ser Ser Tyr Leu Glu Gly
 1               5                  10                  15

Gln Ala Lys Xaa Glu Phe Ile Ala Trp Leu Val Arg Xaa Arg
            20                  25                  30

<210> SEQ ID NO 156
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 156

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
            20                  25                  30
```

```
<210> SEQ ID NO 157
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 157

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
            20                  25                  30

<210> SEQ ID NO 158
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2,29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysin
<220> FEATURE:
<221> NAME/KEY: VARIANT
<222> LOCATION:
<223> OTHER INFORMATION: this sequence has an amidated c-terminus

<400> SEQUENCE: 158

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 159

His Xaa Glu Gly Thr Phe Thr Ser Asp Val Ser Ser Tyr Leu Glu Gly
```

```
                1               5              10              15

Gln Ala Arg Xaa Glu Phe Ile Ala Trp Leu Val Arg Xaa Arg
            20                      25                  30

<210> SEQ ID NO 160
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 160

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                      25                  30

<210> SEQ ID NO 161
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 161

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                      25                  30

<210> SEQ ID NO 162
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
```

```
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 162

His Xaa Glu Gly Thr Phe Thr Ser Asp Val Ser Ser Tyr Leu Glu Gly
  1               5                  10                  15

Gln Ala Ala Xaa Glu Phe Ile Ala Trp Leu Val Arg Xaa Arg
             20                  25                  30

<210> SEQ ID NO 163
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-decanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 163

His Xaa Glu Gly Thr Phe Thr Ser Asp Val Ser Ser Tyr Leu Glu Gly
  1               5                  10                  15

Gln Ala Ala Xaa Glu Phe Ile Ala Trp Leu Val Arg Xaa Arg
             20                  25                  30

<210> SEQ ID NO 164
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 164

His Xaa Glu Gly Thr Phe Thr Ser Asp Val Ser Ser Tyr Leu Glu Gly
  1               5                  10                  15
```

Gln Ala Ala Lys Glu Phe Ile Ala Trp Leu Val Xaa Xaa Arg
           20                  25                  30

<210> SEQ ID NO 165
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 165

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Xaa Arg
           20                  25                  30

<210> SEQ ID NO 166
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 166

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Xaa Arg
           20                  25                  30

<210> SEQ ID NO 167
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

```
<400> SEQUENCE: 167

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 168
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 168

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 169

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 170
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
```

```
<220> FEATURE:
<221> NAME/KEY: VARIANT
<222> LOCATION:
<223> OTHER INFORMATION: this sequence has an amidated c-terminus

<400> SEQUENCE: 170

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 171
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 171

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 172
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 172

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 173
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
```

```
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 173

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 174

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Xaa Xaa Arg
            20                  25                  30

<210> SEQ ID NO 175
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 175

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Xaa Xaa Arg
            20                  25                  30

<210> SEQ ID NO 176
<211> LENGTH: 30
<212> TYPE: PRT
<213> ORGANISM: Artificial Sequence
```

```
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 176

His Xaa Glu Gly Thr Phe Thr Ser Asp Val Ser Ser Tyr Leu Glu Gly
  1               5                  10                  15

Gln Ala Lys Arg Glu Phe Ile Ala Trp Leu Val Xaa Xaa Arg
             20                  25                  30

<210> SEQ ID NO 177
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 177

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Xaa Xaa
             20                  25                  30

<210> SEQ ID NO 178
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 178

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Xaa Xaa
             20                  25                  30
```

<210> SEQ ID NO 179
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 179

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 180

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Xaa Xaa
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 181

His Xaa Glu Gly Thr Phe Thr Ser Asp Val Ser Ser Tyr Leu Glu Gly

```
                1               5              10              15

Gln Ala Ala Arg Glu Phe Ile Ala Trp Leu Val Lys Xaa Xaa
            20                  25                  30

<210> SEQ ID NO 182
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 182

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Xaa Xaa
            20                  25                  30

<210> SEQ ID NO 183
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 183

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 184
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: CONFLICT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
```

-continued

```
<223> OTHER INFORMATION: this sequence has an amidated c-terminus

<400> SEQUENCE: 184

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 185
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 185

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Gly Xaa
            20                  25                  30

<210> SEQ ID NO 186
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 186

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Gly Xaa
            20                  25                  30

<210> SEQ ID NO 187
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
```

<222> LOCATION: 32
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 187

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Gly Xaa
            20                  25                  30

<210> SEQ ID NO 188
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 188

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Gly Xaa
            20                  25                  30

<210> SEQ ID NO 189
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 189

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: Mutagen
<220> FEATURE:

```
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 190

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
             20                  25                  30

<210> SEQ ID NO 191
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 191

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
             20                  25                  30

<210> SEQ ID NO 192
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 192

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
             20                  25                  30

<210> SEQ ID NO 193
<211> LENGTH: 32
```

-continued

```
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 193

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
            20                  25                  30

<210> SEQ ID NO 194
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: CONFLICT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 194

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 195

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
```

```
                20              25              30

<210> SEQ ID NO 196
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 196

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Arg Xaa Xaa
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 197

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Arg Xaa Xaa
            20                  25                  30

<210> SEQ ID NO 198
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 198
```

-continued

```
His Xaa Glu Gly Thr Phe Thr Ser Asp Val Ser Ser Tyr Leu Glu Gly
 1               5                   10                  15

Gln Ala Lys Arg Glu Phe Ile Ala Trp Leu Val Arg Xaa Xaa
            20                  25                  30

<210> SEQ ID NO 199
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: Xaa = N-epsilon-octanoyl-lysine

<400> SEQUENCE: 199

His Xaa Glu Gly Thr Phe Thr Ser Asp Val Ser Ser Tyr Leu Glu Gly
 1               5                   10                  15

Gln Ala Arg Arg Glu Phe Ile Ala Trp Leu Val Arg Xaa Xaa
            20                  25                  30

<210> SEQ ID NO 200
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 200

His Xaa Glu Gly Thr Phe Thr Ser Asp Val Ser Ser Tyr Leu Glu Gly
 1               5                   10                  15

Gln Ala Arg Arg Glu Phe Ile Ala Trp Leu Val Arg Xaa Xaa
            20                  25                  30

<210> SEQ ID NO 201
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
```

```
<221> NAME/KEY: VARIANT
<222> LOCATION:
<223> OTHER INFORMATION: this sequence has an amidated c-terminus

<400> SEQUENCE: 201

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 202
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 202

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 203
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 203

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Xaa Arg
            20                  25                  30

<210> SEQ ID NO 204
<211> LENGTH: 30
<212> TYPE: PRT
<213> ORGANISM: Artificial Sequence
<220> FEATURE:
<223> OTHER INFORMATION: Mutagen
```

```
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 204

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Xaa Arg
            20                  25                  30

<210> SEQ ID NO 205
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 205

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Xaa Arg
            20                  25                  30

<210> SEQ ID NO 206
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
```

<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 206

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Xaa Xaa Arg
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 207

His Xaa Glu Gly Thr Phe Thr Ser Asp Val Ser Ser Tyr Leu Glu Gly
 1               5                  10                  15

Glu Ala Ala Lys Glu Phe Ile Ala Trp Leu Val Xaa Xaa Arg
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
    acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 208

His Xaa Glu Gly Thr Phe Thr Ser Asp Val Ser Ser Tyr Leu Glu Gly

```
                1               5                  10                  15
Glu Ala Ala Lys Glu Phe Ile Ala Trp Xaa Val Xaa Xaa Arg
            20                  25              30

<210> SEQ ID NO 209
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 209

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Xaa Xaa Arg
            20                  25              30

<210> SEQ ID NO 210
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 210

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Xaa Xaa Arg
            20                  25              30

<210> SEQ ID NO 211
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
```

```
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 211

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Xaa Xaa Arg
            20                  25              30

<210> SEQ ID NO 212
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-decanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 212

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Xaa Xaa Arg
            20                  25              30

<210> SEQ ID NO 213
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 213
```

```
His Xaa Glu Gly Thr Phe Thr Ser Asp Val Ser Ser Tyr Leu Glu Gly
1               5                   10                  15

Gln Ala Arg Arg Glu Phe Ile Ala Trp Xaa Val Xaa Xaa Arg
            20                  25              30

<210> SEQ ID NO 214
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 214

His Xaa Glu Gly Thr Phe Thr Ser Asp Val Ser Ser Tyr Leu Glu Gly
1               5                   10                  15

Gln Ala Arg Arg Glu Phe Ile Ala Trp Xaa Val Xaa Xaa Arg
            20                  25              30

<210> SEQ ID NO 215
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 215

His Xaa Glu Gly Thr Phe Thr Ser Asp Val Ser Ser Tyr Leu Glu Gly
1               5                   10                  15

Gln Ala Arg Arg Glu Phe Ile Ala Trp Xaa Val Xaa Xaa Arg
            20                  25              30

<210> SEQ ID NO 216
<211> LENGTH: 30
<212> TYPE: PRT
<213> ORGANISM: Artificial Sequence
<220> FEATURE:
<223> OTHER INFORMATION: Mutagen
<220> FEATURE:
```

```
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-decanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 216

His Xaa Glu Gly Thr Phe Thr Ser Asp Val Ser Ser Tyr Leu Glu Gly
 1               5                  10                  15

Gln Ala Arg Arg Glu Phe Ile Ala Trp Xaa Val Xaa Xaa Arg
            20                  25                  30

<210> SEQ ID NO 217
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 217

His Xaa Glu Gly Thr Phe Thr Ser Asp Val Ser Ser Tyr Leu Glu Gly
 1               5                  10                  15

Gln Ala Lys Arg Glu Phe Ile Ala Trp Xaa Val Xaa Xaa Arg
            20                  25                  30

<210> SEQ ID NO 218
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus
```

<400> SEQUENCE: 218

His Xaa Glu Gly Thr Phe Thr Ser Asp Val Ser Ser Tyr Leu Glu Gly
 1               5                  10                  15

Gln Ala Lys Arg Glu Phe Ile Ala Trp Xaa Val Xaa Xaa Arg
             20                  25                  30

<210> SEQ ID NO 219
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 219

His Xaa Glu Gly Thr Phe Thr Ser Asp Val Ser Ser Tyr Leu Glu Gly
 1               5                  10                  15

Gln Ala Lys Arg Glu Phe Ile Ala Trp Xaa Val Xaa Xaa Arg
             20                  25                  30

<210> SEQ ID NO 220
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 220

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
             20                  25                  30

<210> SEQ ID NO 221
<211> LENGTH: 30
<212> TYPE: PRT
<213> ORGANISM: Artificial Sequence
<220> FEATURE:

```
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 221

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
             20                  25                  30

<210> SEQ ID NO 222
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 222

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Xaa
             20                  25                  30

<210> SEQ ID NO 223
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = beta-Ala (beta-alanine)
<220> FEATURE:
<221> NAME/KEY: VARIANT
```

```
<222> LOCATION:
<223> OTHER INFORMATION: this sequence has an amidated c-terminus

<400> SEQUENCE: 223

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Xaa Xaa
             20                  25                  30

<210> SEQ ID NO 224
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 224

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Xaa Xaa
             20                  25                  30

<210> SEQ ID NO 225
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 225

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Xaa Xaa
             20                  25                  30

<210> SEQ ID NO 226
<211> LENGTH: 30
<212> TYPE: PRT
```

```
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 226

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 227
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 227

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 228
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-hexadecanoyl-lysine
```

```
<220> FEATURE:
<221> NAME/KEY: VARIANT
<222> LOCATION:
<223> OTHER INFORMATION: this sequence has an amidated c-terminus

<400> SEQUENCE: 228

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 229
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 229

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 230
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 230

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Arg Xaa Xaa
            20                  25                  30

<210> SEQ ID NO 231
```

```
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 231

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Arg Xaa Xaa
            20                  25                  30

<210> SEQ ID NO 232
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 232

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Arg Xaa Xaa
            20                  25                  30

<210> SEQ ID NO 233
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
```

```
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 233

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 234
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 234

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 235
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 235

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30
```

```
<210> SEQ ID NO 236
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 236

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
             20                  25                  30

<210> SEQ ID NO 237
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION: 26
<223> OTHER INFORMATION: Xaa = A6c (1-amino-1-cyclohexanecarboxylic
     acid)
<220> FEATURE:
<221> NAME/KEY: VARIANT
<222> LOCATION:
<223> OTHER INFORMATION: this sequence has an amidated c-terminus

<400> SEQUENCE: 237

His Xaa Glu Gly Thr Phe Thr Ser Asp Val Ser Ser Tyr Leu Glu Gly
 1               5                  10                  15

Gln Ala Ala Xaa Glu Phe Ile Ala Trp Xaa Val Arg Xaa Arg
             20                  25                  30

<210> SEQ ID NO 238
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
```

```
<223> OTHER INFORMATION: Xaa = N-epsilon-tetradecanoyl-lysine
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 238

His Xaa Glu Gly Thr Phe Thr Ser Asp Val Ser Ser Tyr Leu Glu Gly
 1               5                  10                  15

Gln Ala Ala Xaa Glu Phe Ile Ala Trp Xaa Val Arg Xaa Arg
            20                  25                  30

<210> SEQ ID NO 239
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysine
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION:
<223> OTHER INFORMATION: this sequence has an amidated c-terminus

<400> SEQUENCE: 239

His Xaa Glu Gly Thr Phe Thr Ser Asp Val Ser Ser Tyr Leu Glu Gly
 1               5                  10                  15

Gln Ala Ala Xaa Glu Phe Ile Ala Trp Xaa Val Arg Xaa Arg
            20                  25                  30

<210> SEQ ID NO 240
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 240
```

His Xaa Glu Gly Thr Phe Thr Ser Asp Val Ser Ser Tyr Leu Glu Gly
1               5                   10                  15

Gln Ala Ala Lys Glu Phe Ile Ala Trp Xaa Val Xaa Xaa Arg
            20                  25              30

<210> SEQ ID NO 241
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 241

His Xaa Glu Gly Thr Phe Thr Ser Asp Val Ser Ser Tyr Leu Glu Gly
1               5                   10                  15

Gln Ala Ala Lys Glu Phe Ile Ala Trp Xaa Val Xaa Xaa Arg
            20                  25              30

<210> SEQ ID NO 242
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 242

His Xaa Glu Gly Thr Phe Thr Ser Asp Val Ser Ser Tyr Leu Glu Gly
1               5                   10                  15

Gln Ala Ala Lys Glu Phe Ile Ala Trp Xaa Val Xaa Xaa Arg
            20                  25              30

<210> SEQ ID NO 243
<211> LENGTH: 30
<212> TYPE: PRT
<213> ORGANISM: Artificial Sequence
<220> FEATURE:
<223> OTHER INFORMATION: Mutagen

```
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 243

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Xaa Xaa Arg
             20                  25                  30

<210> SEQ ID NO 244
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 244

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Xaa Xaa Arg
             20                  25                  30

<210> SEQ ID NO 245
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-octanoyl-lysine
```

```
<220> FEATURE:
<221> NAME/KEY: VARIANT
<222> LOCATION:
<223> OTHER INFORMATION: this sequence has an amidated c-terminus

<400> SEQUENCE: 245

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Xaa Xaa
            20                  25                  30

<210> SEQ ID NO 246
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 246

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Xaa Xaa
            20                  25                  30

<210> SEQ ID NO 247
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 247

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Xaa Xaa
            20                  25                  30
```

```
<210> SEQ ID NO 248
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 248

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Lys Xaa Xaa
            20                  25                  30

<210> SEQ ID NO 249
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 249

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Lys Xaa Xaa
            20                  25                  30

<210> SEQ ID NO 250
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
```

```
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 250

His Xaa Glu Gly Thr Phe Thr Ser Asp Val Ser Ser Tyr Leu Glu Gly
  1               5                  10                  15

Gln Ala Ala Arg Glu Phe Ile Ala Trp Xaa Val Lys Xaa Xaa
             20                  25                  30

<210> SEQ ID NO 251
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 251

His Xaa Glu Gly Thr Phe Thr Ser Asp Val Ser Ser Tyr Leu Glu Gly
  1               5                  10                  15

Gln Ala Ala Arg Glu Phe Ile Ala Trp Xaa Val Arg Xaa Xaa
             20                  25                  30

<210> SEQ ID NO 252
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 252
```

```
His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Arg Xaa Xaa
                20                  25                  30
```

<210> SEQ ID NO 253
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 253

```
His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Arg Xaa Xaa
                20                  25                  30
```

<210> SEQ ID NO 254
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 254

```
His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Arg Xaa Xaa
                20                  25                  30
```

<210> SEQ ID NO 255
<211> LENGTH: 30
<212> TYPE: PRT
<213> ORGANISM: Artificial Sequence
<220> FEATURE:

```
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 255

His Xaa Glu Gly Thr Phe Thr Ser Asp Val Ser Ser Tyr Leu Glu Gly
  1               5                  10                  15

Gln Xaa Ala Xaa Glu Phe Ile Ala Trp Leu Val Arg Xaa Arg
             20                  25                  30

<210> SEQ ID NO 256
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 256

His Xaa Glu Gly Thr Phe Thr Ser Asp Val Ser Ser Tyr Leu Glu Gly
  1               5                  10                  15

Gln Xaa Ala Xaa Glu Phe Ile Ala Trp Leu Val Arg Xaa Arg
             20                  25                  30

<210> SEQ ID NO 257
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 257

His Xaa Glu Gly Thr Phe Thr Ser Asp Val Ser Ser Tyr Leu Glu Gly
  1               5                  10                  15

Gln Xaa Ala Xaa Glu Phe Ile Ala Trp Leu Val Arg Xaa Arg
             20                  25                  30
```

```
<210> SEQ ID NO 258
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 258

His Xaa Glu Gly Thr Phe Thr Ser Asp Val Ser Ser Tyr Leu Glu Gly
 1               5                  10                  15

Gln Xaa Ala Arg Glu Phe Ile Ala Trp Leu Val Xaa Xaa Arg
            20                  25                  30

<210> SEQ ID NO 259
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 259

His Xaa Glu Gly Thr Phe Thr Ser Asp Val Ser Ser Tyr Leu Glu Gly
 1               5                  10                  15

Gln Xaa Ala Arg Glu Phe Ile Ala Trp Leu Val Xaa Xaa Arg
            20                  25                  30

<210> SEQ ID NO 260
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 260

His Xaa Glu Gly Thr Phe Thr Ser Asp Val Ser Ser Tyr Leu Glu Gly
 1               5                  10                  15
```

```
Gln Xaa Ala Arg Glu Phe Ile Ala Trp Leu Val Xaa Xaa Arg
        20                  25                  30
```

<210> SEQ ID NO 261
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 261

```
His Xaa Glu Gly Thr Phe Thr Ser Asp Val Ser Ser Tyr Leu Glu Gly
  1               5                  10                  15

Gln Xaa Ala Arg Glu Phe Ile Ala Trp Leu Val Arg Xaa Xaa
        20                  25                  30
```

<210> SEQ ID NO 262
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 262

```
His Xaa Glu Gly Thr Phe Thr Ser Asp Val Ser Ser Tyr Leu Glu Gly
  1               5                  10                  15

Gln Xaa Ala Arg Glu Phe Ile Ala Trp Leu Val Arg Xaa Xaa
        20                  25                  30
```

<210> SEQ ID NO 263
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

```
<400> SEQUENCE: 263

His Xaa Glu Gly Thr Phe Thr Ser Asp Val Ser Ser Tyr Leu Glu Gly
 1               5                  10                  15

Gln Xaa Ala Arg Glu Phe Ile Ala Trp Leu Val Arg Xaa Xaa
            20                  25                  30

<210> SEQ ID NO 264
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 264

His Xaa Glu Gly Thr Phe Thr Ser Asp Val Ser Ser Tyr Leu Glu Gly
 1               5                  10                  15

Glu Xaa Ala Lys Glu Phe Ile Ala Trp Xaa Val Xaa Xaa Arg
            20                  25                  30

<210> SEQ ID NO 265
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 265

His Xaa Glu Gly Thr Phe Thr Ser Asp Val Ser Ser Tyr Leu Glu Gly
 1               5                  10                  15

Glu Ala Ala Xaa Glu Phe Ile Ala Trp Leu Val Arg Xaa Arg
            20                  25                  30

<210> SEQ ID NO 266
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
```

<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 266

His Xaa Glu Gly Thr Phe Thr Ser Asp Val Ser Ser Tyr Leu Glu Gly
 1               5                  10                  15

Glu Ala Ala Xaa Glu Phe Ile Ala Trp Leu Val Arg Xaa Arg
            20                  25                  30

<210> SEQ ID NO 267
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 267

His Xaa Glu Gly Thr Phe Thr Ser Asp Val Ser Ser Tyr Leu Glu Gly
 1               5                  10                  15

Glu Ala Ala Xaa Glu Phe Ile Ala Trp Leu Val Arg Xaa Arg
            20                  25                  30

<210> SEQ ID NO 268
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 268

His Xaa Glu Gly Thr Phe Thr Ser Asp Val Ser Ser Tyr Leu Glu Gly
 1               5                  10                  15

Glu Ala Ala Lys Glu Phe Ile Ala Trp Leu Val Xaa Xaa Arg
            20                  25                  30

<210> SEQ ID NO 269
<211> LENGTH: 30
<212> TYPE: PRT

```
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 269

His Xaa Glu Gly Thr Phe Thr Ser Asp Val Ser Ser Tyr Leu Glu Gly
 1               5                  10                  15

Glu Ala Ala Lys Glu Phe Ile Ala Trp Xaa Val Xaa Xaa Arg
            20                  25                  30

<210> SEQ ID NO 270
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 270

His Xaa Glu Gly Thr Phe Thr Ser Asp Val Ser Ser Tyr Leu Glu Gly
 1               5                  10                  15

Glu Ala Ala Arg Glu Phe Ile Ala Trp Leu Val Xaa Xaa Arg
            20                  25                  30

<210> SEQ ID NO 271
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 271
```

His Xaa Glu Gly Thr Phe Thr Ser Asp Val Ser Ser Tyr Leu Glu Gly
1               5                   10                  15

Glu Ala Ala Arg Glu Phe Ile Ala Trp Leu Val Xaa Xaa Arg
            20                  25              30

<210> SEQ ID NO 272
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 272

His Xaa Glu Gly Thr Phe Thr Ser Asp Val Ser Ser Tyr Leu Glu Gly
1               5                   10                  15

Glu Ala Ala Arg Glu Phe Ile Ala Trp Leu Val Xaa Xaa Arg
            20                  25              30

<210> SEQ ID NO 273
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 273

His Xaa Glu Gly Thr Phe Thr Ser Asp Val Ser Ser Tyr Leu Glu Gly
1               5                   10                  15

Glu Ala Ala Lys Glu Phe Ile Ala Trp Leu Val Lys Xaa Xaa
            20                  25              30

<210> SEQ ID NO 274
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT

```
<222> LOCATION:
<223> OTHER INFORMATION: this sequence has an amidated c-terminus

<400> SEQUENCE: 274

His Xaa Glu Gly Thr Phe Thr Ser Asp Val Ser Ser Tyr Leu Glu Gly
 1               5                  10                  15

Glu Ala Ala Lys Glu Phe Ile Ala Trp Leu Val Lys Xaa Xaa
            20                  25                  30

<210> SEQ ID NO 275
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 275

His Xaa Glu Gly Thr Phe Thr Ser Asp Val Ser Ser Tyr Leu Glu Gly
 1               5                  10                  15

Glu Ala Ala Lys Glu Phe Ile Ala Trp Leu Val Lys Xaa Xaa
            20                  25                  30

<210> SEQ ID NO 276
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 276

His Xaa Glu Gly Thr Phe Thr Ser Asp Val Ser Ser Tyr Leu Glu Gly
 1               5                  10                  15

Glu Ala Ala Arg Glu Phe Ile Ala Trp Leu Val Arg Xaa Xaa
            20                  25                  30

<210> SEQ ID NO 277
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
```

```
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 277

His Xaa Glu Gly Thr Phe Thr Ser Asp Val Ser Ser Tyr Leu Glu Gly
 1               5                  10                  15

Glu Ala Ala Arg Glu Phe Ile Ala Trp Leu Val Arg Xaa Xaa
            20                  25                  30

<210> SEQ ID NO 278
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 278

His Xaa Glu Gly Thr Phe Thr Ser Asp Val Ser Ser Tyr Leu Glu Gly
 1               5                  10                  15

Glu Ala Ala Arg Glu Phe Ile Ala Trp Leu Val Arg Xaa Xaa
            20                  25                  30

<210> SEQ ID NO 279
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 279

His Xaa Glu Gly Thr Phe Thr Ser Asp Val Ser Ser Tyr Leu Glu Gly
 1               5                  10                  15

Gln Ala Ala Xaa Glu Phe Ile Xaa Trp Leu Val Arg Xaa Arg
            20                  25                  30

<210> SEQ ID NO 280
<211> LENGTH: 30
<212> TYPE: PRT
<213> ORGANISM: Artificial Sequence
<220> FEATURE:
<223> OTHER INFORMATION: Mutagen
```

```
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 280

His Xaa Glu Gly Thr Phe Thr Ser Asp Val Ser Ser Tyr Leu Glu Gly
 1               5                  10                  15

Gln Ala Ala Xaa Glu Phe Ile Xaa Trp Leu Val Arg Xaa Arg
            20                  25                  30

<210> SEQ ID NO 281
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 281

His Xaa Glu Gly Thr Phe Thr Ser Asp Val Ser Ser Tyr Leu Glu Gly
 1               5                  10                  15

Gln Ala Ala Xaa Glu Phe Ile Xaa Trp Leu Val Arg Xaa Arg
            20                  25                  30

<210> SEQ ID NO 282
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 282

His Xaa Glu Gly Thr Phe Thr Ser Asp Val Ser Ser Tyr Leu Glu Gly
 1               5                  10                  15

Gln Ala Ala Arg Glu Phe Ile Xaa Trp Leu Val Xaa Xaa Arg
            20                  25                  30

<210> SEQ ID NO 283
```

```
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 283

His Xaa Glu Gly Thr Phe Thr Ser Asp Val Ser Ser Tyr Leu Glu Gly
 1               5                  10                  15
Gln Ala Ala Arg Glu Phe Ile Xaa Trp Leu Val Xaa Xaa Arg
            20                  25                  30

<210> SEQ ID NO 284
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 284

His Xaa Glu Gly Thr Phe Thr Ser Asp Val Ser Ser Tyr Leu Glu Gly
 1               5                  10                  15
Gln Ala Ala Arg Glu Phe Ile Xaa Trp Leu Val Xaa Xaa Arg
            20                  25                  30

<210> SEQ ID NO 285
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 285

His Xaa Glu Gly Thr Phe Thr Ser Asp Val Ser Ser Tyr Leu Glu Gly
 1               5                  10                  15
```

Gln Ala Ala Arg Glu Phe Ile Xaa Trp Leu Val Arg Xaa Xaa
            20                  25                  30

<210> SEQ ID NO 286
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 286

His Xaa Glu Gly Thr Phe Thr Ser Asp Val Ser Ser Tyr Leu Glu Gly
 1               5                   10                  15

Gln Ala Ala Arg Glu Phe Ile Xaa Trp Leu Val Arg Xaa Xaa
            20                  25                  30

<210> SEQ ID NO 287
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 24, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 287

His Xaa Glu Gly Thr Phe Thr Ser Asp Val Ser Ser Tyr Leu Glu Gly
 1               5                   10                  15

Gln Ala Ala Arg Glu Phe Ile Xaa Trp Leu Val Arg Xaa Xaa
            20                  25                  30

<210> SEQ ID NO 288
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-octanoyl-lysine

```
<220> FEATURE:
<221> NAME/KEY: VARIANT
<222> LOCATION:
<223> OTHER INFORMATION: this sequence has an amidated c-terminus

<400> SEQUENCE: 288

His Xaa Glu Gly Thr Phe Thr Ser Asp Val Ser Ser Tyr Leu Glu Gly
 1               5                  10                  15

Glu Ala Ala Lys Glu Phe Ile Ala Trp Xaa Val Lys Xaa Xaa
            20                  25                  30

<210> SEQ ID NO 289
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 289

His Xaa Glu Gly Thr Phe Thr Ser Asp Val Ser Ser Tyr Leu Glu Gly
 1               5                  10                  15

Glu Ala Ala Lys Glu Phe Ile Ala Trp Xaa Val Lys Xaa Xaa
            20                  25                  30

<210> SEQ ID NO 290
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 290

His Xaa Glu Gly Thr Phe Thr Ser Asp Val Ser Ser Tyr Leu Glu Gly
 1               5                  10                  15

Glu Ala Ala Lys Glu Phe Ile Ala Trp Xaa Val Lys Xaa Xaa
            20                  25                  30
```

```
<210> SEQ ID NO 291
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 291

His Xaa Glu Gly Thr Phe Thr Ser Asp Val Ser Ser Tyr Leu Glu Gly
 1               5                  10                  15

Glu Ala Ala Arg Glu Phe Ile Ala Trp Xaa Val Arg Xaa Xaa
            20                  25                  30

<210> SEQ ID NO 292
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 292

His Xaa Glu Gly Thr Phe Thr Ser Asp Val Ser Ser Tyr Leu Glu Gly
 1               5                  10                  15

Glu Ala Ala Arg Glu Phe Ile Ala Trp Xaa Val Arg Xaa Xaa
            20                  25                  30

<210> SEQ ID NO 293
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
```

```
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 293

His Xaa Glu Gly Thr Phe Thr Ser Asp Val Ser Ser Tyr Leu Glu Gly
 1               5                  10                  15

Glu Ala Ala Arg Glu Phe Ile Ala Trp Xaa Val Arg Xaa Xaa
            20                  25                  30

<210> SEQ ID NO 294
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 294

His Xaa Glu Gly Thr Phe Thr Ser Asp Val Ser Ser Tyr Leu Glu Gly
 1               5                  10                  15

Glu Xaa Ala Arg Glu Phe Ile Ala Trp Xaa Val Arg Xaa Xaa
            20                  25                  30

<210> SEQ ID NO 295
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 295
```

-continued

```
His Xaa Glu Gly Thr Phe Thr Ser Asp Val Ser Ser Tyr Leu Glu Gly
 1               5                  10                  15

Glu Xaa Ala Arg Glu Phe Ile Ala Trp Xaa Val Arg Xaa Xaa
            20                  25                  30

<210> SEQ ID NO 296
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 296

His Xaa Glu Gly Thr Phe Thr Ser Asp Val Ser Ser Tyr Leu Glu Gly
 1               5                  10                  15

Glu Xaa Ala Arg Glu Phe Ile Ala Trp Xaa Val Arg Xaa Xaa
            20                  25                  30

<210> SEQ ID NO 297
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 24, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-octanoyl-lysine
<220> FEATURE:
<221> NAME/KEY: VARIANT
<222> LOCATION:
<223> OTHER INFORMATION: this sequence has an amidated c-terminus

<400> SEQUENCE: 297

His Xaa Glu Gly Thr Phe Thr Ser Asp Val Ser Ser Tyr Leu Glu Gly
 1               5                  10                  15

Glu Xaa Ala Arg Glu Phe Ile Xaa Trp Xaa Val Arg Xaa Xaa
            20                  25                  30

<210> SEQ ID NO 298
<211> LENGTH: 30
<212> TYPE: PRT
<213> ORGANISM: Artificial Sequence
<220> FEATURE:
```

```
<223> OTHER INFORMATION: Mutagen
<220> FEATURE:
<221> NAME/KEY: VARIANT
<222> LOCATION: 2, 18, 24, 29
<223> OTHER INFORMATION: Xaa = Aib (alpha-aminoisobutyric acid)
<220> FEATURE:
<221> NAME/KEY: VARIANT
<222> LOCATION: 26
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-tetradecanoyl-lysine
<220> FEATURE:
<221> NAME/KEY: VARIANT
<222> LOCATION:
<223> OTHER INFORMATION: this sequence has an amidated c-terminus

<400> SEQUENCE: 298

His Xaa Glu Gly Thr Phe Thr Ser Asp Val Ser Ser Tyr Leu Glu Gly
 1               5                  10                  15
Glu Xaa Ala Arg Glu Phe Ile Xaa Trp Xaa Val Arg Xaa Xaa
            20                  25                  30

<210> SEQ ID NO 299
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 18, 24, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = A6c (1-amino-1-cyclohexanecarboxylic
      acid)
<220> FEATURE:
<221> NAME/KEY: VARIANT
<222> LOCATION: 30
<223> OTHER INFORMATION: Xaa = N-epsilon-hexadecanoyl-lysine
<220> FEATURE:
<221> NAME/KEY: VARIANT
<222> LOCATION:
<223> OTHER INFORMATION: this sequence has an amidated c-terminus

<400> SEQUENCE: 299

His Xaa Glu Gly Thr Phe Thr Ser Asp Val Ser Ser Tyr Leu Glu Gly
 1               5                  10                  15
Glu Xaa Ala Arg Glu Phe Ile Xaa Trp Xaa Val Arg Xaa Xaa
            20                  25                  30

<210> SEQ ID NO 300
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-HEPES-His(N-alpha-(4-(2-
      hydroxyethyl)-1-piperazine-ethanesulfonic acid)-histidine
<220> FEATURE:
<221> NAME/KEY: VARIANT
<222> LOCATION: 29
<223> OTHER INFORMATION: Xaa = Aib (alpha-aminoisobutyric acid)
<220> FEATURE:
<221> NAME/KEY: VARIANT
<222> LOCATION:
```

<223> OTHER INFORMATION: this sequence has an amidated c-terminus

<400> SEQUENCE: 300

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 301
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-HEPES-His(N-alpha-(4-(2-
      hydroxyethyl)-1-piperazine-ethanesulfonic acid)-histidine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 301

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 302
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-HEPES-His(N-alpha-(4-(2-
      hydroxyethyl)-1-piperazine-ethanesulfonic acid)-histidine
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 302

Xaa Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 303
<211> LENGTH: 30
<212> TYPE: PRT
<213> ORGANISM: Artificial Sequence
<220> FEATURE:
<223> OTHER INFORMATION: Mutagen

```
<220> FEATURE:
<221> NAME/KEY: VARIANT
<222> LOCATION: 1
<223> OTHER INFORMATION: Xaa = N alfa-HEPA-His(N-alpha-(4-(2-
      hydroxyethyl)-1-piperazineacetyl)-histidine
<220> FEATURE:
<221> NAME/KEY: VARIANT
<222> LOCATION: 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 303

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 304
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-HEPA-His(N-alpha-(4-(2-
      hydroxyethyl)-1-piperazineacetyl)-histidine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 304

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 305
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-HEPA-His(N-alpha-(4-(2-
      hydroxyethyl)-1-piperazineacetyl)-histidine
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 305

Xaa Xaa Glu Gly Thr Phe Thr Ser Asp Val Ser Ser Tyr Leu Glu Gly
```

-continued

```
                1               5                  10                 15
Gln Ala Ala Lys Glu Phe Ile Ala Trp Leu Val Lys Xaa Arg
            20                  25                 30

<210> SEQ ID NO 306
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 306

Xaa Ala Glu Gly Thr Phe Thr Ser Asp Val Ser Ser Tyr Leu Glu Gly
 1               5                  10                 15
Gln Ala Ala Lys Glu Phe Ile Ala Trp Leu Val Lys Xaa Arg
            20                  25                 30

<210> SEQ ID NO 307
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl- histadine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 307

Xaa Ala Glu Gly Thr Phe Thr Ser Asp Val Ser Ser Tyr Leu Glu Gly
 1               5                  10                 15
Gln Ala Ala Lys Glu Phe Ile Ala Trp Leu Val Lys Xaa Arg
            20                  25                 30

<210> SEQ ID NO 308
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
```

```
<223> OTHER INFORMATION: this sequence has an amidated c-terminus

<400> SEQUENCE: 308

Xaa Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 309
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 309

Xaa Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg
            20                  25                  30

<210> SEQ ID NO 310
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 310

Xaa Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg
            20                  25                  30

<210> SEQ ID NO 311
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
```

-continued

```
<222> LOCATION: 1
<223> OTHER INFORMATION: Xaa = N alfa-tetradecanoyl-histadine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 311

Xaa Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg
            20                  25                  30

<210> SEQ ID NO 312
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 312

Xaa Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg
            20                  25                  30

<210> SEQ ID NO 313
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 313

Xaa Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg
            20                  25                  30
```

```
<210> SEQ ID NO 314
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus

<400> SEQUENCE: 314

Xaa Ala Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION:
<223> OTHER INFORMATION: this sequence has an amidated c-terminus

<400> SEQUENCE: 315

Xaa Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg
            20                  25                  30

<210> SEQ ID NO 316
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = N alfa-tetradecanoyl-histadine
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION:
<223> OTHER INFORMATION: this sequence has an amidated c-terminus
```

<400> SEQUENCE: 316

Xaa Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg
             20                  25                  30

<210> SEQ ID NO 317
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-octanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 317

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
             20                  25                  30

<210> SEQ ID NO 318
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-dodecanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 318

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
             20                  25                  30

<210> SEQ ID NO 319
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20

```
<223> OTHER INFORMATION: Xaa = N-epsilon-hexadecanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 319

His Xaa Glu Gly Thr Phe Thr Ser Asp Val Ser Ser Tyr Leu Glu Gly
  1               5                  10                  15

Gln Ala Ala Xaa Glu Phe Ile Ala Trp Leu Val Arg Xaa Arg
             20                  25                  30

<210> SEQ ID NO 320
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-octanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 320

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Xaa Xaa Arg
             20                  25                  30

<210> SEQ ID NO 321
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-dodecanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 321

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Xaa Xaa Arg
             20                  25                  30

<210> SEQ ID NO 322
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
```

```
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-hexadecanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 322

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 323
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-octanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 323

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 324
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-hexadecanesulfonyl-lysine
<220> FEATURE:
<221> NAME/KEY: VARIANT
<222> LOCATION:
<223> OTHER INFORMATION: this sequence has an amidated c-terminus

<400> SEQUENCE: 324

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 325
<211> LENGTH: 30
<212> TYPE: PRT
```

```
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = 1-(4-decyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 325

His Xaa Glu Gly Thr Phe Thr Ser Asp Val Ser Ser Tyr Leu Glu Gly
  1               5                  10                  15

Gln Ala Ala Xaa Glu Phe Ile Ala Trp Leu Val Arg Xaa Arg
             20                  25                  30

<210> SEQ ID NO 326
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 326

His Xaa Glu Gly Thr Phe Thr Ser Asp Val Ser Ser Tyr Leu Glu Gly
  1               5                  10                  15

Gln Ala Ala Xaa Glu Phe Ile Ala Trp Leu Val Arg Xaa Arg
             20                  25                  30

<210> SEQ ID NO 327
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = 1-(4-tetradecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 327

His Xaa Glu Gly Thr Phe Thr Ser Asp Val Ser Ser Tyr Leu Glu Gly
  1               5                  10                  15

Gln Ala Ala Xaa Glu Phe Ile Ala Trp Leu Val Arg Xaa Arg
             20                  25                  30
```

```
<210> SEQ ID NO 328
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 328

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 329
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = 1-(4-decyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 329

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 330
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 330
```

```
His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Xaa Xaa Arg
             20                  25              30

<210> SEQ ID NO 331
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = 1-(4-tetradecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 331

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Xaa Xaa Arg
             20                  25              30

<210> SEQ ID NO 332
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 332

His Xaa Glu Gly Thr Phe Thr Ser Asp Val Ser Ser Tyr Leu Glu Gly
  1               5                  10                  15

Gln Ala Ala Arg Glu Phe Ile Ala Trp Leu Val Xaa Xaa Arg
             20                  25              30

<210> SEQ ID NO 333
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = 1-(4-decyl-piperazine)-asparagines
<220> FEATURE:
<221> NAME/KEY: VARIANT
```

```
<222> LOCATION:
<223> OTHER INFORMATION: this sequence has an amidated c-terminus

<400> SEQUENCE: 333

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 334
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 334

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 335
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 335

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 336
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
```

```
<221> NAME/KEY: VARIANT
<222> LOCATION: 32
<223> OTHER INFORMATION: Xaa = 1-(4-decyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 336

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Gly Xaa
            20                  25                  30

<210> SEQ ID NO 337
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 337

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Gly Xaa
            20                  25                  30

<210> SEQ ID NO 338
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-tetradecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 338

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Gly Xaa
            20                  25                  30

<210> SEQ ID NO 339
<211> LENGTH: 32
<212> TYPE: PRT
<213> ORGANISM: Artificial Sequence
<220> FEATURE:
<223> OTHER INFORMATION: Mutagen
```

-continued

```
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 339

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Gly Xaa
            20                  25                  30

<210> SEQ ID NO 340
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-decyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 340

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Xaa Xaa
            20                  25                  30

<210> SEQ ID NO 341
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 341

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Xaa Xaa
            20                  25                  30

<210> SEQ ID NO 342
```

```
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-tetradecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 342

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Xaa Xaa
            20                  25                  30

<210> SEQ ID NO 343
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 343

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa Xaa Xaa
            20                  25                  30

<210> SEQ ID NO 344
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2,29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = 1-(4-decyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 344

His Xaa Glu Gly Thr Phe Thr Ser Asp Val Ser Ser Tyr Leu Glu Gly
 1               5                  10                  15
```

```
Gln Ala Arg Xaa Glu Phe Ile Ala Trp Leu Val Arg Xaa Arg
            20              25              30

<210> SEQ ID NO 345
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 345

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
            20              25              30

<210> SEQ ID NO 346
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = 1-(4-tetradecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 346

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
            20              25              30

<210> SEQ ID NO 347
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: Xaa = Aib (alpha-aminoisobutyric acid)
```

```
<400> SEQUENCE: 347

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
            20                  25                  30

<210> SEQ ID NO 348
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = 1-(4-decyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 348

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 349
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 349

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 350
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = 1-(4-tetradecyl-piperazine)-asparagines
```

```
<220> FEATURE:
<221> NAME/KEY: VARIANT
<222> LOCATION:
<223> OTHER INFORMATION: this sequence has an amidated c-terminus

<400> SEQUENCE: 350

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 351
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 351

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 352
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = 1-(4-decyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 352

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 353
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
```

```
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 353

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 354
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = 1-(4-tetradecyl-piperazine)-
      acetyl)asparagines
<220> FEATURE:
<221> NAME/KEY: VARIANT
<222> LOCATION:
<223> OTHER INFORMATION: this sequence has an amidated c-terminus

<400> SEQUENCE: 354

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 355
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 355

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 356
<211> LENGTH: 32
<212> TYPE: PRT
```

```
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-decyl-piperazine)-asparagines
<220> FEATURE:
<221> NAME/KEY: CONFLICT
<222> LOCATION:
<223> OTHER INFORMATION: this sequence has an amidated c-terminus

<400> SEQUENCE: 356

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Gly Xaa
            20                  25                  30

<210> SEQ ID NO 357
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: Xaa = Aib (alpha-aminoisobutyric acid)

<400> SEQUENCE: 357

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Gly Xaa
            20                  25                  30

<210> SEQ ID NO 358
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-tetradecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 358

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Gly Xaa
            20                  25                  30
```

<210> SEQ ID NO 359
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 359

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Gly Xaa
            20                  25                  30

<210> SEQ ID NO 360
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-decyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 360

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
            20                  25                  30

<210> SEQ ID NO 361
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-dodecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 361

His Xaa Glu Gly Thr Phe Thr Ser Asp Val Ser Ser Tyr Leu Glu Gly
1               5                   10                  15

Gln Ala Arg Arg Glu Phe Ile Ala Trp Leu Val Arg Xaa Arg Xaa Xaa
            20                  25                  30

<210> SEQ ID NO 362
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-tetradecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 362

His Xaa Glu Gly Thr Phe Thr Ser Asp Val Ser Ser Tyr Leu Glu Gly
1               5                   10                  15

Gln Ala Arg Arg Glu Phe Ile Ala Trp Leu Val Arg Xaa Arg Xaa Xaa
            20                  25                  30

<210> SEQ ID NO 363
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = 1-(4-hexadecyl-piperazine)-asparagines
<220> FEATURE:
<221> NAME/KEY: VARIANT
<222> LOCATION:
<223> OTHER INFORMATION: this sequence has an amidated c-terminus

<400> SEQUENCE: 363

His Xaa Glu Gly Thr Phe Thr Ser Asp Val Ser Ser Tyr Leu Glu Gly
1               5                   10                  15

Gln Ala Arg Arg Glu Phe Ile Ala Trp Leu Val Arg Xaa Arg Xaa Xaa
            20                  25                  30

<210> SEQ ID NO 364
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa =  1-dodecylamino-glutamine
<220> FEATURE:
<221> NAME/KEY: VARIANT -continued

```
<222> LOCATION:
<223> OTHER INFORMATION: this sequence has an amidated c-terminus

<400> SEQUENCE: 364

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 365
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa =  1-dodecylamino-glutamine
<220> FEATURE:
<221> NAME/KEY: VARIANT
<222> LOCATION:
<223> OTHER INFORMATION: this sequence has an amidated c-terminus

<400> SEQUENCE: 365

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 366
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa =  1-dodecylamino-glutamine
<220> FEATURE:
<221> NAME/KEY: VARIANT
<222> LOCATION:
<223> OTHER INFORMATION: this sequence has an amidated c-terminus

<400> SEQUENCE: 366

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 367
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
```

```
<221> NAME/KEY: VARIANT
<222> LOCATION: 32
<223> OTHER INFORMATION: Xaa =  1-dodecylamino-glutamine
<220> FEATURE:
<221> NAME/KEY: VARIANT
<222> LOCATION:
<223> OTHER INFORMATION: this sequence has an amidated c-terminus

<400> SEQUENCE: 367

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
            20                  25                  30

<210> SEQ ID NO 368
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 368

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 369
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-(2-(4-dodecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 369

His Xaa Glu Gly Thr Phe Thr Ser Asp Val Ser Ser Tyr Leu Glu Gly
 1               5                  10                  15

Gln Ala Ala Xaa Glu Phe Ile Ala Trp Leu Val Arg Xaa Arg
            20                  25                  30

<210> SEQ ID NO 370
<211> LENGTH: 30
<212> TYPE: PRT
<213> ORGANISM: Artificial Sequence
```

```
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-(2-(4-tetradecyl-1-piperazine)-
      acetyl)lysine
<220> FEATURE:
<221> NAME/KEY: VARIANT
<222> LOCATION:
<223> OTHER INFORMATION: this sequence has an amidated c-terminus

<400> SEQUENCE: 370

His Xaa Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Xaa Arg
            20                  25                  30

<210> SEQ ID NO 371
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-(2-(4-hexadecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 371

His Xaa Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Xaa Arg
            20                  25                  30

<210> SEQ ID NO 372
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 372

His Xaa Glu Gly Thr Phe Thr Ser Asp Val Ser Ser Tyr Leu Glu Gly
1               5                   10                  15
```

Gln Ala Ala Arg Glu Phe Ile Ala Trp Leu Val Xaa Xaa Arg
            20                  25                  30

<210> SEQ ID NO 373
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-(2-(4-dodecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 373

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 374
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-(2-(4-tetradecyl-1-piperazine)-
      acetyl)lysine
<220> FEATURE:
<221> NAME/KEY: VARIANT
<222> LOCATION:
<223> OTHER INFORMATION: this sequence has an amidated c-terminus

<400> SEQUENCE: 374

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 375
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-(2-(4-hexadecyl-1-piperazine)-
      acetyl)-lysine
<220> FEATURE:
<221> NAME/KEY: VARIANT

```
<222> LOCATION:
<223> OTHER INFORMATION: this sequence has an amidated c-terminus

<400> SEQUENCE: 375

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Xaa Xaa Arg
            20                  25                  30

<210> SEQ ID NO 376
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 376

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 377
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-(2-(4-dodecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 377

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
            20                  25                  30

<210> SEQ ID NO 378
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
```

```
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-(2-(4-hexadecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 378

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
             20                  25                  30

<210> SEQ ID NO 379
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 379

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Gly Xaa
             20                  25                  30

<210> SEQ ID NO 380
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-dodecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 380

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Gly Xaa
             20                  25                  30

<210> SEQ ID NO 381
```

```
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-tetradecyl-1-piperazine)-
      acetyl)lysine
<220> FEATURE:
<221> NAME/KEY: VARIANT
<222> LOCATION:
<223> OTHER INFORMATION: this sequence has an amidated c-terminus

<400> SEQUENCE: 381

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Gly Xaa
            20                  25                  30

<210> SEQ ID NO 382
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-hexadecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 382

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Gly Xaa
            20                  25                  30

<210> SEQ ID NO 383
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 383
```

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa Xaa
            20                  25                  30

<210> SEQ ID NO 384
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-dodecyl-1-piperazine)-
     acetyl)-lysine
<220> FEATURE:
<221> NAME/KEY: VARIANT
<222> LOCATION:
<223> OTHER INFORMATION: this sequence has an amidated c-terminus

<400> SEQUENCE: 384

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa Xaa
            20                  25                  30

<210> SEQ ID NO 385
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-tetradecyl-1-piperazine)-
     acetyl)lysine
<220> FEATURE:
<221> NAME/KEY: VARIANT
<222> LOCATION:
<223> OTHER INFORMATION: this sequence has an amidated c-terminus

<400> SEQUENCE: 385

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa Xaa
            20                  25                  30

<210> SEQ ID NO 386
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-hexadecyl-1-piperazine)-

```
           acetyl)-lysine
<220> FEATURE:
<221> NAME/KEY: VARIANT
<222> LOCATION:
<223> OTHER INFORMATION: this sequence has an amidated c-terminus

<400> SEQUENCE: 386

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
            20                  25                  30

<210> SEQ ID NO 387
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 387

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
            20                  25                  30

<210> SEQ ID NO 388
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-(2-(4-dodecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 388

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
            20                  25                  30

<210> SEQ ID NO 389
<211> LENGTH: 30
<212> TYPE: PRT
<213> ORGANISM: Artificial Sequence
<220> FEATURE:
<223> OTHER INFORMATION: Mutagen
```

```
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-(2-(4-tetradecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 389

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
         20                  25                  30

<210> SEQ ID NO 390
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 20
<223> OTHER INFORMATION: Xaa = N-epsilon-(2-(4-hexadecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 390

His Xaa Glu Gly Thr Phe Thr Ser Asp Val Ser Ser Tyr Leu Glu Gly
 1               5                  10                  15

Gln Ala Arg Xaa Glu Phe Ile Ala Trp Leu Val Arg Xaa Arg
         20                  25                  30

<210> SEQ ID NO 391
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 391

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
         20                  25                  30
```

<210> SEQ ID NO 392
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-(2-(4-dodecyl-1-piperazine)-
    acetyl)-lysine
<220> FEATURE:
<221> NAME/KEY: VARIANT
<222> LOCATION:
<223> OTHER INFORMATION: this sequence has an amidated c-terminus

<400> SEQUENCE: 392

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 393
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-(2-(4-tetradecyl-1-piperazine)-
    acetyl)-lysine
<220> FEATURE:
<221> NAME/KEY: VARIANT
<222> LOCATION:
<223> OTHER INFORMATION: this sequence has an amidated c-terminus

<400> SEQUENCE: 393

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 394
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = N-epsilon-(2-(4-hexadecyl-1-piperazine)-
    acetyl)-lysine
<220> FEATURE:
<221> NAME/KEY: VARIANT
<222> LOCATION:
<223> OTHER INFORMATION: this sequence has an amidated c-terminus

```
<400> SEQUENCE: 394

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Xaa Xaa Arg
            20                  25                  30

<210> SEQ ID NO 395
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 395

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 396
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-(2-(4-dodecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 396

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 397
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
```

```
<221> NAME/KEY: VARIANT
<222> LOCATION: 30
<223> OTHER INFORMATION: Xaa = N-epsilon-(2-(4-tetradecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 397

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 398
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-(2-(4-hexadecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 398

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Xaa
            20                  25                  30

<210> SEQ ID NO 399
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 399

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Gly Xaa
            20                  25                  30

<210> SEQ ID NO 400
<211> LENGTH: 32
<212> TYPE: PRT
```

```
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-dodecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 400

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Gly Xaa
            20                  25                  30

<210> SEQ ID NO 401
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-tetradecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 401

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Gly Xaa
            20                  25                  30

<210> SEQ ID NO 402
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-hexadecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 402

His Xaa Glu Gly Thr Phe Thr Ser Asp Val Ser Ser Tyr Leu Glu Gly
 1               5                  10                  15
```

```
Gln Ala Arg Arg Glu Phe Ile Ala Trp Leu Val Arg Xaa Arg Gly Xaa
            20                  25                  30

<210> SEQ ID NO 403
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-decyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 403

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
            20                  25                  30

<210> SEQ ID NO 404
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-dodecyl-1-piperazine)-
      acetyl)-lysine
<220> FEATURE:
<221> NAME/KEY: VARIANT
<222> LOCATION:
<223> OTHER INFORMATION: this sequence has an amidated c-terminus

<400> SEQUENCE: 404

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
            20                  25                  30

<210> SEQ ID NO 405
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-tetradecyl-1-piperazine)-
      acetyl)-lysine
<220> FEATURE:
```

```
<221> NAME/KEY: VARIANT
<222> LOCATION:
<223> OTHER INFORMATION: this sequence has an amidated c-terminus

<400> SEQUENCE: 405

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
             20                  25                  30

<210> SEQ ID NO 406
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29, 31
<223> OTHER INFORMATION: Xaa = Aib (alpha-aminoisobutyric acid)
<220> FEATURE:
<221> NAME/KEY: VARIANT
<222> LOCATION: 32
<223> OTHER INFORMATION: Xaa = N-epsilon-(2-(4-hexadecyl-1-piperazine)-
     acetyl)-lysine
<220> FEATURE:
<221> NAME/KEY: VARIANT
<222> LOCATION:
<223> OTHER INFORMATION: this sequence has an amidated c-terminus

<400> SEQUENCE: 406

His Xaa Glu Gly Thr Phe Thr Ser Asp Val Ser Ser Tyr Leu Glu Gly
 1               5                  10                  15

Gln Ala Arg Arg Glu Phe Ile Ala Trp Leu Val Arg Xaa Arg Xaa Xaa
             20                  25                  30

<210> SEQ ID NO 407
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an hydroxydated c-terminus

<400> SEQUENCE: 407

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Xaa
             20                  25                  30

<210> SEQ ID NO 408
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
```

```
<223> OTHER INFORMATION: Xaa = Aib (alpha-aminoisobutyric acid)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an hydroxydated c-terminus

<400> SEQUENCE: 408

His Xaa Glu Gly Thr Phe Thr Ser Asp Val Ser Ser Tyr Leu Glu Gly
 1               5                  10                  15

Gln Ala Lys Arg Glu Phe Ile Ala Trp Leu Val Arg Xaa Xaa
            20                  25                  30

<210> SEQ ID NO 409
<211> LENGTH: 32
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2, 29
<223> OTHER INFORMATION: Xaa = Aib (alpha-aminoisobutyric acid)
<220> FEATURE:
<221> NAME/KEY: VARIANT
<222> LOCATION: 31
<223> OTHER INFORMATION: Xaa = Ava (5-aminovaleric acid)
<220> FEATURE:
<221> NAME/KEY: VARIANT
<222> LOCATION: 32
<223> OTHER INFORMATION: Xaa = Ado (12-aminododecanoic acid)
<220> FEATURE:
<221> NAME/KEY: VARIANT
<222> LOCATION:
<223> OTHER INFORMATION: this sequence has an amidated c-terminus

<400> SEQUENCE: 409

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa Xaa
            20                  25                  30

<210> SEQ ID NO 410
<211> LENGTH: 31
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 2
<223> OTHER INFORMATION: Xaa = Aib (alpha-aminoisobutyric acid)
<220> FEATURE:
<221> NAME/KEY: VARIANT
<222> LOCATION: 29
<223> OTHER INFORMATION: Xaa = beta-Ala (beta-alanine)
<220> FEATURE:
<221> NAME/KEY: VARIANT
<222> LOCATION: 31
<223> OTHER INFORMATION: Xaa = N-epsilon-dodecanoyl-lysine
<220> FEATURE:
<221> NAME/KEY: VARIANT
<222> LOCATION:

<400> SEQUENCE: 410

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Xaa Arg Xaa
```

<210> SEQ ID NO 411
<211> LENGTH: 30
<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 1
<223> OTHER INFORMATION: Xaa = Aib (alpha-aminoisobutyric acid)
<220> FEATURE:
<221> NAME/KEY: VARIANT
<222> LOCATION: 28
<223> OTHER INFORMATION: Xaa = beta-Ala (beta-alanine)
<220> FEATURE:
<221> NAME/KEY: VARIANT
<222> LOCATION: 30
<223> OTHER INFORMATION: Xaa = N-epsilon-decanoyl-lysine
<220> FEATURE:
<221> NAME/KEY: VARIANT
<222> LOCATION:
<223> OTHER INFORMATION: this sequence has an amidated c-terminus

<400> SEQUENCE: 411

Xaa Glu Gly Thr Phe Thr Ser Asp Val Ser Ser Tyr Leu Glu Gly Gln
 1               5                  10                  15

Ala Ala Arg Glu Phe Ile Ala Trp Leu Val Arg Xaa Arg Xaa
            20                  25                  30

<210> SEQ ID NO 412
<211> LENGTH: 33
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = L-His, Ura, Paa, Pta, Amp, Tma-His,
    Des-amino-His, or deleted
<220> FEATURE:
<221> NAME/KEY: VARIANT
<222> LOCATION: 2
<223> OTHER INFORMATION: Xaa = Ala, D-Ala, Aib, Acc, N-Me-Ala,
    N-Me-D-Ala, or N-Me-Gly
<220> FEATURE:
<221> NAME/KEY: VARIANT
<222> LOCATION: 3
<223> OTHER INFORMATION: Xaa = Glu, N-Me-Glu, N-Me-Asp, or Asp
<220> FEATURE:
<221> NAME/KEY: VARIANT
<222> LOCATION: 4
<223> OTHER INFORMATION: Xaa = Gly, Acc, beta-Ala, or Aib
<220> FEATURE:
<221> NAME/KEY: VARIANT
<222> LOCATION: 5
<223> OTHER INFORMATION: Xaa = Thr, or Ser
<220> FEATURE:
<221> NAME/KEY: VARIANT
<222> LOCATION: 6
<223> OTHER INFORMATION: Xaa = Phe, Acc, Aic, Aib, 3-Pal, 4-Pal,
    beta-Nal, Cha, Trp, or X1-Phe
<220> FEATURE:
<221> NAME/KEY: VARIANT
<222> LOCATION: 7
<223> OTHER INFORMATION: Xaa = Thr, or Ser
<220> FEATURE:
<221> NAME/KEY: VARIANT
<222> LOCATION: 8
<223> OTHER INFORMATION: Xaa = Ser, or Aib
<220> FEATURE:
<221> NAME/KEY: VARIANT
<222> LOCATION: 9

-continued

```
<223> OTHER INFORMATION: Xaa = Asp, or Glu
<220> FEATURE:
<221> NAME/KEY: VARIANT
<222> LOCATION: 10
<223> OTHER INFORMATION: Xaa = Val, Acc, Aib, Leu, Ile, Tle, Nle, Abu,
      Ala, or Cha
<220> FEATURE:
<221> NAME/KEY: VARIANT
<222> LOCATION: 11
<223> OTHER INFORMATION: Xaa = Ser, or Thr
<220> FEATURE:
<221> NAME/KEY: VARIANT
<222> LOCATION: 12
<223> OTHER INFORMATION: Xaa = Ser, or Thr
<220> FEATURE:
<221> NAME/KEY: VARIANT
<222> LOCATION: 13
<223> OTHER INFORMATION: Xaa = Tyr, Cha, Phe, 3-Pal, 4-Pal, Acc,
      beta-Nal, or X1-Phe
<220> FEATURE:
<221> NAME/KEY: VARIANT
<222> LOCATION: 14
<223> OTHER INFORMATION: Xaa = Leu, Acc, Aib, Nle, Ile, Cha, Tle, Val,
      Phe, or X1-Phe
<220> FEATURE:
<221> NAME/KEY: VARIANT
<222> LOCATION: 15
<223> OTHER INFORMATION: Xaa = Glu, or Asp
<220> FEATURE:
<221> NAME/KEY: VARIANT
<222> LOCATION: 16
<223> OTHER INFORMATION: Xaa = Gly, Acc, beta-Ala, Glu, or Aib
<220> FEATURE:
<221> NAME/KEY: VARIANT
<222> LOCATION: 17
<223> OTHER INFORMATION: Xaa = Gln, Asp, Asn, or Glu
<220> FEATURE:
<221> NAME/KEY: VARIANT
<222> LOCATION: 18
<223> OTHER INFORMATION: Xaa = Ala, Aib, Val, Abu, Tle, or Acc
<220> FEATURE:
<221> NAME/KEY: VARIANT
<222> LOCATION: 19
<223> OTHER INFORMATION: Xaa = Ala, Aib, Val, Abu, Tle, Acc, Lys, Arg,
      hArg, Orn, HN-CH((CH2)n-N(R10-R11))-C(O), OR NH-CH((CH2)e-X3)-C(O)
<220> FEATURE:
<221> NAME/KEY: VARIANT
<222> LOCATION: 20
<223> OTHER INFORMATION: Xaa = Lys, Arg, hArg, Orn,
      HN-CH((CH2)n-N(R10-R11))-C(O), OR NH-CH((CH2)-X3)-C(O)
<220> FEATURE:
<221> NAME/KEY: VARIANT
<222> LOCATION: 21
<223> OTHER INFORMATION: Xaa = Glu Asp, Leu, Aib, or Lys
<220> FEATURE:
<221> NAME/KEY: VARIANT
<222> LOCATION: 22
<223> OTHER INFORMATION: Xaa = Phe, Pal, beta-Nal, X1-Phe, Aic, Acc,
      Aib, Cha, or Trp
<220> FEATURE:
<221> NAME/KEY: VARIANT
<222> LOCATION: 23
<223> OTHER INFORMATION: Xaa = Ile, Acc, Aib, Leu, Nle, Cha, Tle, Val,
      Abu, Ala, or Phe
<220> FEATURE:
<221> NAME/KEY: VARIANT
<222> LOCATION: 24
<223> OTHER INFORMATION: Xaa = Ala, Aib, or Acc
<220> FEATURE:
<221> NAME/KEY: VARIANT
<222> LOCATION: 25
<223> OTHER INFORMATION: Xaa = Trp, beta-Nal, 3-Pal, 4-Pal, Phe, Acc,
      Aib, or Cha
<220> FEATURE:
<221> NAME/KEY: VARIANT
<222> LOCATION: 26
<223> OTHER INFORMATION: Xaa = Leu, Acc, Aib, Nle, Ile, Cha, Tle, Phe,
      X1-Phe, or Ala
<220> FEATURE:
```

```
<221> NAME/KEY: VARIANT
<222> LOCATION: 27
<223> OTHER INFORMATION: Xaa = Val, Acc, Aib, Leu, Ile, Tle, Nle, Cha,
      Ala, Phe, Abu, Lys, or X1-Phe
<220> FEATURE:
<221> NAME/KEY: VARIANT
<222> LOCATION: 28
<223> OTHER INFORMATION: Xaa = Lys, Arg, hArg, Orn,
      HN-CH((CH2)n-N(R10-R11))-C(O), or NH-CH((CH2)e-X3)-C(O)
<220> FEATURE:
<221> NAME/KEY: VARIANT
<222> LOCATION: 29
<223> OTHER INFORMATION: Xaa = Gly, beta-Ala, D-Ala, Gaba, Ava,
      NH-(CH2)m-C(O), Aib, Acc or D-amino acid
<220> FEATURE:
<221> NAME/KEY: VARIANT
<222> LOCATION: 30
<223> OTHER INFORMATION: Xaa = L- or D-Arg, D- or L-Lys, D- or L-hArg,
      D- or L-Orn, HN-CH((CH2)n-N(R10-R11))-C(O),
      NH-CH((CH2)e-X3)-C(O) or deleted
<220> FEATURE:
<221> NAME/KEY: VARIANT
<222> LOCATION: 31
<223> OTHER INFORMATION: Xaa = Gly, beta-Ala, Gaba, Ava, Aib, Acc, Ado,
      Arg, Asp, Aun, Aec, NH-(CH2)m-C(O), HN-CH((CH2)n-N(R10-R11))-C(O),
      a D-amino acid, or deleted
<220> FEATURE:
<221> NAME/KEY: VARIANT
<222> LOCATION: 32
<223> OTHER INFORMATION: Xaa = D- or L-Lys, D- or L-Arg, D- or L-hArg,
      D- or L-Orn, HN-CH((CH2)n-N(R10-R11))-C(O),
      NH-CH((CH2)e-X3)-C(O)Ava, Ado, Aec, or deleted
<220> FEATURE:
<221> NAME/KEY: VARIANT
<222> LOCATION: 33
<223> OTHER INFORMATION: Xaa = D- or L-Lys, D- or L-Arg,
      HN-CH((CH2)n-N(R10-R11))-C(O), Ava, Ado, or Aec

<400> SEQUENCE: 412

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 413
<211> LENGTH: 31
<212> TYPE: PRT
<213> ORGANISM: Homo sapiens

<400> SEQUENCE: 413

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 414
<211> LENGTH: 32
<212> TYPE: PRT
<213> ORGANISM: Homo sapiens

<400> SEQUENCE: 414

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Arg
            20                  25                  30

<210> SEQ ID NO 415
<211> LENGTH: 30
```

```
-continued

<212> TYPE: PRT
<213> ORGANISM: Artificial Sequence
<220> FEATURE:
<223> OTHER INFORMATION: Mutagen
<220> FEATURE:
<221> NAME/KEY: VARIANT
<222> LOCATION: 13
<223> OTHER INFORMATION: Xaa = 125I radiolabeled Tyr

<400> SEQUENCE: 415

His Ala Glu Gly Thr Phe Thr Ser Asp Val Ser Ser Xaa Leu Glu Gly
 1               5                  10                  15

Gln Ala Ala Lys Glu Phe Ile Ala Trp Leu Val Lys Gly Arg
            20                  25                  30
```